(12) United States Patent
Tashiro et al.

(10) Patent No.: US 9,226,729 B2
(45) Date of Patent: Jan. 5, 2016

(54) ULTRASOUND DIAGNOSTIC SYSTEM, ULTRASOUND IMAGE GENERATION APPARATUS, AND ULTRASOUND IMAGE GENERATION METHOD

(75) Inventors: Rika Tashiro, Ashigara-kami-gun (JP); Kimito Katsuyama, Ashigara-kami-gun (JP); Yukiya Miyachi, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 489 days.

(21) Appl. No.: 13/246,471

(22) Filed: Sep. 27, 2011

(65) Prior Publication Data

US 2012/0078103 A1    Mar. 29, 2012

(30) Foreign Application Priority Data

Sep. 28, 2010 (JP) .................................. 2010-216512
Sep. 28, 2010 (JP) .................................. 2010-216764
Dec. 9, 2010 (JP) .................................. 2010-274872

(51) Int. Cl.
*A61B 8/00* (2006.01)
*A61B 8/08* (2006.01)
(Continued)

(52) U.S. Cl.
CPC ............... *A61B 8/0841* (2013.01); *A61B 8/461* (2013.01); *A61B 8/5215* (2013.01); *G06T 5/50* (2013.01); *G06T 7/0042* (2013.01); *A61B 10/0233* (2013.01); *A61B 2019/5276* (2013.01);
(Continued)

(58) Field of Classification Search
CPC ................... A61B 10/0233; A61B 2019/5276; A61B 2019/5425; A61B 8/0841
See application file for complete search history.

(56) References Cited

U.S. PATENT DOCUMENTS 5,797,397 A * 8/1998 Rosenberg ................... 600/400
5,967,985 A    10/1999 Hayakawa
(Continued)

FOREIGN PATENT DOCUMENTS

JP    08-299344 A    11/1996
JP    1133021 A    2/1999
(Continued)

OTHER PUBLICATIONS

Dong et al, A Novel Method for Enhanced Needle Localization Using Ultrasound-Guidance, Advances in Visual Computing, Lecture Notes in Computer Science, vol. 5875, 2008, pp. 914-923.*
(Continued)

*Primary Examiner* — Unsu Jung
*Assistant Examiner* — Saurel J Selkin
(74) *Attorney, Agent, or Firm* — Sughrue Mion, PLLC

(57) ABSTRACT

The ultrasound diagnostic apparatus, ultrasound image generation apparatus and method transmit ultrasound waves to a subject into which a puncture tool is inserted, receive reflected waves reflected from the subject and the puncture tool, and generate echo signals of time-sequential frames based on the received reflected waves, and generate an ultrasound image of the subject based on the generated echo signals. These apparatus and method generate a differential echo signal between time-sequential frames from the echo signals, perform a tip detection process based on the differential echo signal to thereby detect at least one tip candidate including a tip end of the puncture tool, highlight a tip candidate of the puncture tool detected to thereby generate a tip image, and display the tip image of the highlighted puncture tool so as to be superimposed on the generated ultrasound image.

19 Claims, 34 Drawing Sheets

(51) Int. Cl.
*G06T 5/50* (2006.01)
*G06T 7/00* (2006.01)
*A61B 10/02* (2006.01)
*A61B 19/00* (2006.01)

(52) U.S. Cl.
CPC ............... *A61B2019/5425* (2013.01); *G06T 2207/10132* (2013.01); *G06T 2207/20221* (2013.01); *G06T 2207/30021* (2013.01)

(56) References Cited

U.S. PATENT DOCUMENTS

| | | | |
|---|---|---|---|
| 6,146,329 A | 11/2000 | Hayakawa | |
| 6,221,016 B1 | 4/2001 | Hayakawa | |
| 2004/0133168 A1* | 7/2004 | Salcudean et al. | 604/164.13 |
| 2006/0058643 A1* | 3/2006 | Florent et al. | 600/423 |
| 2007/0016035 A1 | 1/2007 | Hashimoto | |

FOREIGN PATENT DOCUMENTS

| JP | 2000-107178 A | 4/2000 |
|---|---|---|
| JP | 2001-269339 A | 10/2001 |
| JP | 2004215701 A | 8/2004 |
| JP | 2006-320378 A | 11/2006 |
| JP | 2006-346477 A | 12/2006 |
| JP | 2007-222264 A | 9/2007 |
| JP | 4030644 B2 | 1/2008 |

OTHER PUBLICATIONS

Notification of Reasons for Refusal, dispatched Nov. 5, 2013, issued in corresponding JP Application No. 2010-216764, 6 pages in English and Japanese.

* cited by examiner

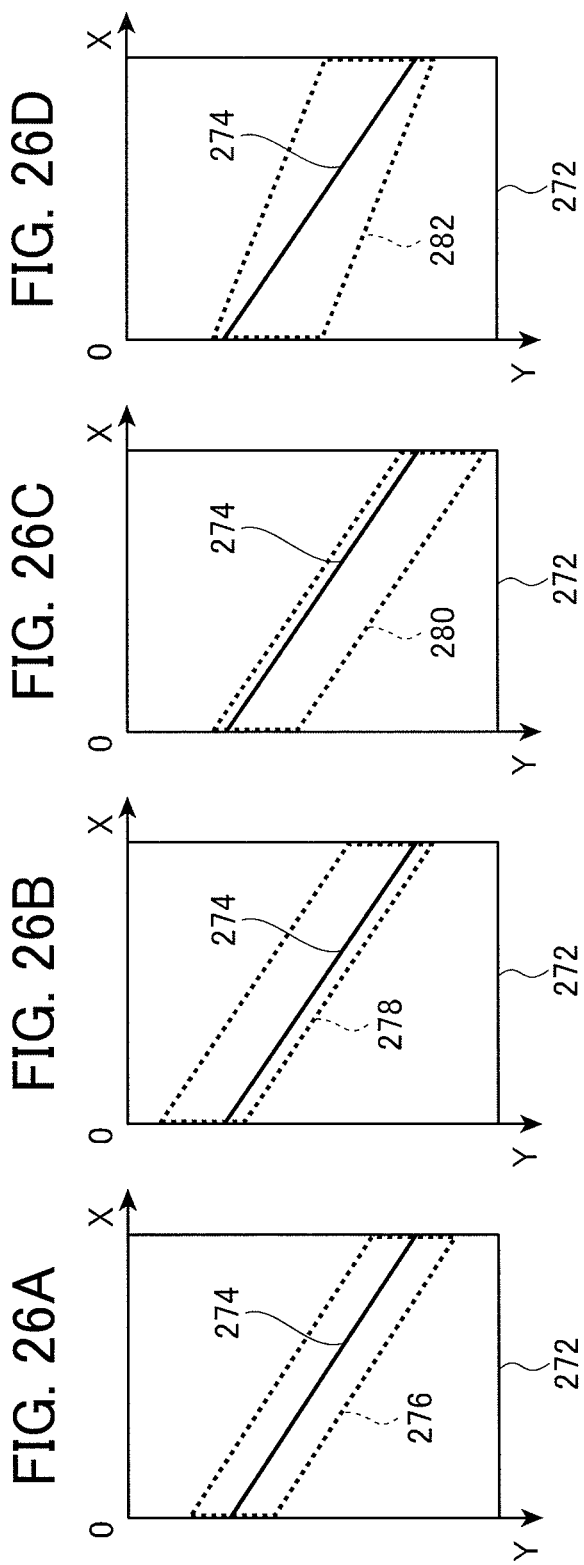

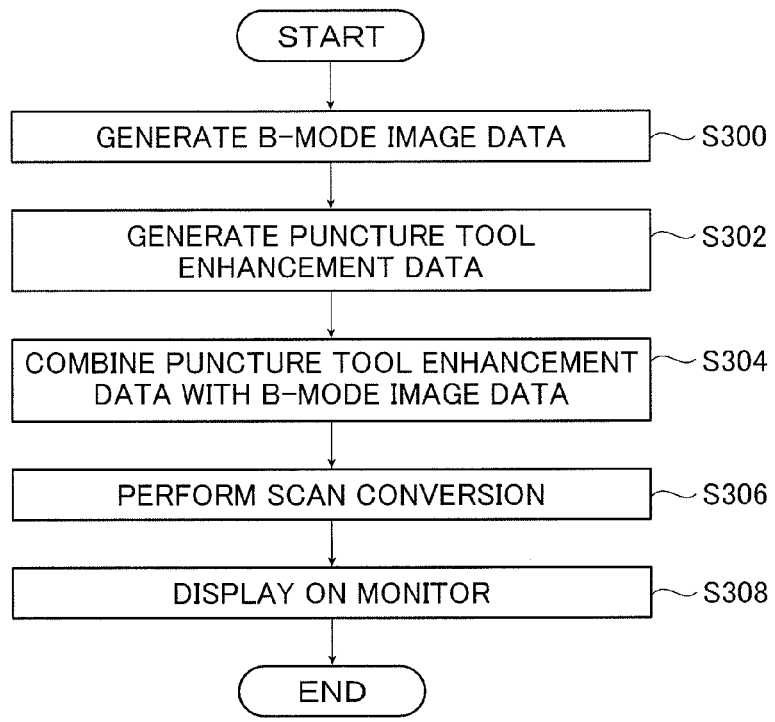
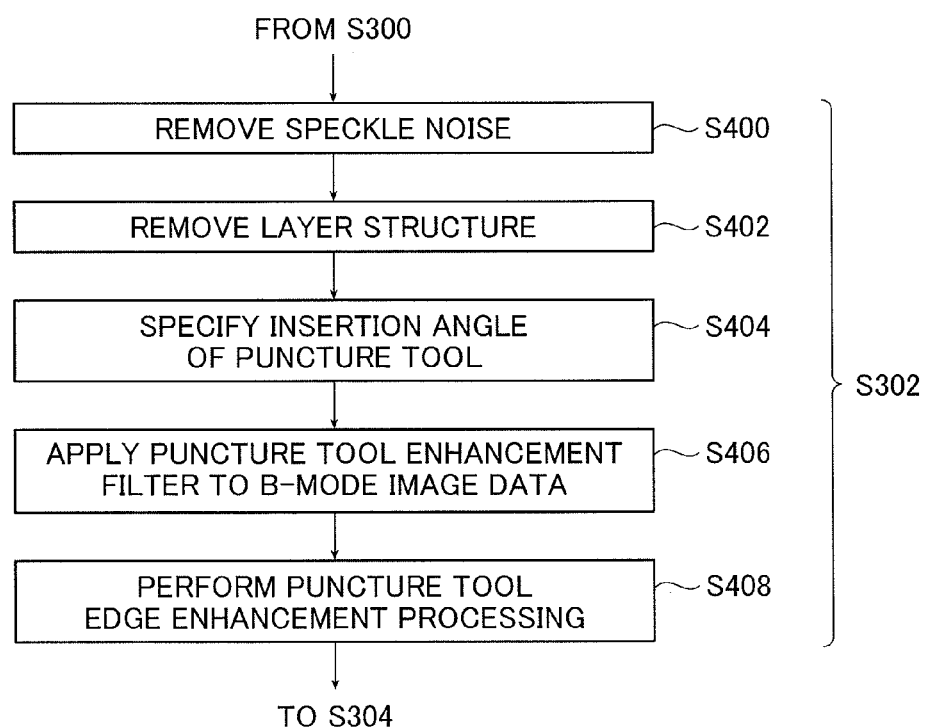

ULTRASOUND DIAGNOSTIC SYSTEM, ULTRASOUND IMAGE GENERATION APPARATUS, AND ULTRASOUND IMAGE GENERATION METHOD

BACKGROUND OF THE INVENTION

The present invention relates to an ultrasound diagnostic apparatus, an ultrasound image generation apparatus, and an ultrasound image generation method. More particularly, the invention relates to an ultrasound diagnostic apparatus, an ultrasound image generation apparatus, and an ultrasound image generation method used when displaying a puncture tool on a screen together with body tissues, specifically when displaying the tip end of a puncture tool such as a puncture needle in an ultrasound image in an accurate and appropriate manner when performing paracentesis.

In medical fields, an ultrasound image generation apparatus for generating ultrasound images and an ultrasound diagnostic apparatus using the generated ultrasound images have been put into practical use and are used widely for diagnosis and examination. In general, this kind of ultrasound image generation apparatus and ultrasound diagnostic apparatus (hereinafter referred collectively to as an ultrasound diagnostic apparatus) includes an ultrasound probe including an array of vibrators therein and a diagnostic apparatus main body connected to the ultrasound probe. In the ultrasound diagnostic apparatus, the ultrasound probe transmits ultrasound waves toward a subject to be examined, that is to say, a patient to thereby irradiate the patient with the ultrasound waves. Then, the ultrasound probe receives echoes (reflection sound) of the ultrasound waves reflected from the patient, namely signals (hereinafter referred to as echo signals) originating from ultrasound echoes from the subject. The received echo signals are electrically processed by the diagnostic apparatus main body whereby ultrasound tomographic images of the patient, called ultrasound images are generated and displayed on a monitor or the like.

Moreover, the ultrasound diagnostic apparatus is also used when a physician performs a paracentesis which involves inserting a puncture tool, for example, a puncture needle, in a desired site to collect a tissue sample for the purpose of diagnosing cell tissues.

In the paracentesis, it is important to enable the puncture needle to be observed on a monitor, namely as an image and to allow the puncture needle to reach a target object. To allow the puncture needle to certainly reach a target object or a target site, the physician inserts the puncture needle along a predetermined insertion path (a path along which the puncture needle is inserted within the body of a patient) while observing ultrasound images. Moreover, when establishing a definitive cancer diagnosis such as cell tissue diagnosis based on biopsy or the like, it is also important to capture and store an image in which the puncture needle is inserted into a target object as an evidence image.

When performing such paracentesis, it is necessary to allow the puncture needle to reach a treatment target such as a target site or a target object and to perform drainage of excess fluid from the treatment target or perform injection (PEIT) of a substance to the treatment target. Thus, it is important to observe the puncture needle, particularly, the tip end thereof, on a monitor (ultrasound image) in a reliable, accurate, and appropriate manner.

To solve this problem, according to an ultrasound imaging technique disclosed in Patent Document 1 (JP 4030644 B), in order to detect the accurate tip position of a puncture needle inserted into a subject to be examined, the puncture needle is inserted while being mechanically vibrated by a vibration imparting mechanism attached to the base end thereof, whereby a Doppler image of the puncture needle is obtained based on a Doppler signal and displayed so as to be superimposed on a B-mode image to thereby obtain the image of the puncture needle.

According to an ultrasound diagnostic apparatus disclosed in Patent Document 2 (JP 2001-269339 A), B-mode ultrasound tomographic image frame data obtained by an ultrasound probe are stored in a memory, a difference between the previous frame data and the presently obtained frame data is calculated to obtain a spatial variation as digital data, and the digital data is added to the presently obtained frame data, whereby a desired puncture needle image is displayed in a B-mode ultrasound image. As a result, the technique of Patent Document 2 can display a clear puncture needle image based on only the B-mode ultrasound tomographic image frame data without using the vibration imparting mechanism and Doppler-mode processing which were necessary in the ultrasound imaging technique disclosed in Patent Document 1.

According to an ultrasound-guided puncture system disclosed in Patent Document 3 (JP 2000-107178 A), signals received by an ultrasound probe, transmitted from a subject to be examined into which a puncture needle is inserted are processed to generate B-mode image signals, and a B-mode ultrasound tomographic image is displayed on a display device based on the B-mode image signals. Moreover, a portion which has a higher luminance than the ultrasound image being displayed and in which the luminance varies abruptly is extracted and colored, and the colored extracted portion is displayed so as to be superimposed on an updated ultrasound tomographic image. As a result, the technique of Patent Document 3 can provide an inexpensive ultrasound-guided puncture system capable of performing treatment and examination in a reliable and satisfactory manner without missing the tip position of a puncture needle inserted once into a patient.

Moreover, Patent Document 4 (JP 2006-346477 A) discloses an ultrasound diagnostic apparatus as an apparatus for displaying a puncture guide line serving as a guide for inserting a puncture needle, in which an advancing angle of the puncture needle is calculated from a linear ultrasound echo signal of a predetermined length or longer, and a puncture guide line corresponding to the advancing angle is displayed so as to be superimposed on a B-mode image which is an ultrasound image generated from echo signals.

Furthermore, Patent Document 5 (JP 8-299344 A) discloses an ultrasound diagnostic apparatus in which the amount of shift between an insertion path along which a puncture needle is inserted and a predetermined puncture guide line is detected, and the guide line is moved from a reference trajectory corresponding to a reference position of the puncture needle so as to match the ultrasound image of the puncture needle with the guide line to thereby display a corrected puncture guide line.

In paracentesis, since the burden on a patient and the degree of invasiveness decrease as the puncture needle becomes narrower, a puncture needle which is as narrow as possible is used depending on a risk or the like. However, as the puncture needle becomes narrower, the ability to draw it on an ultrasound image also decreases, and the puncture needle is displayed in a disconnected manner.

To solve this problem, Patent Document 6 (JP 2006-320378 A) discloses an ultrasound diagnostic apparatus in which a plurality of images are acquired by irradiating ultrasound waves in a direction where strong echo signals are obtained, and the images are combined and displayed so as to suppress a puncture needle from being displayed in a disconnected manner. Moreover, Patent Document 7 (JP 2007-222264 A) discloses an ultrasound diagnostic apparatus which displays a clear image of a tissue structure while suppressing speckles by adaptively changing image processing conditions in accordance with a local property of the tissue.

SUMMARY OF THE INVENTION

However, in the technique disclosed in Patent Document 1, a special mechanism for mechanically vibrating the puncture needle is needed, which increases the size and cost of an apparatus. Moreover, when performing ultrasound-guided central venous puncture, there is a problem in that it is difficult to separate the Doppler signal from blood vessels and the Doppler signal from the puncture needle.

Here, in paracentesis, since the burden on a patient and the degree of invasiveness decrease as the puncture needle becomes narrower, a puncture needle which is as narrow as possible is used depending on the risks or the like. However, as the puncture needle becomes narrower, the ability to draw it on an ultrasound image also decreases, and the puncture needle is displayed in a disconnected manner. Thus, there is a problem in that it is difficult to display the position or shape of the puncture needle precisely.

Moreover, in the technique disclosed in Patent Document 2, it is described that it is possible to solve the problem associated with the technique disclosed in Patent Document 1 and display a clear puncture needle image based on only the B-mode ultrasound tomographic image frame data.

However, as described above, when a narrow puncture needle is used, the B-mode ultrasound tomographic image frame data itself is data with which it is difficult to display the position or shape of the puncture needle precisely. Thus, there is a problem in that it is difficult to obtain accurate spatial variation data caused by insertion of the puncture needle from the differential data and to obtain an accurate puncture needle image.

Furthermore, when inserting a puncture needle into a subject to be examined such as a patient or the like, the spatial variation may occur not only when only the position or shape of the puncture needle varies spatially but also when the subject moves with the movement of a patient or the like or when the position or shape of the subject itself varies with insertion of the puncture needle. In this case, the differential data in Patent Document 2 includes spatial variation data associated with not only the insertion of the puncture needle but also the movement of the subject or a variation in the subject itself. Thus, there is a problem in that it is difficult to separate only the spatial variation data associated with the insertion of the puncture needle and to separate only the puncture needle image. Moreover, since the B-mode ultrasound tomographic image frame data itself includes noise, the differential data also includes data resulting from noise. Thus, there is a problem in that unless a process of separating data resulting from noise is performed, it is difficult to obtain only the puncture needle image.

Furthermore, in the technique disclosed in Patent Document 3, similarly to the technique disclosed in Patent Document 2, the latest image data is compared with image data one frame before to extract a varying portion in the high luminance portion of the ultrasound tomographic image, and the extracted portion is colored and displayed as the tip end portion of the puncture needle. However, in some cases, the varying portion of the high luminance portion may be present not only as a variation in the high luminance portion caused by the insertion of the puncture needle but also as a variation in the high luminance portion caused by the movement of the subject, a variation in the subject itself, or noise. In this case, there is a problem in that it is difficult to separate only the movement of the tip end portion of the puncture needle caused by the insertion and to separate only the tip end portion of the puncture needle.

Moreover, in the technique disclosed in Patent Document 3, although the high luminance portion of the ultrasound tomographic image is a puncture needle, it is difficult to determine which high luminance portion corresponds to the puncture needle. As described above, when a narrow puncture needle is used, there is a problem in that it is difficult to extract only a high luminance portion corresponding to the puncture needle within an ultrasound tomographic image in which it is difficult to display the position or shape of the puncture needle precisely.

However, in the ultrasound diagnostic apparatus of the related art, there is a problem in that it is difficult to draw a puncture needle on an ultrasound image, and the puncture needle is displayed in a disconnected manner, so that the accurate position of the puncture needle is not clear. Various reasons can be considered as the cause of this problem. For example, this problem may be caused due to the fact that since the puncture needle has a smooth surface, and scattering of ultrasound waves barely occurs, the intensity of echoes returning to a probe from the puncture needle which is inserted obliquely with respect to the direction of irradiating ultrasound waves decreases.

Moreover, the ultrasound diagnostic apparatuses disclosed in Patent Documents 4 and 5 are designed to display the puncture guide line but do not address the problem in which the puncture needle is drawn in a disconnected manner. In particular, the ultrasound diagnostic apparatus of Patent Document 4 does not have a function of correcting the ultrasound image of the puncture needle and the guide line, and the ultrasound diagnostic apparatus of Patent Document 5 does not have a function of updating a reference position. Thus, even when the puncture guide line is displayed, the puncture needle may be bent when inserting it into a stiff tissue, and thus, the puncture needle may not be drawn along the puncture guide line. Moreover, although both ultrasound diagnostic apparatuses display the guide line of the insertion path, none of the systems takes a case of storing an evidence image into consideration and suggests which luminance on the ultrasound image corresponds to a luminance indicative of the puncture needle.

Furthermore, although the ultrasound diagnostic apparatus disclosed in Patent Document 6 can display the puncture needle in a smoothly connected manner to some extent, there is a problem in that if the disconnected portions of the puncture needle in a plurality of images to be combined occur at the same position of the images, it is difficult to eliminate the disconnection even when the images are combined. Moreover, when puncturing into a stiff tissue, since the puncture needle is likely to be bent, and strong echo signals may not always be received, there is a problem in that the technique disclosed in Patent Document 6 is difficult to use. Furthermore, in the ultrasound diagnostic apparatus of Patent Document 7, when the puncture needle is drawn in a disconnected manner in a state where the luminance thereof is lower than that of other tissues, although it is possible to display the tissue structure precisely, there is a problem in that it is difficult to display the position or shape of the puncture needle precisely.

The invention has been made in view of the above problems, and a first object of the invention is to solve the problems of the related art and to provide an ultrasound diagnostic apparatus and an ultrasound image generation method capable of displaying the tip end of a puncture tool on an ultrasound image in an accurate, appropriate, and easily visible manner without using a special tool for mechanically vibrating the puncture tool such as a puncture needle and Doppler-mode processing when performing paracentesis.

A second object of the invention is to provide an ultrasound image generation apparatus and an ultrasound image generation method capable of generating an image for presenting users with the position of a puncture tool such as a puncture needle in an accurate and reliable manner.

A third object of the invention is to provide an ultrasound image generation apparatus and an ultrasound image generation method capable of generating an ultrasound image in which a puncture tool is displayed to be easily visible to users.

According to a first aspect of the invention, it is possible to display the tip end of a puncture tool on an ultrasound image in an accurate, appropriate, and easily visible manner without using a special tool for mechanically vibrating the puncture tool such as a puncture needle and Doppler-mode processing when performing paracentesis.

As a result, according to this aspect, even when a puncture tool such as a narrow puncture needle is used, it is possible to enable the tip end of the puncture tool to reach a target site in a reliable manner.

According to a second aspect of the invention, it is possible to generate an image for presenting users with the position of a puncture tool such as a puncture needle in an accurate and reliable manner and to specify the accurate position of a puncture tool such as a puncture needle in a reliable manner.

Moreover, according to this aspect, it is possible to detect feature points on a puncture needle which is a puncture tool and to connect these feature points into a line such as a straight line or a curve. Thus, even when the puncture needle is displayed in a disconnected manner, the connection of the puncture needle can be made easily understood.

Furthermore, according to this aspect, the line of a puncture needle which is a puncture tool can be corrected in a time-sequential manner. Thus, even when an insertion path changes due to bending of the puncture needle, the presence of stiff tissues, shift of a probe, or the like, it is possible to draw the line of the puncture needle with high precision.

Furthermore, according to this aspect, the connected line can be displayed with gradation by referencing the luminance of an ultrasound image. Thus, the connection of the puncture needle which is a puncture tool can be made easily understood while displaying the puncture needle with the luminance information of the ultrasound image.

According to a third aspect of the invention, it is possible to generate an ultrasound image in which a puncture tool is displayed to be easily visible to users.

Moreover, according to this aspect, it is possible to apply a puncture tool enhancement processing in accordance with the shape or insertion angle of the puncture tool.

Furthermore, according to this aspect, the precision of the puncture tool enhancement processing can be increased by applying preprocessing such as speckle removal.

Furthermore, according to this aspect, a process for enhancing the line of the puncture tool such as a puncture needle can be applied after the puncture tool enhancement filter is applied.

Furthermore, according to this aspect, preprocessing for removing a layer structure other than the puncture tool such as a puncture needle can be performed.

BRIEF DESCRIPTION OF THE DRAWINGS

FIG. 26A is a view of a puncture needle presence region created by vertically expanding a puncture needle candidate line by the same width, FIG. 26B is a view of a puncture needle presence region shifted upward, FIG. 26C is a view of a puncture needle presence region shifted downward, and FIG. 26D shows a case where the slope of a puncture needle candidate line is different from the slope of a puncture needle presence region.

FIG. 29 is a flowchart showing an example of an operation of the ultrasound image generation apparatus according to the third aspect of the invention and an example of the ultrasound image generation method according to the invention.

FIG. 30 is a flowchart showing the details of a step of generating puncture tool enhancement data in the ultrasound image generation method shown in FIG. 29.

DETAILED DESCRIPTION OF THE INVENTION

An ultrasound diagnostic apparatus, an ultrasound image generation apparatus, and an ultrasound image generation method according to the invention will be described in detail based on preferred embodiments shown in the accompanying drawings.

Figure 1:
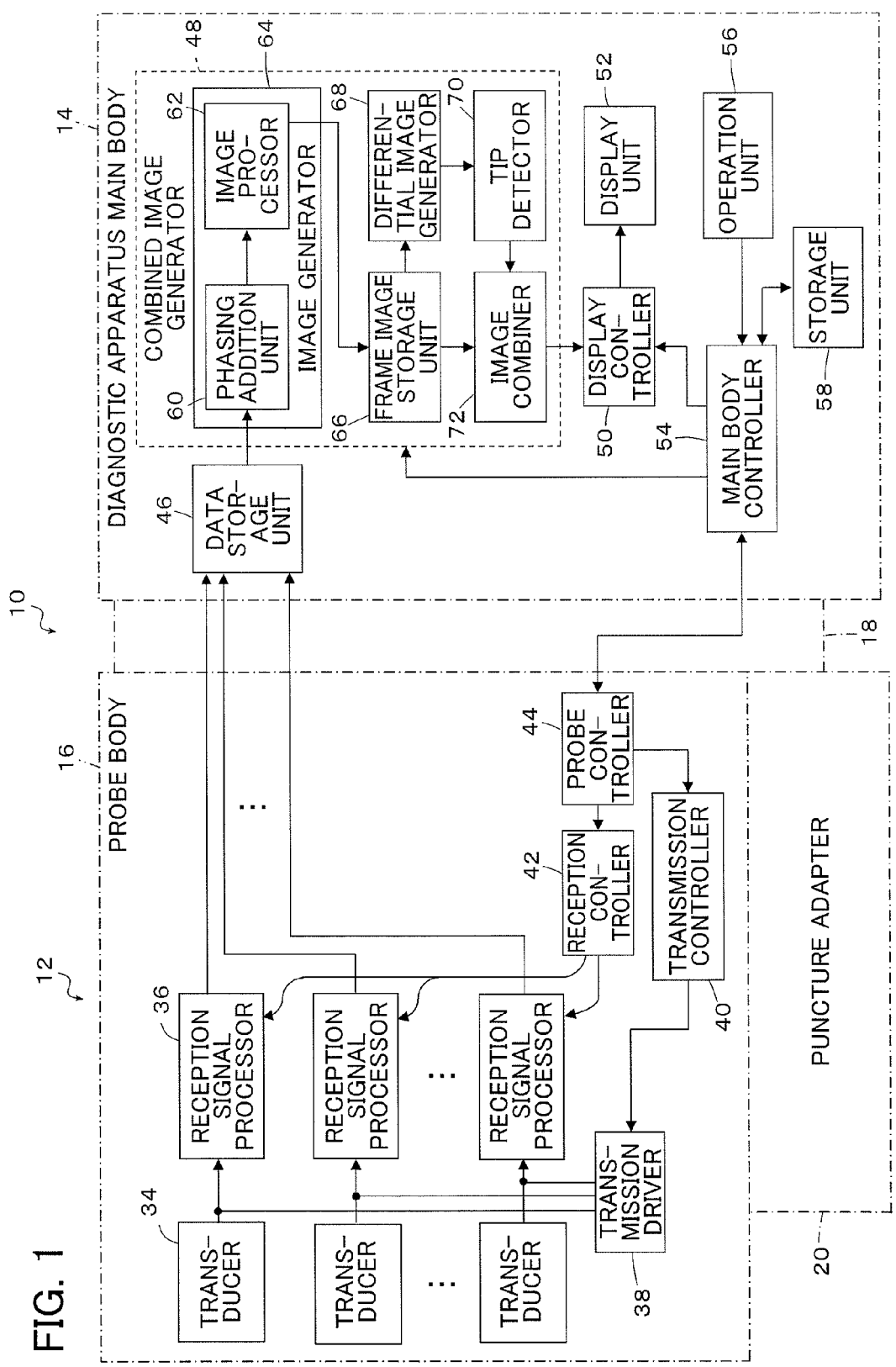
FIG. 1 is a block diagram schematically showing a configuration of an embodiment of an ultrasound diagnostic apparatus according to a first aspect of the invention.
Figure 2:
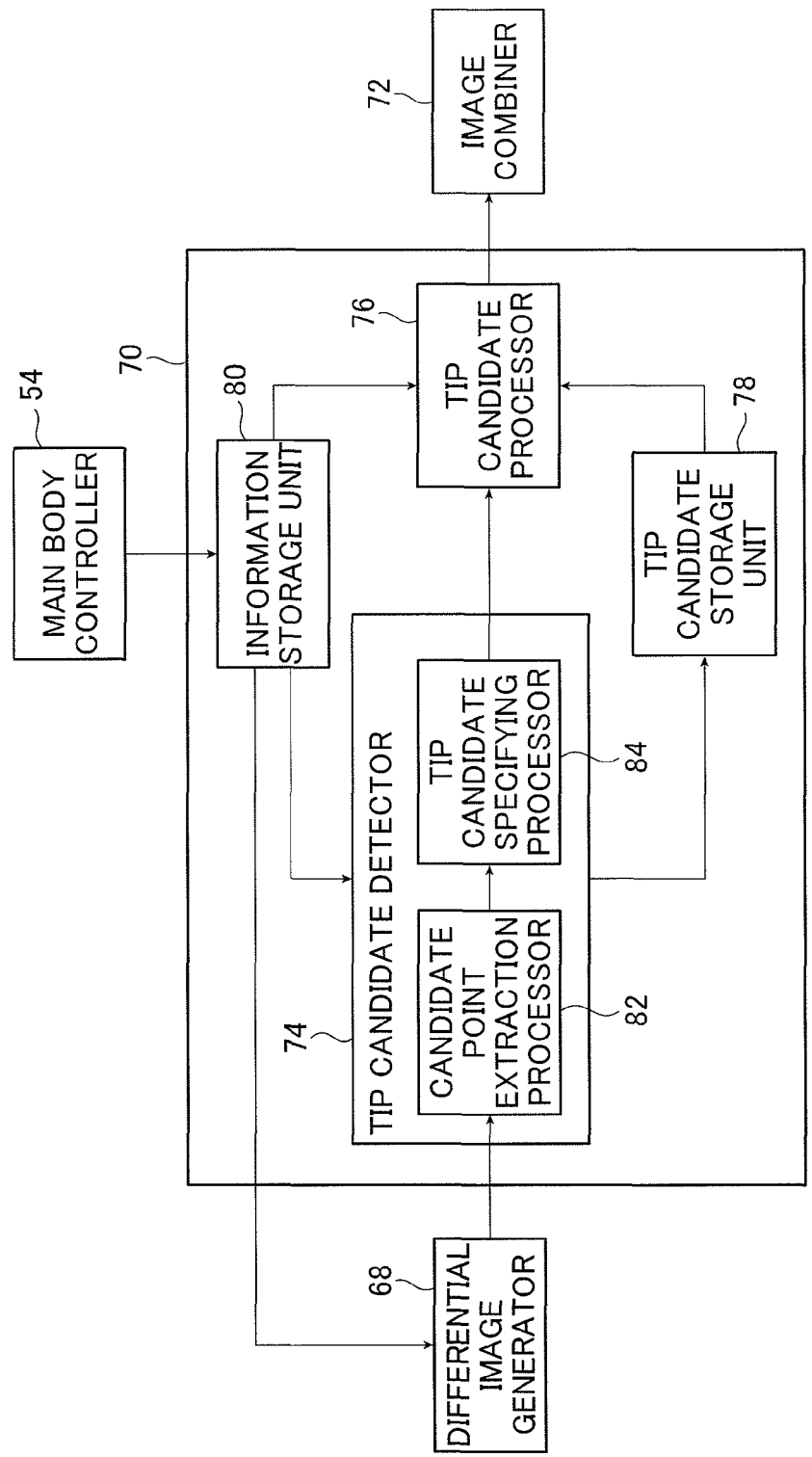
FIG. 2 is a block diagram showing the details of an example of a puncture needle tip detector of a combined image generator of the ultrasound diagnostic apparatus shown in FIG. 1.

FIG. 1 is a block diagram schematically showing a configuration of an embodiment of an ultrasound diagnostic apparatus according to a first aspect of the invention, which performs an ultrasound image generation method according to the first aspect of the invention. FIG. 2 is a block diagram showing the details of an embodiment of a puncture needle tip detector of a combined image generator of the ultrasound diagnostic apparatus shown in FIG. 1.

An ultrasound diagnostic apparatus 10 of the present aspect is an apparatus which irradiates (transmits) ultrasound waves to a subject to be examined, in particular, the subject into which a puncture tool (not shown) such as a puncture needle is inserted, generates and displays ultrasound images obtained by receiving ultrasound waves (echoes) reflected from the subject and the puncture tool, in particular, ultrasound images in which the tip end portion of the puncture tool is combined, and provides the ultrasound images for diagnosis of ultrasound images. The ultrasound diagnostic apparatus 10 includes an ultrasound probe 12 and a diagnostic apparatus main body 14 to which the ultrasound probe 12 is connected. In the following description, although a puncture needle is described as a representative example of the puncture tool, the puncture tool is not limited to this.

The ultrasound probe 12 is also called a probe and used by being pressed against a subject to be examined. The ultrasound probe 12 is configured to transmit and receive ultrasound waves and output received echo signals to the diagnostic apparatus main body 14 and includes a probe body 16, a communication cable 18, and a puncture adapter 20.

The probe body 16 is a transducer which converts electrical signals into ultrasound waves to irradiate (transmit) the ultrasound waves and receives ultrasound waves reflected from the subject to convert the ultrasound waves into electrical signals (echo signals). Basically, the probe body 16 is a known ultrasound probe and may be any scanning-type ultrasound probe of such as, for example, a linear scanning type, a convex scanning type, or a sector scanning type.

A detailed configuration of the probe body 16 will be described later.

The probe body 16 includes an ultrasound wave transceiving surface (not shown) for transmitting and receiving ultrasound waves. The communication cable 18 is connected to a surface of the probe body 16 opposite to the ultrasound wave transceiving surface, and the puncture adapter 20 is disposed on a side surface of the ultrasound wave transceiving surface.

The communication cable 18 is configured to transmit the echo signals from the probe body 16 to the diagnostic apparatus main body 14.

The puncture adapter 20 serves as a guide for inserting a puncture tool such as a puncture needle into a subject to be examined when performing paracentesis using the ultrasound diagnostic apparatus 10. A guide groove (not shown) for inserting the puncture needle into the subject at a predetermined angle is formed in the puncture adapter 20, and the puncture needle is inserted along the guide groove whereby it is inserted into the subject at a predetermined angle. That is, the angle (hereinafter referred to as an insertion angle) at which the puncture needle is inserted into the subject is determined by the angle of the guide groove of the puncture adapter 20 with respect to the subject. The guide groove of the puncture adapter 20 is configured to be able to change the angle with respect to the subject and to adjust the insertion angle.

The puncture adapter 20 is preferably connected physically and electrically to the probe body 16. In this case, it is possible to store information on the insertion angle in the puncture adapter 20. When the puncture adapter 20 is physically connected to the probe body 16, it is possible to output a signal representing the insertion angle to the probe body 16 since the puncture adapter 20 is also electrically connected to the probe body 16. Moreover, whenever the angle of the groove with respect to the subject changes, the puncture adapter 20 is capable of outputting the signal representing the present insertion angle to the probe body 16.

As shown in FIG. 1, the probe body 16 includes a plurality of ultrasound transducers 34, a plurality of reception signal processors 36, a transmission driver 38, a transmission controller 40, a reception controller 42, and a probe controller 44.

The plurality of ultrasound transducers 34 form a 1D or 2D array of vibrators, and each of the plurality of reception signal processors 36 is connected so as to correspond to each of the plurality of transducers 34. Moreover, the transmission controller 40 is connected to the plurality of transducers 34 through the transmission driver 38, the reception controller 42 is connected to the plurality of reception signal processors 36, and the transmission controller 40 and the reception controller 42 are connected to the probe controller 44.

Moreover, the reception signal processors 36 are connected to a data storage unit 46 of the diagnostic apparatus main body 14 through the communication cable, and the probe controller 44 is connected to a main body controller 54 through the communication cable.

Each of the plurality of transducers 34 transmits ultrasound waves toward the subject in accordance with a driving signal supplied from the transmission driver 38, receives ultrasound echoes from the subject, and outputs the reception signals. Each transducer 34 is formed of a vibrator in which an electrode is formed on both ends of a piezoelectric body that is formed of piezoelectric ceramics represented by PZT (lead zirconate titanate) or a polymer piezoelectric element represented by PVDF (polyvinylidene fluoride), for example.

When a pulsating or continuous voltage is applied to the electrodes of each vibrator, the piezoelectric body of the vibrator expands and contracts, pulsating or continuous ultrasound waves are generated from each vibrator, and an ultrasound beam is formed by the combination of these ultrasound waves. Moreover, each vibrator receives a propagating ultrasound wave and expands and contracts to generate electrical signals, and these electrical signals are output as reception signals of ultrasound waves.

The transmission driver 38 includes a plurality of pulsers each generating a high-voltage electrical signal serving as a driving signal for generating ultrasound waves, for example. The transmission driver 38 supplies the driving signals to the plurality of transducers 34 by adjusting the amount of delay thereof based on a transmission delay pattern selected by the transmission controller 40 so that the ultrasound waves transmitted from the plurality of transducers 34 form an ultrasound beam having a large width covering the area of tissues within the subject.

The reception signal processor 36 of each channel performs various processing on the reception signal output from the corresponding transducer 34 under the control of the reception controller 42 to thereby generate a complex baseband signal. The processing includes amplification by an amplifier, rejection of high-frequency components by a low-pass filter, A/D conversion by an A/D converter, and quadrature detection or quadrature sampling. The reception signal processor 36 samples the complex baseband signal to thereby generate sample data including information on the area of tissues. The reception signal processor 36 may perform data compression processing for high-efficiency encoding on the data obtained by sampling the complex baseband signal to thereby generate the sample data.

In this specification, signals may be used as those which mainly represent signal levels (signal values) in hardware, and data may be used as those which are processed by software and represent magnitude (data values).

The probe controller 44 controls respective parts of the probe body 16 based on various control signals transmitted from the diagnostic apparatus main body 14.

As shown in FIG. 1, the diagnostic apparatus main body 14 includes the data storage unit 46, a combined image generator 48, a display controller 50, a display unit 52, the main body controller 54, an operation unit 56, and a storage unit 58.

In the diagnostic apparatus main body 14, the data storage unit 46 is connected to the combined image generator 48 and the plurality of reception signal processors 36 of the probe body 16. The combined image generator 48 is connected to the display unit 52 through the display controller 50. The main body controller 54 is connected to the combined image generator 48 and the display controller 50. Moreover, the main body controller 54 is connected to the operation unit 56 and the storage unit 58.

The data storage unit 46 is formed of a memory, a hard disk, or the like, and stores at least one frame of sample data which are time-sequentially transmitted from the reception signal processors 36 of the ultrasound probe 12 through the communication cable 18.

The combined image generator 48 performs reception focusing processing on sample data of each frame read from the data storage unit 46 to thereby generate image data (B-mode image data or signal) of an ultrasound image which is a B-mode image of one frame. In particular, the combined image generator 48 generates image data (image signal) of an ultrasound diagnostic image such as a combined ultrasound image in which a tip image which is the image of a highlighted puncture needle tip is combined. Here, the B-mode image data is so-called ultrasound image data and means image data which represents the amplitude of an acoustic-ray signal by luminance, and the B-mode image means a so-called ultrasound image.

In this specification, since an image can be considered as a collection of image data or image signals of respective pixels, a collection of image data or image signals representing an image is also simply referred to as an image.

The details of the combined image generator 48 will be described later.

The display controller 50 performs control based on the ultrasound image signal generated by the combined image generator 48 so as to cause the display unit 52 to display an ultrasound image, in particular, an ultrasound diagnostic image in which the puncture needle tip is highlighted. The display controller 50 includes a DSC (Digital Scan Converter). In the display controller 50, the DSC converts (rasterizes) the ultrasound image signal into an image signal corresponding to a general television signal scanning format and performs necessary image processing such as gradation processing to thereby convert the rasterized image signal into a display image signal for display on the display unit 52.

The display unit 52 displays an ultrasound image based on the display image signal converted by the display controller 50, and includes a display device or a monitor such as an LCD, for example. The display unit 52 displays the highlighted tip end portion of the puncture needle so as to be superimposed on the ultrasound image under the control of the display controller 50.

The operation unit 56 enables an operator to input instructions for operating the ultrasound diagnostic apparatus 10 and is a unit that sets imaging menus, imaging conditions, and the like and instructs imaging of a subject to be examined. The operation unit 56 includes various input means such as input keys, dial buttons, a trackball, a touch panel, and the like for setting imaging menus, imaging conditions, and the like.

Moreover, the operation unit 56 also has a function of inputting and setting the position of a target (target site) and inputting instructions regarding the settings on an insertion angle. Furthermore, the operation unit 56 may also include a function of inputting instructions regarding an insertion position of a puncture needle. The operation unit 56 supplies the input instructions regarding the settings on the target position, the insertion angle, and the insertion position to the main body controller 54.

The main body controller 54 controls the respective parts within the diagnostic apparatus main body 14 including the combined image generator 48 and the display controller 50. The main body controller 54 is connected to the probe controller 44 of the probe body 16 through the communication cable 18 and supplies a control signal for controlling the operation of the probe body 16 to the probe controller 44.

The storage unit 58 is formed of a memory, a hard disk, or the like, and stores an operation program for operating the respective parts within the diagnostic apparatus main body 14 including the combined image generator 48 and the display controller 50 which are controlled by the main body controller 54. The main body controller 54 reads the operation program for operating the respective parts within the diagnostic apparatus main body 14 from the storage unit 58 as necessary and operates the respective parts within the diagnostic apparatus main body 14 in accordance with the read operation program.

The combined image generator 48 includes an image generator 64, a time-sequential frame image storage unit (hereinafter also referred to simply as an image storage unit) 66, a time-sequential frame differential image generator (hereinafter also referred to simply as a differential image generator) 68, a puncture needle tip detector (hereinafter also referred to simply as a tip detector) 70, and an image combiner 72.

The image generator 64 generates a B-mode image signal which is tomographic image information from the sample data of each frame read from the data storage unit 46 and includes a phasing addition unit 60 and an image processor 62.

The phasing addition unit 60 selects one reception delay pattern from a plurality of reception delay patterns stored in advance in accordance with a reception direction set in the main body controller 54, gives respective delays to the plurality of complex baseband signals represented by the sample data of each frame read from the data storage unit 46 based on the selected reception delay pattern, and adds (phasing addition) the complex baseband signals after matching phases, thereby performing reception focusing processing (beam forming). By the reception focusing processing in the phasing addition unit 60, a baseband signal (acoustic-ray signal) in which ultrasound echoes are well focused is generated for each frame, that is, a so-called echo signal of each frame is generated.

The image processor 62 generates a B-mode image signal which is tomographic image information on a tissue within a subject to be examined based on the echo signal (acoustic-ray signal) of each frame generated by the phasing addition unit 60. The image processor 62 includes a band-pass filter, a high-frequency amplifier including a STC (Sensitivity Time Control) unit, a logarithmic amplifier, a luminance converter, and the like.

Here, the band-pass filter varies a pass band in accordance with a propagation time of an ultrasound echo to improve the S/N ratio. The STC unit of the high-frequency amplifier controls an amplification gain in accordance with the propagation time to correct attenuation of the echo signal (acoustic-ray signal) based on a distance in accordance with the depth of the reflection position of the ultrasound wave. The logarithmic amplifier amplifies the echo signal by limiting a variation range of the amplitude which varies over a wide range. The luminance converter converts the amplitude into luminance to thereby generate a B-mode image signal for each frame which is tomographic image information, and which makes the echo signal displayed as one luminance-modulated emission line.

The time-sequential frame image storage unit 66 is a memory that time-sequentially stores the B-mode image signals representing images of a plurality of frames as time-sequential frame images. The time-sequential frame image storage unit 66 is formed of a memory, a hard disk, or the like, similarly to the data storage unit 46.

The time-sequential frame differential image generator 68 calculates a difference between two time-sequential frame images (B-mode image signals) stored in the image storage unit 66 to thereby generate a differential image (differential image signal).

A preferred detailed configuration of the differential image generator 68 will be described later.

The puncture needle tip detector 70 which is the most characteristic portion of the first aspect of the invention performs a process of detecting a tip end from the differential image generated by the differential image generator 68. For example, the puncture needle tip detector 70 detects at least one tip candidate including a puncture needle tip using a difference in luminance of respective pixels of the differential image, highlights the detected tip candidates, and generates a highlighted tip image.

Figure 3:
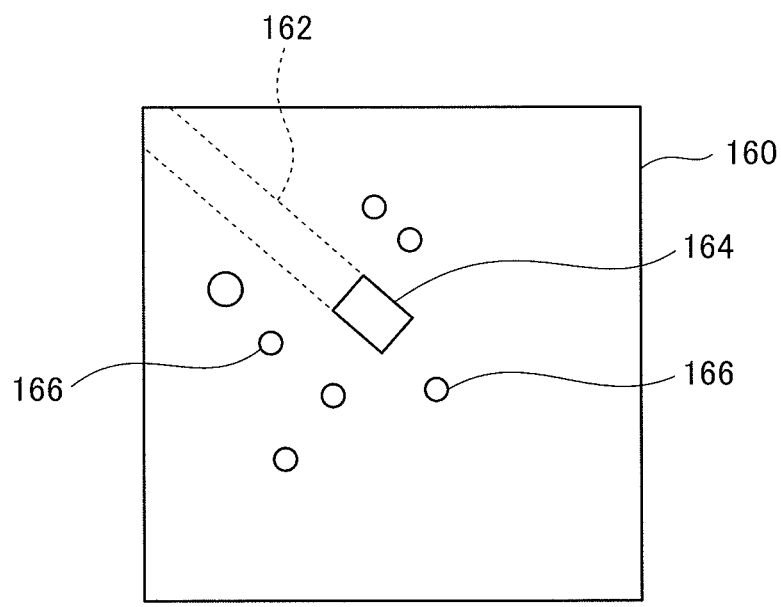
FIG. 3 is a view showing an example of a differential image obtained by a differential image generator of the combined image generator of the ultrasound diagnostic apparatus shown in FIG. 1.

In the tip detector 70, as shown in FIG. 3, when a puncture needle 162 which is inserted is generated in a differential image 160, since the amount of displacement of a tip end 164 of the puncture needle 162 is obtained as a difference, it is possible to detect only the tip end 164 which is the most important in the puncturing of the puncture needle 162. It is most preferable for the tip detector 70 to detect only one tip candidate 166 corresponding to the tip end 164 of the puncture needle 162. However, since the differential image 160 includes a movement of a puncture target or noise other than the displacement of the puncture needle 162, a plurality of tip candidates 166 are detected. Thus, as described above, it is not always possible to detect only one tip candidate corresponding to the tip end 164 of the puncture needle 162.

Therefore, in the present aspect of the invention, when the number of tip candidates detected by the tip detector 70 is one or a predetermined number and for example, six or less, it is preferable to color these tip candidates and/or increase the luminance thereof as a highlighting process to thereby generate a color and/or high-luminance tip image. When a lot of tip candidates, for example, exceeding six, are detected by the tip detector 70, it is preferable to eliminate tip candidates of low reliability to narrow the tip candidates down to one to six tip candidates. Naturally, it is most preferable to narrow to one tip candidate. Similarly, it is preferable to perform a highlighting process on the narrowed tip candidates to generate a color and/or high-luminance tip image.

The detailed configuration of the tip detector 70 will be described later.

The image combiner 72 combines the tip image (needle tip enhanced image) generated by the tip detector 70 with an ultrasound image which is the B-mode image generated by the image processor 62 to thereby generate a combined ultrasound image.

The combined ultrasound images (image signals) generated by the image combiner 72 are transmitted to the display controller 50.

In the diagnostic apparatus main body 14 of the ultrasound diagnostic apparatus 10 of the shown example, the display controller 50 includes the DSC for converting the combined ultrasound images (image signals) combined by the image combiner 72 into display image signals for display on the display unit 52. However, the invention is not limited to this. The image combiner 72 may include the DSC, and the DSC may convert (rasterize) the combined ultrasound images (image signals) combined by the image combiner 72 into image signals corresponding to a general television signal scanning format and perform necessary image processing such as gradation processing to thereby generate B-mode image signals for display on a monitor.

Moreover, the image processor 62 may include the DSC, and the DSC may convert (rasterize) the echo signals (acoustic-ray signals) corrected by the STC unit or the luminance-modulated B-mode image signals into image signals corresponding to a general television signal scanning format and perform necessary image processing such as gradation processing to thereby generate B-mode image signals for display on a monitor. In this case, if the display image signals are used for detecting the tip end portion of the puncture needle, the display controller 50 and the image combiner 72 may not include the DSC.

Next, the detailed configuration of the puncture needle tip detector 70 which is the most characteristic portion of the present aspect of the invention will be described.

As shown in FIG. 2, the puncture needle tip detector 70 includes a tip candidate detector 74, a tip candidate processor 76, a tip candidate storage unit 78, and a puncture needle information and condition storage unit (hereinafter referred to simply as an information storage unit) 80.

The tip candidate detector 74 performs a tip detection process on the differential image generated by the differential image generator 68 to detect at least one tip candidate including the puncture needle tip. The tip candidate detector 74 includes a candidate point extraction processor (hereinafter also referred to as an extraction processor) 82 and a tip candidate specifying processor (hereinafter also referred to as a specifying processor) 84.

As an example of the tip detection process, first, the candidate point extraction processor 82 extracts points having luminance difference values satisfying predetermined conditions based on a luminance difference or a luminance value of the differential image as tip candidate points of the puncture needle. For example, the candidate point extraction processor 82 performs binarization, filter processing, and LUT (lookup table) processing for gradation processing or the like to extract regions or portions (a collection of pixels) in which the luminance difference in relation to the luminance of neighboring portions is equal to or larger or smaller than a predetermined value, or regions of which the luminance values are equal to or larger or smaller than a predetermined value as the tip candidate points of the puncture needle.

In the extraction processor 82, it is preferable to select and extract the tip candidates of the puncture needle based on the density or size of the tip candidate points or regions detected in accordance with the luminance difference or the like of the differential image. Specifically, median filtering may be used, or alternatively, the sum of the luminance values of pixels near a predetermined point may be calculated, and locations having a large luminance sum or portions of which the luminance sum exceeds a predetermined threshold may be extracted as tip candidate points or detected as tip candidates.

Moreover, in the extraction processor 82, it is preferable to perform LUT processing after setting a tip candidate extraction region in advance by referencing the positions of tip candidates detected in the past, stored in the tip candidate storage unit 78. In particular, the extraction processor 82 may extract or detect regions of which the luminance difference is equal to or larger than a predetermined value from regions near a line that connects two or more tip candidates of the puncture needle detected in the past, as the tip candidate points of the puncture needle or the tip candidates.

By doing so, it is possible to find the tip candidate points or the tip candidates taking the advancing movement or direction of the puncture needle into consideration. Thus, it is possible to extract and detect the tip candidate points and the tip candidates more accurately.

When a plurality of tip candidate points of the puncture needle are extracted by the extraction processor 82, the tip candidate specifying processor 84 performs a process of eliminating tip candidate points of low reliability as one of the tip detection processes. For example, the tip candidate specifying processor 84 specifies only the central points of regions having a high correlation as tip candidates to thereby narrow the number of tip candidate points down to a predetermined number, for example, one to six, and most preferably to one, and specifies the narrowed tip candidate points as tip candidates to be detected.

Figure 4:
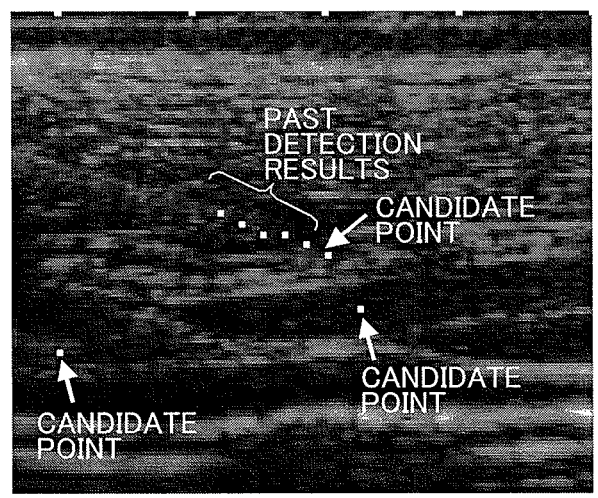
FIG. 4 is a view showing an example of an ultrasound image showing an insertion trajectory of a puncture needle.

As the process of eliminating tip candidate points of low reliability, when a plurality of tip candidate points remain after the LUT processing by the extraction processor 82, it is preferable for the specifying processor 84 to narrow the tip candidate points so as to include points of which the distance to the positions of a plurality of tip candidates detected in the past is minimized. That is, a plurality of past detection results for the tip candidates of the puncture needle may be stored in the tip candidate storage unit 78. For example, as shown in FIG. 4, candidate points among the presently detected tip candidate points, of which the distance to detection result points (tip candidates) of five frames is minimized, may be specified as present detection results. Such a method is effective when the specifying processor 84 narrows the tip candidate points when a plurality of tip candidate points are extracted in the extraction of simple tip candidate points by the extraction processor 82 as shown in FIG. 4.

When the number of tip candidate points of the puncture needle extracted by the extraction processor 82 is a predetermined number, for example, one to six, as described above, the specifying processor 84 may specify all the candidate points as tip candidates of the puncture needle to be detected, and may further narrow the candidate points until the number reaches a smaller number, and preferably one.

When the number of tip candidate points extracted by the extraction processor 82 is always smaller than a predetermined number of tip candidates to be detected by the tip candidate detector 74, for example, one to six, the specifying processor 84 may not be provided.

As the result of the LUT processing by the extraction processor 82, when it was not possible to extract any tip candidate point of the puncture needle, the tip candidates detected previously or in the past, stored in the tip candidate storage unit 78 may be extracted as the tip candidate points to be detected presently or detected as the tip candidates, or new tip candidate points or new tip candidates may be estimated from the tip candidates detected in the past. The tip candidate points extracted or estimated by the extraction processor 82 are specified by the specifying processor 84 as tip candidates to be detected presently. Moreover, the tip candidates themselves detected in the past or the tip candidates estimated may directly be specified by the specifying processor 84 as tip candidates to be detected presently.

In such a case, since it can be considered that the tip end was not moved due to the insertion of the puncture needle, it can be understood that the tip candidates detected previously or in the past can be used.

Moreover, in the tip candidate detector 74, even when it was not possible to detect optimal tip candidates in the present frame, past detection results stored in the tip candidate storage unit 78 may be displayed on the display unit 52. For example, when there are a plurality of past detection results, since it is possible to calculate the equation of a line and the insertion speed of the puncture needle, points predicted from these two factors may be displayed as tip candidates. Alternatively, points which were successfully detected at the last time by the tip candidate detector 74 may continue to be displayed as tip candidates as they were.

In this way, the tip candidate detector 74 detects a predetermined number of, for example, one to six, tip candidates.

In the invention, it is preferable for the tip candidate detector 74 to detect at least six tip candidates. This is because the present inventors have confirmed that when at least six tip candidates are detected, it is highly probable that the puncture needle tip is included within the six tip candidates.

In the above example, the extraction processor 82 and the specifying processor 84 perform binarization, filtering, and LUT processing such as gradation processing as a tip detection process. However, the invention is not limited to this. In order that the extraction processor 82 extracts the predetermined number of tip candidate points of the puncture needle, LUT processing such as gradation processing may be performed after binarization, and a predetermined number of tip candidate points may be selected in descending order of luminance difference.

Moreover, the LUT used for the LUT processing in the extraction processor 82 or the specifying processor 84 may be adjusted in accordance with one or both of the ultrasound images (B-mode images) generated by the image generator 64 and the differential images generated by the differential image generator 68. That is, in the LUT processing, it is preferable to use a tip enhancement filter which is weighted in the insertion direction of the puncture needle and has a size such that the puncture needle tip is included. Such a tip enhancement filter can be referred to as a filter that detects the movement of the puncture needle since it is applied to a differential image.

Examples of such a tip enhancement filter include a filter which has a step shape and uses pixels located in the insertion direction of the puncture needle in weighted addition and a filter which has a rectangular shape and performs weighted addition so that pixels located in the insertion direction of the puncture needle have a large filter coefficient.

Figure 5:
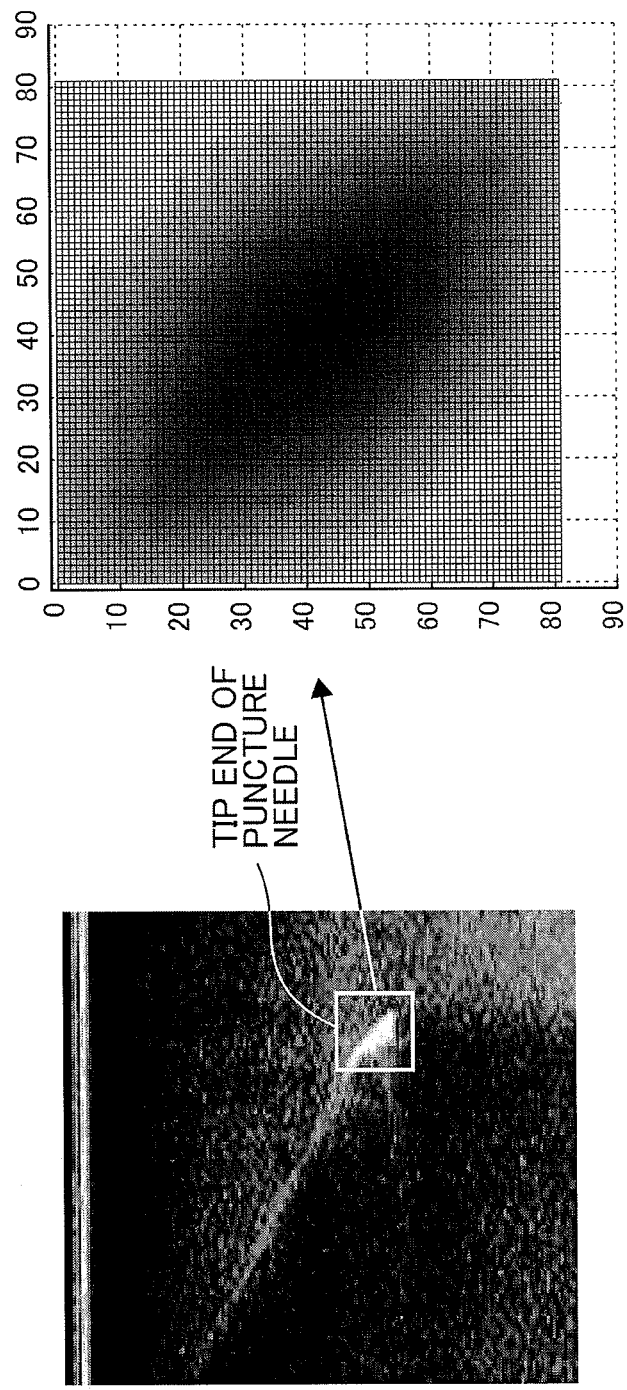
FIGS. 5A and 5B are views showing an example of a differential image used by the puncture needle tip detector shown in FIG. 2 and an example of a tip enhancement filter applied to the differential image, respectively.

Here, an example of a differential image including the image of the puncture needle tip and an example of a tip enhancement filter used when the tip detector 70 performs LUT processing on the differential image are shown in FIGS. 5A and 5B, respectively.

A tip enhancement filter having a size of 81×81 pixels shown in FIG. 5B is a rectangular filter which is weighted in the insertion direction of the puncture needle in the differential image shown in FIG. 5A, has a size such that the puncture needle tip is included, and performs weighted addition so that pixels located in the insertion direction have a large filter coefficient.

Such a tip enhancement filter is made up of an odd number of pixels in both vertical and horizontal directions so that a target pixel is located at the center, and the filter coefficients of respective pixels can be determined by applying a Gaussian function expressed by Equation 1 below. That is, the tip enhancement filter shown in FIG. 5B is a filter created by applying the Gaussian function expressed by Equation 1 below.

$$f(x, y) = \frac{1}{2\pi\sigma_x\sigma_y\sqrt{1-\rho_{xy}^2}} \exp\left(-\frac{1}{2(1-\rho_{xy}^2)}\left\{\frac{(x-\mu_x)^2}{\sigma_x^2} + \frac{(y-\mu_y)^2}{\sigma_y^2} - \frac{2\rho_{xy}(x-\mu_x)(y-\mu_y)}{\sigma_x\sigma_y}\right\}\right) \quad (1)$$

Here, $f(x,y)$ is a filter coefficient, $\mu_x$ and $\mu_y$ are averages in x and y directions, $\sigma_x$ and $\sigma_y$ are variances in x and y directions, and $\rho$ is a correlation value. When $\mu_x=\mu_y=0$, $\sigma_x^2=\sigma_y^2=40$, and $\rho=0.9$, it is possible to create a filter having the size of 81×81 pixels schematically shown in FIG. 5B. FIG. 5B shows the magnitudes of the filter coefficients as the thickness of density. In this way, it is possible to create filter coefficients so that pixels located in the insertion direction of the puncture needle have a large filter coefficient.

In FIG. 5B, the filter coefficient increases as it approaches the center, and the filter coefficients on an ellipse concentric about the central pixel are the same. In FIG. 5B, for better understanding of the invention, the concentric ellipse is depicted with a boundary, although there is actually no boundary as shown. The longitudinal direction of the ellipse is identical to the insertion direction of the puncture needle. That is, by increasing the filter coefficients located in the insertion direction of the puncture needle, weighted addition is performed so that the pixels located at the position where the possibility of presence of the puncture needle is high have a large filter coefficient.

The tip enhancement filter, having an aspect ratio corresponding to the insertion angle, created in this way is stored in the information storage unit 80.

In the present aspect of the invention, a tip enhancement filter to be used is determined in accordance with the insertion angle and stored in the information storage unit 80. The tip candidate detector 74 can detect tip candidates which are candidates of high reliability for the puncture needle tip by performing a tip enhancement processing of performing weighted addition on the differential image with neighboring pixels using the tip enhancement filter stored in the information storage unit 80.

When calculating the density or size of a region detected in the differential image, a filter having such a size that the puncture needle tip is included like the tip enhancement filter shown in FIG. 5B can be created in the following way.

A plurality of filter sizes in which the puncture needle tip is included may be prepared in the manner of "Large," "Medium," and "Small" in accordance with the thickness of the puncture needle, for example, and a plurality of sizes may be prepared between the angles of 10° and 60° in the manner of "10°," "30°," and "60°" in accordance with the insertion angle of the puncture needle. Moreover, the size may be determined based on the size (G) of the puncture needle, the purpose of puncture (FNA (Fine Needle Aspiration Cytology), CNB (Core Needle Biopsy), RFA (Radio-Frequency Ablation), and the like), and puncture information such as an insertion angle.

Moreover, as described above, weights of the filter may use a Gaussian function or the like. In this case, the proportions of weights in averaging, variance, correlation, and the like may be prepared as parameters which can be changed by a user.

Moreover, the size of the filter and the weights of the weighted filter may be changed by a user selecting in advance on a setting screen, or may be changed during scanning of the ultrasound probe 12 by allocating a function to a function key or the like.

Examples of the tip enhancement filter used in the present aspect of the invention include various puncture tool enhancement filters which are used in a puncture tool enhancement processing applied to an ultrasound image generation apparatus and an ultrasound image generation method of the third aspect of the invention described later.

Moreover, when the extraction processor 82 or the specifying processor 84 performs LUT processing to extract the tip candidate points of the puncture needle or detect the tip candidates, a region of the differential image, which is located around the tip candidate points and has a size obtained by applying the tip enhancement filter may be colored. By doing so, it is possible to detect tip candidate points within the colored region as tip candidates, and to increase the reliability or probability of the detected tip candidates being the puncture needle tip.

Furthermore, preferably, the extraction processor 82 and/or the specifying processor 84 of the tip candidate detector 74 searches a region of the differential image based on a frame displayed on the display unit 52, located near the tip candidates of the puncture needle detected at a point in time earlier than the displayed frame, preferably a region near a line connecting tip candidates of the puncture needle detected at two points in time earlier than the displayed frame to thereby detect tip candidates of the puncture needle from the differential image based on the displayed frame. By doing so, it is possible to detect tip candidates having a high probability of being the puncture needle tip taking the movement, or displacement, of the puncture needle inserted into a target site into consideration.

The tip candidate processor 76 performs a process of highlighting a predetermined number of tip candidates, that is to say, at least one tip candidate detected by the tip candidate detector 74 or the coordinates thereof to generate the image of the highlighted tip candidate of the puncture needle, namely a tip image in which the tip candidate of the puncture needle is highlighted, in order to make the image easily identified by an operator when it is displayed on the display unit 52.

In the tip candidate processor 76, it is preferable to color the tip candidate of the puncture needle detected by the tip candidate detector 74 to generate a color tip image for color display as the highlighting process. Alternatively, it is preferable to increase the luminance of the tip candidate to generate a high-luminance tip image. It is also preferable to increase the luminance after coloring the tip candidate to generate a high-luminance color tip image.

In addition, although the number of tip candidates or coordinates thereof which are colored or brightened is preferably one, the number may be two or more, and the tip candidates detected in the past or the coordinates thereof may be used. Moreover, as shown in FIG. 4, the tip candidate processor 76 may highlight and display the tip image of the puncture needle detected in the past on the display unit 52 in a superimposed manner so that the trajectory of the puncture needle is displayed.

The colored or brightened region of the tip candidate of the puncture needle or the coordinates thereof may be the region of the tip candidate itself, and may be an optional region of the coordinates of the tip candidate, for example, a rectangular, elliptical, circular, or square region including the coordinates. Moreover, the size of the region can be set in advance, and may be changed during scanning of the ultrasound probe 12 by allocating a function to a function key or the like.

The colored or brightened region may be weighted by the tip enhancement filter used when the tip candidate detector 74 detects the tip candidates.

Here, preferably, the tip candidate detector 74 determines the positive/negative sign of the luminance difference of the differential image, and the tip candidate processor 76 highlights the tip candidate of the puncture needle detected by the tip candidate detector 74 in accordance with the positive/negative sign of the luminance difference of the differential image determined by the tip candidate detector 74. More preferably, the tip candidate processor 76 changes the color and luminance used for highlighting the tip candidate of the puncture needle detected by the tip candidate detector 74. In this way, by displaying the highlighted tip candidate on the display unit 52 by changing the color and luminance thereof, it is possible to display the puncture needle tip so as to be visible as it is inserted into a target site when the luminance difference of the differential image is positive, for example.

Moreover, it is possible to display the puncture needle tip so as to be visible as it is pulled out when the luminance difference is negative.

Moreover, the tip candidate detector 74 may not determine the positive/negative sign of the luminance difference of the differential image, but the tip candidate processor 76 may generate a color tip image which is colored or brightened based on the absolute value of the luminance difference and display the tip image on the display unit 52.

The tip candidate storage unit 78 is a storage unit which is formed of a memory, a hard disk, or the like and stores the tip candidates (the positions (coordinates) or sizes thereof) detected by the tip candidate detector 74. The tip candidate storage unit 78 may store a plurality of past tip candidates.

The tip candidate storage unit 78 outputs the plurality of past tip candidates stored therein to the extraction processor 82 and the specifying processor 84 of the tip candidate detector 74 in order to allow them to be used for the detection in the tip candidate detector 74 and outputs the same to the tip candidate processor 76 in order to allow them to be used for the highlighting process in the tip candidate processor 76 or the display on the display unit 52.

The information storage unit 80 is a storage unit which is formed of a memory, a hard disk, or the like and stores information on the puncture needle, detection conditions for detecting the tip candidates in the tip candidate detector 74, processing conditions for the detection, processing conditions for the highlighting process in the tip candidate processor 76, and the like. Here, the information on the puncture needle may be the kind, the thickness, the insertion position (the position where the puncture needle is inserted into a patient), the insertion angle (the angle at which the puncture needle is inserted into a patient), and the insertion path of the puncture needle, a puncture target (target object or site), and the like. Moreover, specifically, the detection and processing conditions include the extraction conditions of the tip candidate points extracted by the tip candidate detector 74, such as the magnitude of the luminance difference or luminance value of the differential image, the threshold of the density or size of extracted points, as well as the type, size, and weighting conditions of various LUTs and filters including the tip enhancement filter used for extraction, and such processing conditions as the contents of the tip candidate highlighting process such as the coloring and brightening of the tip candidates in the tip candidate processor 76, and the size and shape of the target region of the tip candidate.

The information storage unit 80 acquires and stores the information on the puncture needle and the detection and processing conditions for the tip candidates through the main body controller 54 in accordance with the input or the like on the operation unit 56 from the user and outputs the information and conditions stored therein to the extraction processor 82 and the specifying processor 84 of the tip candidate detector 74 and the tip candidate processor 76.

The tip detector 70 basically has the configuration described hereinabove.

Next, a preferred configuration of the differential image generator 68 shown in FIG. 1 will be described.

Figure 6:
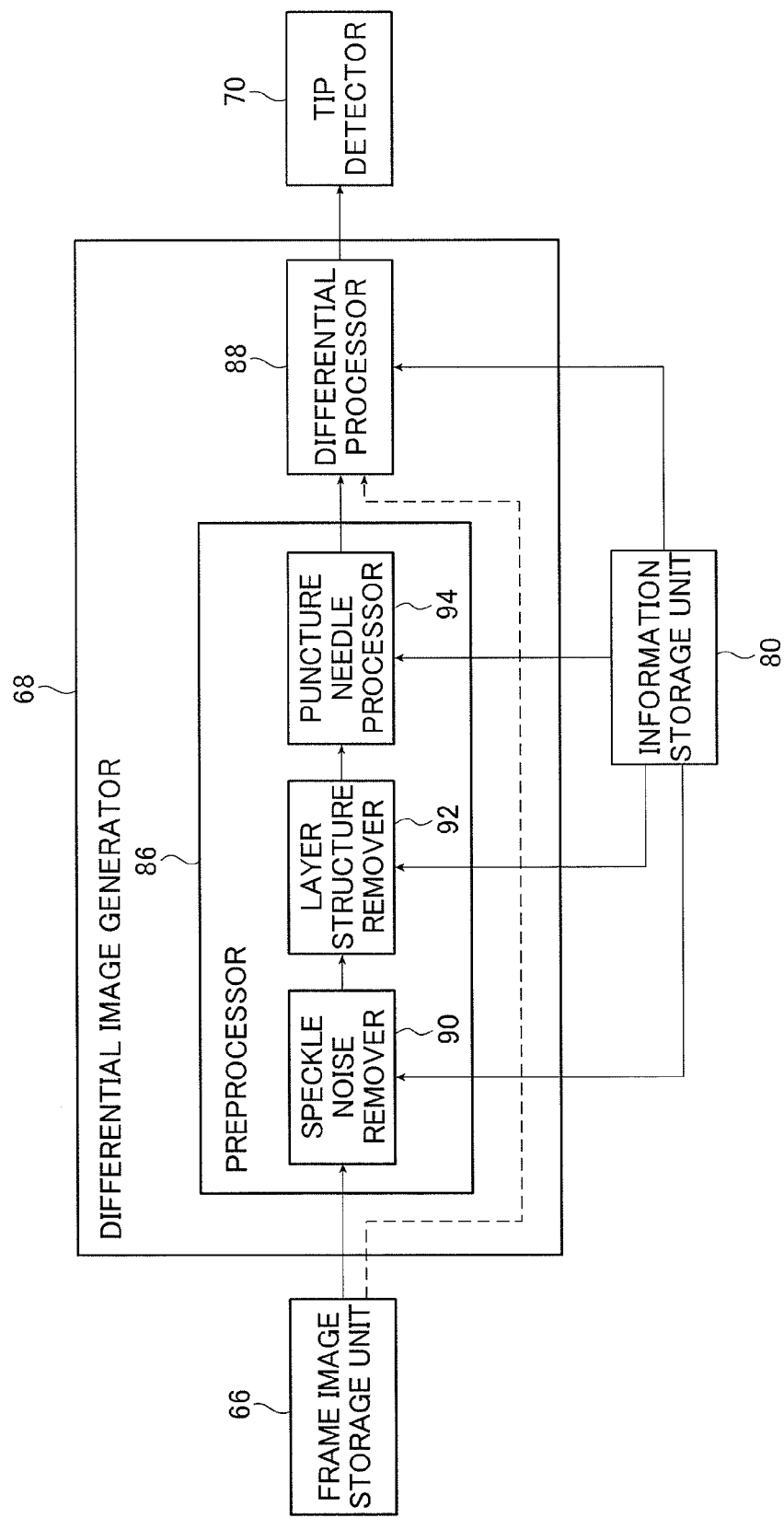
FIG. 6 is a block diagram showing an example of a time-sequential frame differential image generator of the combined image generator shown in FIG. 1.

FIG. 6 is a block diagram showing an example of the time-sequential frame differential image generator of the combined image generator shown in FIG. 1.

As shown in FIG. 6, the differential image generator 68 includes a preprocessor 86 and a differential processor 88. The preprocessor 86 includes a speckle noise remover 90, a layer structure remover 92, and a puncture needle processor 94.

The preprocessor 86 performs preprocessing on B-mode image signal (frame image) of at least one frame out of two time-sequential frames subjected to differential processing in order to increase the reliability of the detection of a puncture needle tip in a differential image before the generation of the differential image between the B-mode image signals of two time-sequential frames, generated by the image generator 64 and stored in the frame image storage unit 66. Examples of the preprocessing include a process of removing noise or a layer structure, a puncture needle enhancement processing, and a puncture needle image connecting process. The signal processing such as the puncture needle enhancement processing and the puncture needle image connecting process is performed on the B-mode image signal after noise removal in order to make the puncture needle clearly visible.

The preprocessor 86 preferably includes all of the speckle noise remover 90, the layer structure remover 92, and the puncture needle processor 94, but may include at least one of them.

The differential processor 88 calculates the difference between the B-mode image signals (images) of two time-sequential frames, in which speckle noise and a layer structure are removed, to thereby generate a differential image (differential image signal).

Here, since the insertion speed of the puncture needle varies depending on the technique or the like of an examiner or an operator, the differential processor 88 preferably has a function of adjusting a time difference between the two time-sequential frames used for creating the differential image so that the frame interval of the two time-sequential frames can be optionally set. Moreover, it is preferable to use a plurality of past frames two frames or more before when creating the differential image. The differential image (pixel signal) may include the absolute value of the difference value.

The differential image generator 68 preferably includes both the preprocessor 86 and the differential processor 88, but may not include the preprocessor 86 if it includes the differential processor 88.

As preprocessing of the differential processing on the B-mode image signals (frame images) of two time-sequential frames generated by the image generator 64 and stored in the image storage unit 66, the speckle noise remover 90 performs signal processing for reducing a speckle pattern in the B-mode image signals to thereby remove speckle noise. Although a median filter, for example, is preferably applied to the process of removing speckle noise, a spatial compounding method, a frequency compounding method, morphology processing, or the like may be applied.

The layer structure remover 92 performs a layer structure removal processing on the B-mode image signals in which speckle noise is removed by the speckle noise remover 90 to thereby remove a bright line extending in the direction of the puncture needle. For example, CFAR (Constant False Alarm Rate) processing and MIP (Maximum Intensity Projection) processing are performed. As for the CFAR processing, a method disclosed in JP 2006-305337 A can be used.

In this way, by the layer structure removal processing by the layer structure remover 92, connected portions other than the puncture needle can be removed in later signal processing by the puncture needle processor 94.

Moreover, in order to make the puncture needle clearly visible in a frame image, the puncture needle processor 94 performs signal processing of causing defocusing in the direction of the puncture needle to make the puncture needle continuous or signal processing of making the puncture needle continue from its feature points. Thus, the puncture needle processor 94 includes at least one of a puncture needle enhancement processor 94*a* (see FIG. 7) that performs signal processing of causing defocusing in the direction of the puncture needle to make the puncture needle continuous and a puncture needle connection processor 94*b* (see FIG. 9) that performs signal processing of making the puncture needle continue from its feature points.

Figure 7:
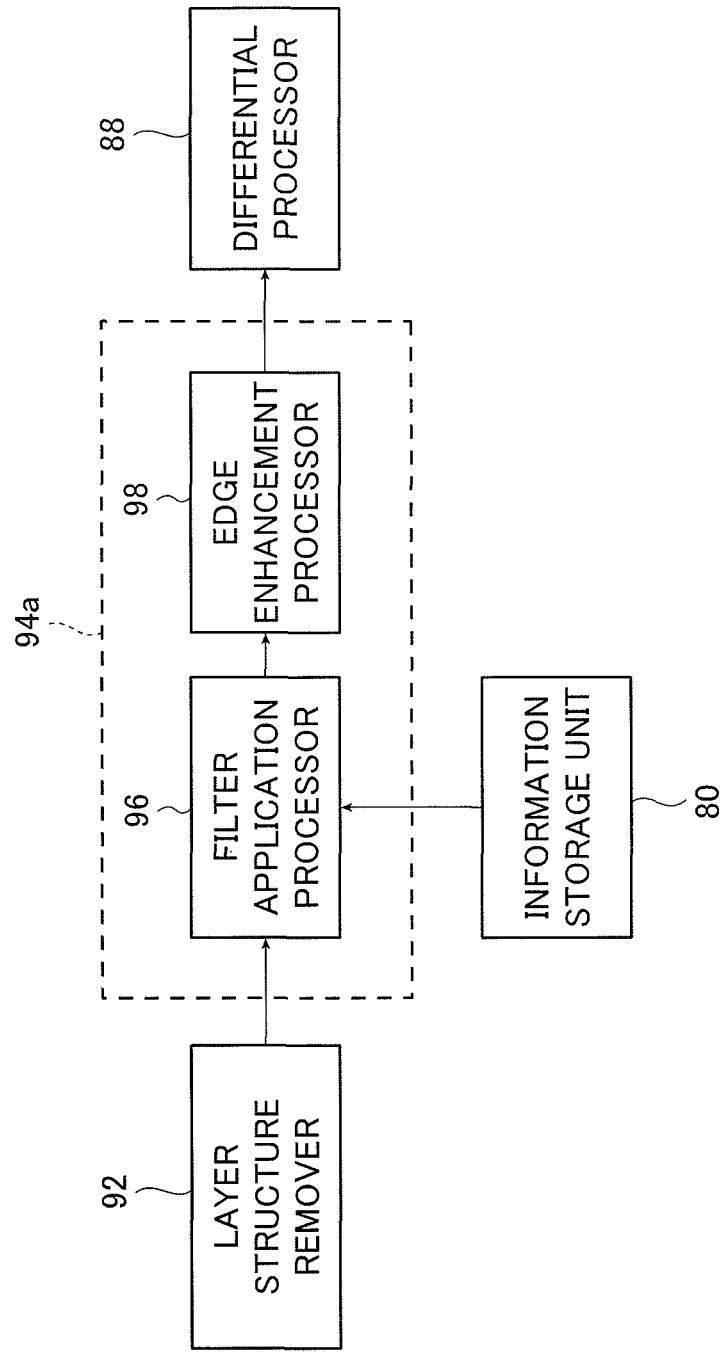
FIG. 7 is a functional block diagram showing an example of a puncture needle processor of the time-sequential frame differential image generator shown in FIG. 6.

FIG. 7 shows a puncture needle enhancement processor which is an example of the puncture needle processor of the time-sequential frame differential image generator shown in FIG. 6.

The puncture needle enhancement processor 94*a* shown in FIG. 7 includes a filter application processor 96 and an edge enhancement processor 98.

The filter application processor 96 applies a defocus filter to the B-mode image signal in which noise such as speckle noise or a layer structure is removed by the layer structure remover 92 or the speckle noise remover 90. That is, the filter application processor 96 specifies a defocus filter to be used based on the insertion angle stored in the information storage unit 80 and reads the specified defocus filter from the information storage unit 80. For example, when the insertion angle is 10°, the filter application processor 96 reads a defocus filter for the insertion angle of 10° and applies the read defocus filter to the B-mode image data after noise removal. Since the defocus filter used herein is a filter corresponding to the insertion angle of the puncture needle, it is possible to defocus the image in the insertion direction of the puncture needle to make a discontinuous puncture needle image continuous.

The edge enhancement processor 98 performs a process of enhancing the edges of the B-mode image with respect to the B-mode image data to which the defocus filter has been applied. After that, a 1D edge enhancement processing may be performed in the vertical direction to the puncture needle to thereby enhance the edges of the puncture needle. Before outputting to the differential processor 88, the edge-enhanced B-mode image (image data) which has been made continuous in the insertion direction of the puncture needle may be superimposed on the original B-mode image (image data) to thereby generate a combined frame image (image data). In this way, a frame image in which the whole image of the puncture needle within the tissue is clearly visible can be output to the differential processor 88.

Similarly to the tip enhancement filter used by the tip detector 70, examples of the defocus filter used by the filter application processor 96 for the signal processing of causing defocusing in the direction of the puncture needle include a filter which has a step shape and uses pixels located in the insertion direction of the puncture needle in weighted addition and a filter which has a rectangular shape and performs weighted addition so that pixels located in the insertion direction of the puncture needle have a large filter coefficient. Here, when such a filter is used as the defocus filter, it is necessary to create the tip enhancement filter used by the tip detector 70 as a puncture needle enhancement filter which is weighted in the insertion direction of the puncture needle in the frame image and has a size such that the puncture needle is included.

That is, in the filter application processor 96, such a filter as shown in FIG. 5B, which has a rectangular shape and performs weighted addition so that pixels located in the insertion direction of the puncture needle have a large filter coefficient, can be used as the defocus filter.

Figure 8C:
FIGS. 8A, 8B, and 8C are views showing an example of one frame of ultrasound image processed by a filter application processor of the puncture needle processor shown in FIG. 7, an example of a puncture needle enhancement filter applied, and an example of a puncture needle enhanced ultrasound image after processing, respectively.
Figure 8B:
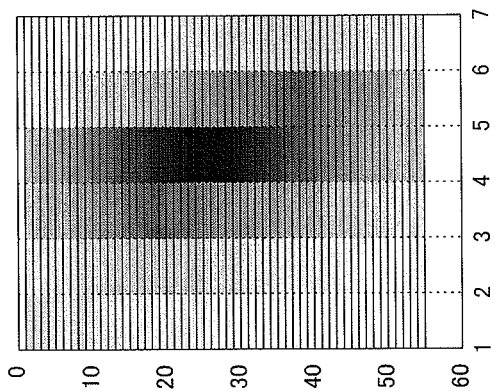
Figure 8A:
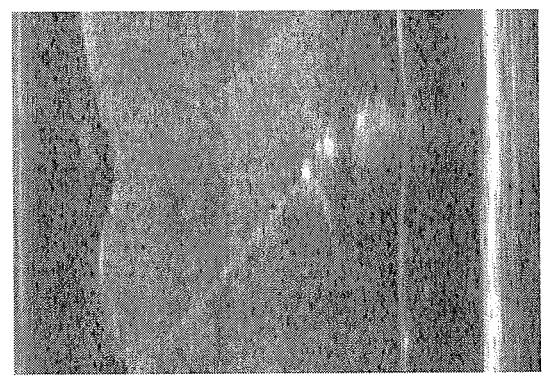

An example in which such a puncture needle enhancement filter is applied to one frame of B-mode image (frame image) so as to correspond to the insertion direction or the insertion angle of the puncture needle is shown in FIGS. 8A to 8C.

FIGS. 8A, 8B, and 8C show a frame image (B-mode image), a puncture needle enhancement filter, and a puncture needle-enhanced image, respectively.

Here, the frame image shown in FIG. 8A is one frame of ultrasound image (B-mode image) which is not subjected yet to the puncture needle enhancement processing performed by the filter application processor 96 of the puncture needle processor 94*a* shown in FIG. 7.

The puncture needle enhancement filter shown in FIG. 8B is a puncture needle enhancement filter which has a size of 55×7 pixels, applied to the one-frame image shown in FIG. 8A.

The puncture needle-enhanced image shown in FIG. 8C is a puncture needle enhanced ultrasound image obtained by applying the puncture needle enhancement filter to the frame image so as to correspond to the insertion direction or the insertion angle of the puncture needle, and is an image in which the B-mode image before the puncture needle enhancement processing is defocused in the direction of the insertion angle. Thus, as shown in FIG. 8C, the puncture needle is displayed in a continuous manner in the obtained puncture needle-enhanced image.

Here, in FIGS. 8A and 8C, for better understanding of the effect of the puncture needle enhancement filtering, speckle noise removal processing, layer structure removal processing, and edge enhancement processing were not performed.

As above, the puncture needle enhancement filter shown in FIG. 8B is a puncture needle enhancement filter which is weighted in the insertion direction of the puncture needle in one-frame image shown in FIG. 8A, and has a size of 55×7 pixels such that the puncture needle is included. The puncture needle enhancement filter shown in FIG. 8B can generate filter coefficients used in the puncture needle enhancement filter by linearly interpolating the tip enhancement filter shown in FIG. 5B so as to have the size of the puncture needle enhancement filter. That is, by linearly interpolating the filter having the size of 81×81 pixels shown in FIG. 5B, it is possible to create the puncture needle enhancement filter having the size of 55×7 pixels shown in FIG. 8B. The puncture needle enhancement filter having the size of 55×7 pixels obtained in this way is a puncture needle enhancement filter used if the insertion angle is 10°. The aspect ratio of the linear interpolation is determined by the insertion angle. In this puncture needle enhancement filter, the filter coefficient is the largest at the center, with the magnitude of the filter coefficient widely varying along the insertion direction of the puncture needle. A target pixel at the center is subjected to weighted addition using the 55×7 pixels around the target pixel. The values of the respective pixels are multiplied by the filter coefficients of the puncture needle enhancement filter to perform weighted addition, whereby the value of the target pixel is obtained. The puncture needle enhancement filter created in this way, having the aspect ratio corresponding to the insertion angle is stored in the information storage unit 80.

In the present embodiment, the puncture needle enhancement filter to be used is determined based on the insertion angle, and the puncture needle enhancement processing of performing weighted addition with neighboring pixels is performed on all pixels using the determined puncture needle enhancement filter, whereby an image in which the puncture needle is enhanced can be generated.

In this example, although a case of converting into a size of 55×7 pixels like the puncture needle enhancement filter shown in FIG. 8B has been described, instead of this, a puncture needle enhancement filter shown in FIG. 14D described later may be used, for example. In puncture needle enhancement filters having different sizes like the puncture needle enhancement filter having the size of 15×27 pixels shown in FIG. 14D, filter coefficients corresponding to the sizes of the respective puncture needle enhancement filters can be generated by linearly interpolating the base filter having the size of 81×81 pixels shown in FIG. 5B. The puncture needle enhancement filter shown in FIG. 14D, having the size of 15×27 pixels obtained in this way is also a puncture needle enhancement filter used if the insertion angle is 10° like the puncture needle enhancement filter shown in FIG. 8B, having the size of 55×7 pixels. The puncture needle enhancement filter created in this way, having the aspect ratio corresponding to the insertion angle is stored in the information storage unit 80.

A defocus filter such as the puncture needle enhancement filter preferably has a size such that the discontinuance interval of the puncture needle is included. A plurality of sizes of the defocus filter may be prepared in the manner of "Large," "Medium," and "Small" in accordance with the thickness of the puncture needle, for example, and a plurality of sizes may be prepared between the angles of 10° and 60° in the manner of "10°," "30°," and "60°" in accordance with the insertion angle of the puncture needle. Moreover, the size may be determined based on the size (G) of the puncture needle, the purpose of the puncture (FNA, CNB, RFA, and the like), and puncture information such as an insertion angle.

Moreover, a Gaussian filter or the like may be used as a weighting filter used for the signal processing of causing defocusing in the direction of the puncture needle. In this case, the proportions of weights in averaging, variance, correlation, and the like may be prepared as parameters which can be changed by a user.

Moreover, the size of the defocus filter and the weights of the weighting filter may be changed by a user selecting in advance on a setting screen, or may be changed during scanning of the ultrasound probe 12 by allocating a function to a function key or the like.

Examples of the defocus filter include various puncture tool enhancement filters which are used in a puncture tool enhancement processing applied to an ultrasound image generation apparatus and an ultrasound image generation method of the third aspect of the invention described later.

Examples of the signal processing by the filter application processor 96 causing defocusing in the direction of the puncture needle include a puncture needle enhancement processing which uses a puncture needle enhancement filter as the defocus filter. For example, a puncture tool enhancement processing applied to an ultrasound image generation apparatus and an ultrasound image generation method of the third aspect of the invention described later can be applied.

That is, a puncture tool enhancement filter which has a step shape and uses pixels located in the insertion direction of the puncture needle in weighted addition can be used as the defocus filter. That is, a puncture needle enhancement filter that performs weighted addition between the value (image data) of a pixel (hereinafter referred to as a target pixel) subjected to the puncture needle enhancement processing and the value (image data) of a specific pixel neighboring the target pixel can be used. In this case, the filter application processor 96 sequentially changes the position of the target pixel and performs the puncture needle enhancement processing on the image data of all pixels in the B-mode image using the puncture needle enhancement filter determined based on the insertion angle.

Examples of such a puncture needle enhancement filter include a filter in which a plurality of lines of filter elements are connected in a step shape while shifting the lines in accordance with the insertion angle, a filter element at the center or almost at the center of the connected filter element lines is used as a target pixel, and the filter coefficients of pixels increase or decrease as the pixels are away from the target pixel.

The filter coefficient of such a puncture needle enhancement filter is generated using a Gaussian filter expressed by Equation 2 below.

$$f(x) = \frac{1}{\sqrt{2\pi}\,\sigma} \exp\left(-\frac{(x-\mu)^2}{2\sigma^2}\right) \qquad (2)$$

Here, $\mu$ is an average, $\sigma^2$ is a variance, and x represents the position of a pixel in the vertical direction of the drawing when a central element is at 0. For example, $x=-1$ and $x=1$ correspond to the positions of adjacent pixels on the front/rear or left/right sides of the central pixel. In this way, by determining the filter coefficients of respective pixels using the Gaussian filter, it is possible to perform weighted addition so that the pixels located closer to the target pixel have a larger filter coefficient.

Figure 9:
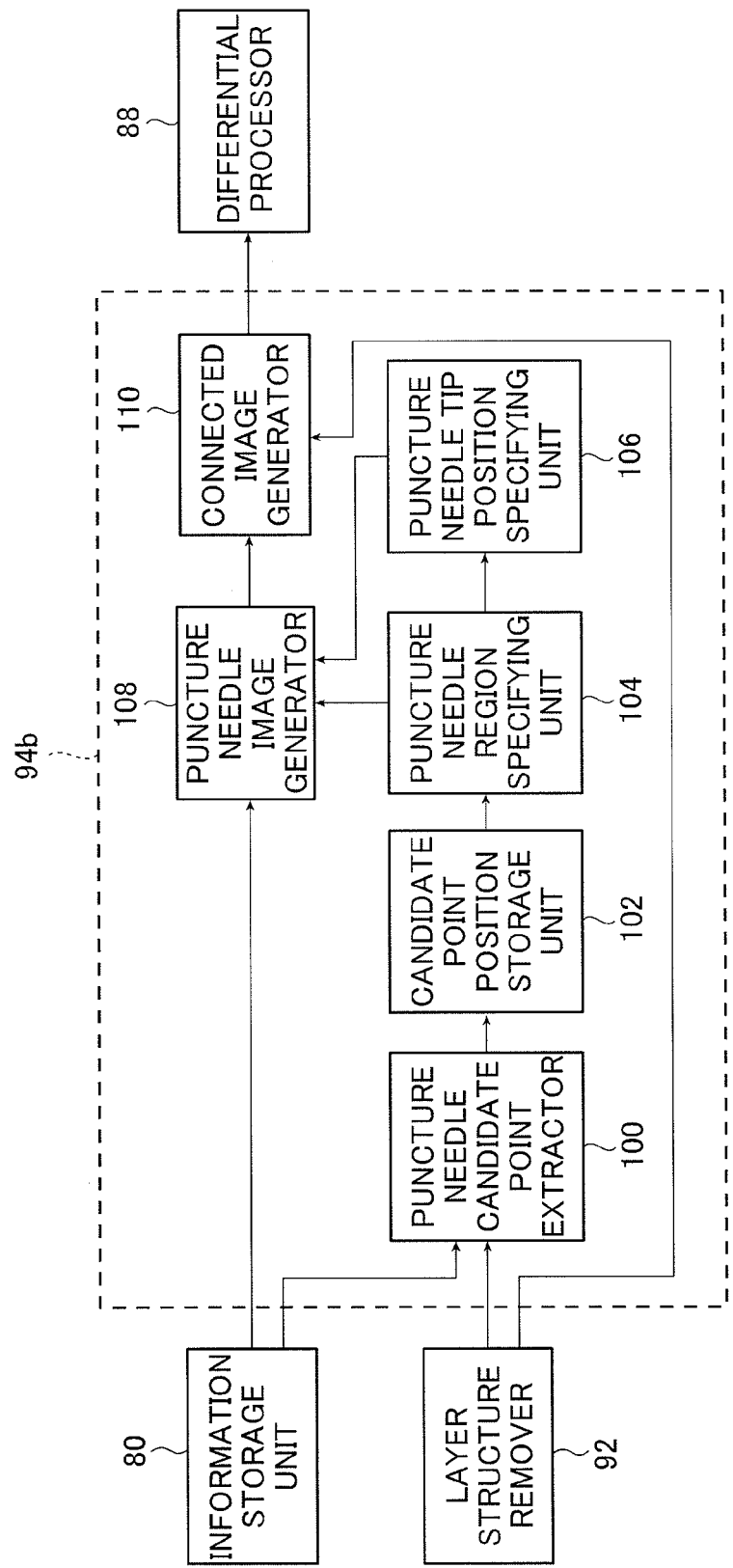
FIG. 9 is a functional block diagram showing another example of the puncture needle processor of the time-sequential frame differential image generator shown in FIG. 6.

FIG. 9 shows a puncture needle connection processor which is an example of the puncture needle processor of the time-sequential frame differential image generator shown in FIG. 6.

The puncture needle connection processor 94b shown in FIG. 9 performs signal processing of making the puncture needle continue from its feature points. Examples of such signal processing include a process of displaying a line using the feature points of the puncture needle through Hough transform or the like, a processing of fitting a line using the feature points of the puncture needle through a minimum mean square error method, and a process of storing the position coordinates of the feature points indicating the puncture needle tip in a memory for a certain period and connecting all the points by a line or a curve.

As shown in FIG. 9, the puncture needle connection processor 94b includes a puncture needle candidate point extractor 100, a candidate point position storage unit 102, a puncture needle region specifying unit 104, a puncture needle tip position specifying unit 106, a puncture needle image generator 108, and a puncture needle connected image generator 110.

The puncture needle candidate point extractor (hereinafter referred to as a candidate point extractor) 100 extracts needle candidate points as the feature points of the puncture needle using the information on the puncture needle stored in the information storage unit 80 and the B-mode image data in which the speckle noise or noise such as a layer structure is removed by the layer structure remover 92 and the speckle noise remover 90. Specifically, the candidate point extractor 100 performs threshold processing on the B-mode image data using an edge extraction filter to thereby create edge image data and extracts candidate points of the puncture needle from the edge image data as the feature points on the puncture needle. Since the puncture needle has a smooth surface, and scattering of ultrasound waves barely occurs, the puncture needle is displayed in the B-mode image in a discontinuous manner. Thus, by performing the threshold processing on the B-mode image data where the puncture needle is present, it is possible to extract feature points indicating parts of the discontinuous puncture needle. The time interval of extracting the feature points of the puncture needle can be changed by the user. Since high-luminance points originating from tissues or the like other than the puncture needle are also present in the B-mode image, the feature points extracted by the threshold processing are not limited to those originating from the puncture needle. The feature points of the puncture needle originating from tissues or the like become noise when specifying the position of the puncture needle based on the edge image.

The candidate point position storage unit (hereinafter referred to as a position storage unit) 102 stores the positions of all feature points (candidate points) of the puncture needle extracted by the candidate point extractor 100 and outputs the positions of the puncture needle feature points to the puncture needle region specifying unit (hereinafter referred to as a region specifying unit) 104.

The region specifying unit 104 generates a line (puncture needle candidate line) indicating the puncture needle and an extension line of the puncture needle based on the distribution of a plurality of puncture needle feature points stored in the position storage unit 102. The region specifying unit 104 specifies a region including the generated line as a region where the puncture needle is present.

The puncture needle tip position specifying unit (hereinafter referred to as a position specifying unit) 106 specifies the tip position of the puncture needle based on luminance information of the region which is specified by the region specifying unit 104 to be a region where the puncture needle is highly likely to be present and outputs the specified tip position to the puncture needle image generator 108.

The puncture needle image generator 108 generates an image representing the puncture needle based on the line indicating the puncture needle and the extension line of the puncture needle generated by the region specifying unit 104 and the tip position of the puncture needle specified by the position specifying unit 106 and outputs the image to the puncture needle connected image generator (hereinafter referred to as a connected image generator) 110. The image representing the puncture needle can be displayed in various modes as selected by the user. For example, the puncture needle may be displayed in a line, the outline of the puncture needle may be displayed, and the puncture needle may be displayed as a collection of dots. Here, when displaying the outline of the puncture needle, the outline of the puncture needle is generated by reading the puncture needle information from the information storage unit 80. Moreover, the luminance or the like representing the puncture needle can be set by the user. For example, the luminance of the image representing the puncture needle may be a favorite luminance of the user and may be the same luminance as the luminance of a portion which is considered to be the puncture needle in the B-mode image.

The connected image generator 110 generates combined B-mode image data in which the image representing the continuous puncture needle and generated by the puncture needle image generator 108 is superimposed on the B-mode image data output from the layer structure remover 92. The connected image generator 110 outputs the combined B-mode image data to the differential processor 88.

Figure 10:
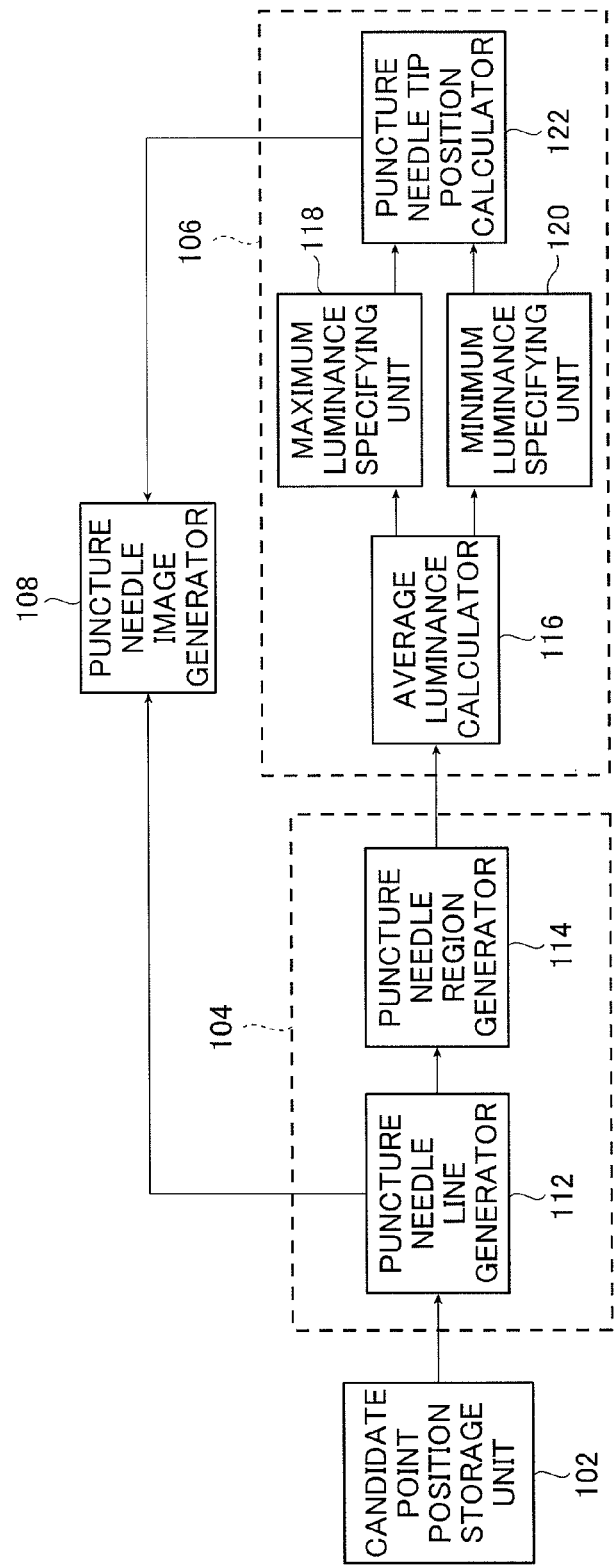
FIG. 10 is a functional block diagram showing a detailed configuration of a puncture needle region specifying unit and a puncture needle tip position specifying unit of the puncture needle processor shown in FIG. 9.

FIG. 10 is a functional block diagram showing a more detailed configuration of the puncture needle region specifying unit 104 and the puncture needle tip position specifying unit 106 as shown in FIG. 9.

The region specifying unit 104 includes a puncture needle line generator 112 and a puncture needle region generator 114.

The puncture needle line generator (hereinafter referred to as a line generator) 112 performs a Hough transform on the puncture needle feature points distributed within the B-mode image output from the position storage unit 102 to thereby generate a puncture needle candidate line. The puncture needle candidate line is a line that passes the largest number of puncture needle feature points. The line generator 112 outputs the position coordinates of points located on the generated puncture needle candidate line to the puncture needle region generator (hereinafter referred to as a region generator) 114.

The region generator 114 expands the puncture needle candidate line generated by the line generator 112 to a predetermined width and specifies a region included in the puncture needle candidate line as a region (puncture needle presence region) where the puncture needle is present. The region generator 114 outputs the position coordinates of points included in the specified puncture needle presence region to the position specifying unit 106.

The position specifying unit 106 includes an average luminance calculator 116, a maximum luminance specifying unit 118, a minimum luminance specifying unit 120, and a puncture needle tip position calculator 122.

By referring to FIGS. 11A to 11D and FIGS. 12A and 12B, a method of calculating the puncture needle tip position from a B-mode image and a method of generating an image representing the puncture needle will be described in detail. Moreover, the functions of respective constituent elements of the position specifying unit 106 will be described.

Figure 11A:
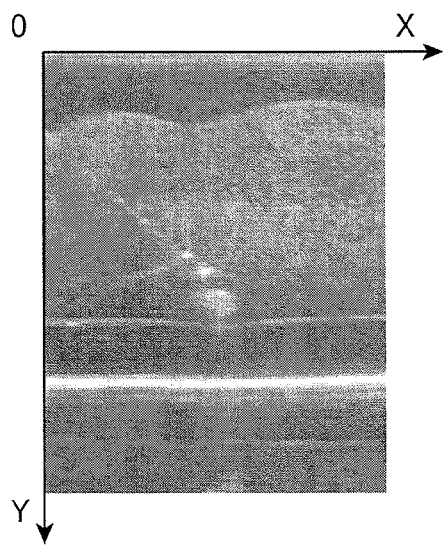
FIG. 11A shows an example of a B-mode image of the invention.

In FIG. 11A, a case where an image is positioned in an XY orthogonal coordinate system in which the top left corner of a B-mode image is at the origin, a horizontal axis extending from the top left corner to the top right corner is an X axis, and a vertical axis extending from the top left corner to the bottom left corner is a Y axis will be considered. A direction from the top left corner of the B-mode image to the top right corner is defined as the positive direction of the X axis, and a direction from the top left corner of the B-mode image to the bottom left corner is defined as the positive direction of the Y axis. In the following description, the same definition of the XY orthogonal coordinate system in relation to an image will be applied unless otherwise defined.

FIG. 11A shows a B-mode image of a subject to be examined including a puncture needle.

The puncture needle in FIG. 11A is displayed in a discontinuous manner, and it is difficult to understand the accurate position of the puncture needle. Thus, first, the puncture needle connection processor 94b specifies a region where the puncture needle is highly likely to be present from the B-mode image as shown in FIG. 11A and specifies the tip position of the puncture needle from the intensity distribution on a line including the puncture needle within the specified region. Moreover, the puncture needle connection processor 94b generates an image representing the puncture needle based on the tip position of the puncture needle, superimposes the image on the B-mode image, and outputs the B-mode image to the differential processor 88.

The candidate point extractor 100 applies an edge extraction filter (weighted addition filter) corresponding to the insertion angle of the puncture needle to the B-mode image shown in FIG. 11A to make the image continuous in the direction of the insertion angle of the puncture needle. Moreover, the candidate point extractor 100 performs threshold processing on the B-mode image to which the edge extraction filter is applied to thereby create an edge image (see FIG. 11B) so that only the feature points (needle candidate points) having a luminance not lower than the threshold appear white. The line generator 112 calculates the position of a puncture needle candidate line from the distribution of the feature points of the puncture needle within the edge image.

Figure 11B:
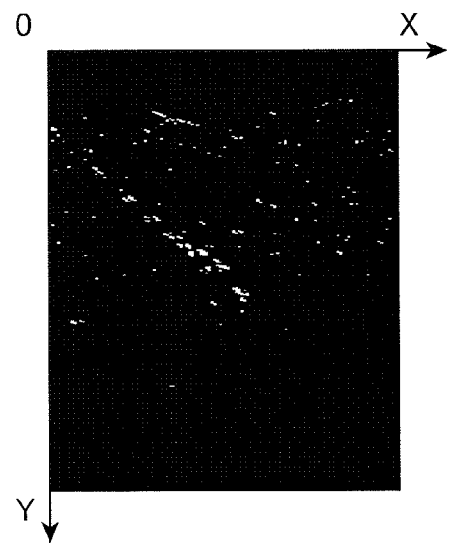
FIG. 11B shows an example of an edge image obtained after performing threshold processing on the B-mode image shown in FIG. 11A.
Figure 11C:
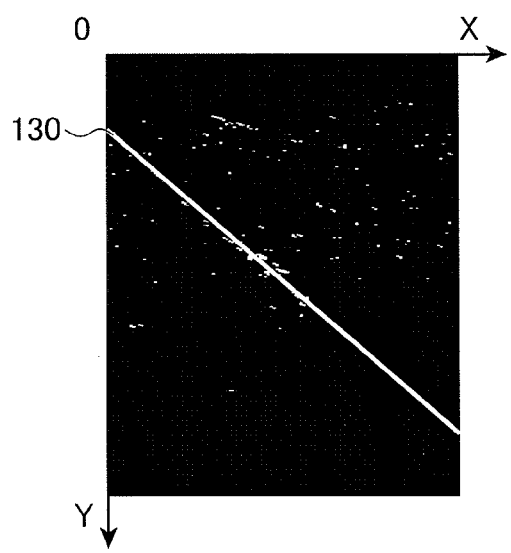
FIG. 11C shows an example of an edge image in which a line specified through Hough transform is displayed so as to be superimposed on the edge image shown in FIG. 11B.

In the edge image shown in FIG. 11B, a plurality of puncture needle feature points displayed with a high luminance within the B-mode image are distributed. Among the respective puncture needle feature points distributed within the edge image, the points appearing at the positions where the puncture needle is present are those mainly originating from the puncture needle, whereas the points appearing over the entire screen regardless of the positions where the puncture needle is present are those originating from tissues or the like other than the puncture needle. The puncture needle feature points originating from tissues or the like become noise when specifying the position of the puncture needle based on the edge image. Thus, the line generator 112 performs Hough transform on the edge image including noise shown in FIG. 11B to thereby generate a puncture needle candidate line which passes the largest number of puncture needle feature points originating from the puncture needle. Even when the edge image includes noise, since the puncture needle feature points originating from the puncture needle show a linear connection, it is possible to generate a line which extends along the linear connection of the puncture needle feature points originating from the puncture needle through the Hough transform. FIG. 11C shows an image in which the generated puncture needle candidate line 130 is displayed so as to be superimposed on the edge image data. The puncture needle candidate line 130 shown in FIG. 11C shows the puncture needle and the extension line of the puncture needle.

Figure 11D:
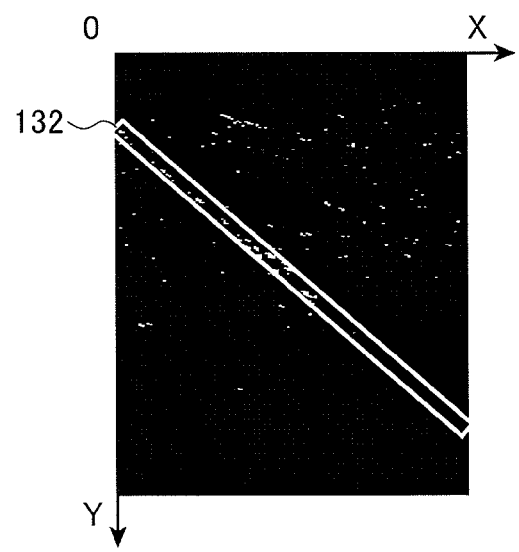
FIG. 11D shows an example of an edge image in which a puncture needle presence region is displayed so as to be superimposed on the edge image shown in FIG. 11C.

The puncture needle candidate line 130 which represents the puncture needle and the extension line of the puncture needle has an unclear boundary between the puncture needle and a non-puncture needle region. Thus, the boundary position on the puncture needle candidate line 130 between the puncture needle and the non-puncture needle region, namely the tip position of the puncture needle is calculated. FIG. 11D shows an edge image on which a region 132 is superimposed, in which the region 132 is obtained by the region generator 114 expanding the puncture needle candidate line 130 generated through the Hough transform to a predetermined width. The region 132 is a region which includes the puncture needle candidate line 130. The region generator 114 specifies the region 132 as a puncture needle presence region where the puncture needle is present. Since the puncture needle candidate line 130 extracted by the Hough transform is a line which passes the largest number of puncture needle feature points originating from the puncture needle, a region including a number of puncture needle feature points is specified as the puncture needle presence region 132. The puncture needle connection processor 94b creates the region 132 in this way and narrows the region 132 down to a region where the puncture needle is highly likely to be present. Here, the predetermined width to which the puncture needle candidate line 130 is expanded may be the thickness of the puncture needle read from the information storage unit 80 and may be set by the user while seeing the B-mode image or the edge image.

Figure 12B:
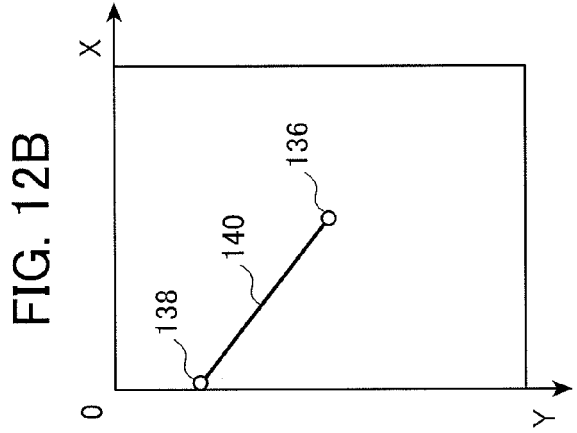
FIG. 12B is a schematic diagram showing a line which connects the tip position of the puncture needle specified by the method of FIG. 12A and the starting point of the puncture needle.
Figure 12A:
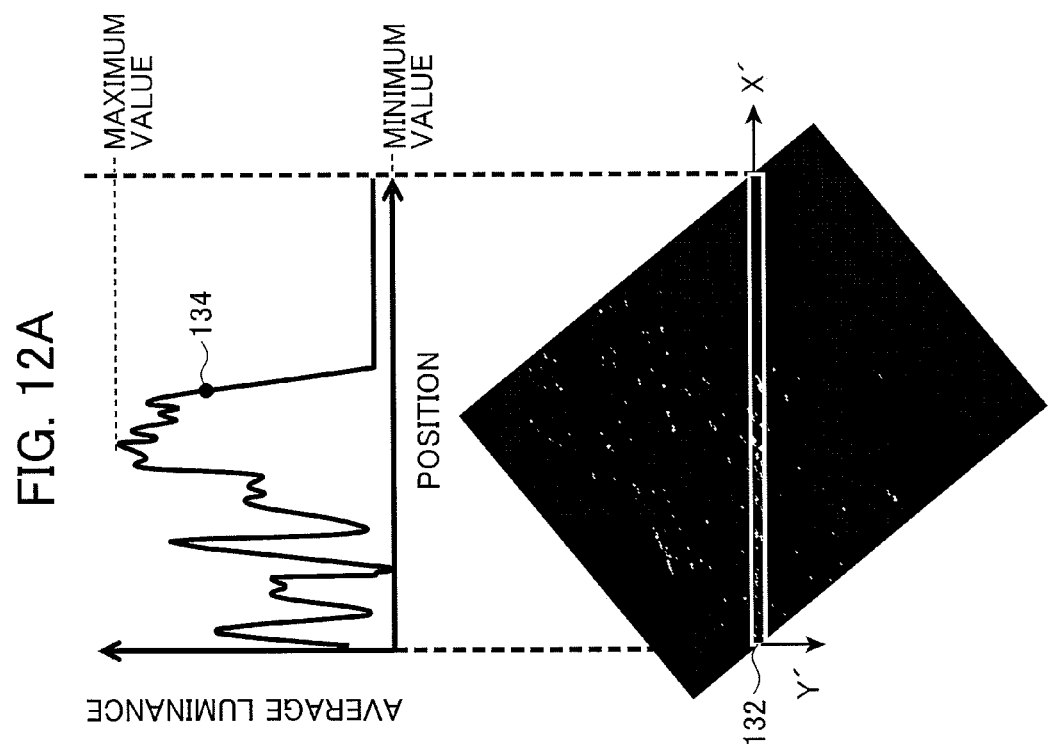
FIG. 12A is a schematic diagram showing a method of specifying a tip position in the puncture needle presence region shown in FIG. 11D.

Subsequently, the average luminance calculator 116 of the position specifying unit 106 rotates the edge image shown in FIG. 11D until the longitudinal direction of the region 132 becomes horizontal and defines an X'Y' orthogonal coordinate system so that the longitudinal direction of the region 132 corresponds to an X' axis, and the lateral direction of the region 132 corresponds to a Y' axis. The average luminance calculator 116 averages the luminance values at the points (points having the same X' coordinate value) within the region 132 arranged in the Y'-axis direction. FIG. 12A is a view showing the region 132 within the edge image so as to correspond to a graph showing the distribution of average luminance values on a line (the region 132 reduced to 1D as the result of averaging the luminance values at the points with the same X' coordinate value within the region 132) including the puncture needle within the region 132 in order to illustrate a method of specifying the tip position from the region 132. The graph of FIG. 12A is a graph showing the distribution of average luminance values in the region 132 as viewed in the scanning direction (X'-axis direction), in which the X' coordinate is shown on the horizontal axis, and the average luminance on the vertical axis. The maximum luminance specifying unit 118 and the minimum luminance specifying unit 120 calculate the maximum and minimum values of the average luminance based on the graph shown in FIG. 12A. The graph shown in FIG. 12A is depicted in a simplified manner for better understanding of the invention.

The puncture needle tip position calculator (hereinafter referred to as a position calculator) 122 scans the average luminance values from the maximum side of the X' coordinate to the origin side in the graph of FIG. 12A showing the relationship between the X' coordinate and the average luminance within the region 132 to thereby specify the tip position of the puncture needle. Specifically, the position calculator 122 specifies a point 134 at which the average luminance which had a value near the minimum value due to the non-presence of the puncture needle increases greatly to reach a luminance corresponding to 80% of the difference between the maximum and minimum values for the first time as the tip position of the puncture needle. Here, the reason why the average luminance values are scanned from the maximum side of the X' coordinate is because by scanning the average luminance values from a side where the puncture needle is expected not to be present, a point at which the luminance varies abruptly can be specified as the tip position of the puncture needle. If the average luminance values are scanned from the origin side, the average luminance at a position where the puncture needle is discontinuous has a value near the minimum value, and after that, a point where the puncture needle is detected is likely to be specified as the tip end. In this example, a point corresponding to 80% of the difference between the maximum and minimum values, which is the point empirically preferable as a point that can substantially specify the puncture needle tip, is set as the tip position of the puncture needle, although the proportion may not always be 80%. However, since a point originating from noise may be specified as the tip position if a point too close to the minimum side of the average luminance values is set as the tip position, it is preferable to set the tip position to the point corresponding to not less than 50% of the difference between the maximum and minimum values of the average luminance.

Within the region 132, the average luminance values in a region where the puncture needle is not present are approximately 0. Thus, if the average luminance values are scanned toward the 0 side from the maximum side of the X' coordinate where the puncture needle is not present, values near 0 appear for a considerable amount of time. When the scanning advances into a region where the puncture needle is present from the region where the puncture needle is not present, the average luminance values increase abruptly. This is because the puncture needle is detected in high luminance. The position calculator 122 specifies the point 134 which is the tip position of the puncture needle based on a change in the average luminance values due to the presence/absence of the puncture needle. After specifying the point 134 which is the tip position of the puncture needle, the puncture needle tip position calculator 122 converts the X'Y' orthogonal coordinate system into the XY orthogonal coordinate system to calculate the X and Y coordinates of the point 134.

The puncture needle image generator 108 generates a line representing the puncture needle based on the puncture needle candidate line 130 and the tip position 134 of the puncture needle. Specifically, a segment 140 which is a line representing the puncture needle is generated using the puncture needle candidate line 130 as a segment which extends from the position of the X coordinate 0 to a point 136 on the puncture needle candidate line 130 having the same X coordinate as the X coordinate of the tip position 134 of the puncture needle. FIG. 12B is a schematic view showing the segment 140 generated by the puncture needle image-generator 108. A point 138 in FIG. 12B is a point at which the puncture needle candidate line 130 meets the left side of the edge image.

The puncture needle connection processor 94b performs the process of detecting the tip position of the puncture needle and generating an image representing the puncture needle at predetermined time intervals, superimposes an image representing the puncture needle generated latest on the B-mode image, and outputs the B-mode image to the differential processor 88. The puncture needle connection processor 94b specifies the tip position of the puncture needle and superimposes the generated puncture needle image (the image representing the puncture needle) on the B-mode image, whereby a frame image in which the position of the puncture needle is clearly visible can be output to the differential processor 88.

As the puncture tool connection process of making the puncture needle continuous, a puncture needle connection process of extracting and connecting needle candidate points to thereby generate a puncture needle image, applied in an ultrasound image generation apparatus and an ultrasound image generation method according to the second aspect of the invention can be applied.

The puncture needle connection process performed by the puncture needle connection processor 94b may be performed as the LUT processing performed by the tip detector 70.

The ultrasound image diagnostic apparatus according to the first aspect of the invention basically has the configuration described hereinabove.

Next, the operation of the ultrasound image diagnostic apparatus and the ultrasound image generation method according to the first aspect of the invention will be described.

Figure 13:
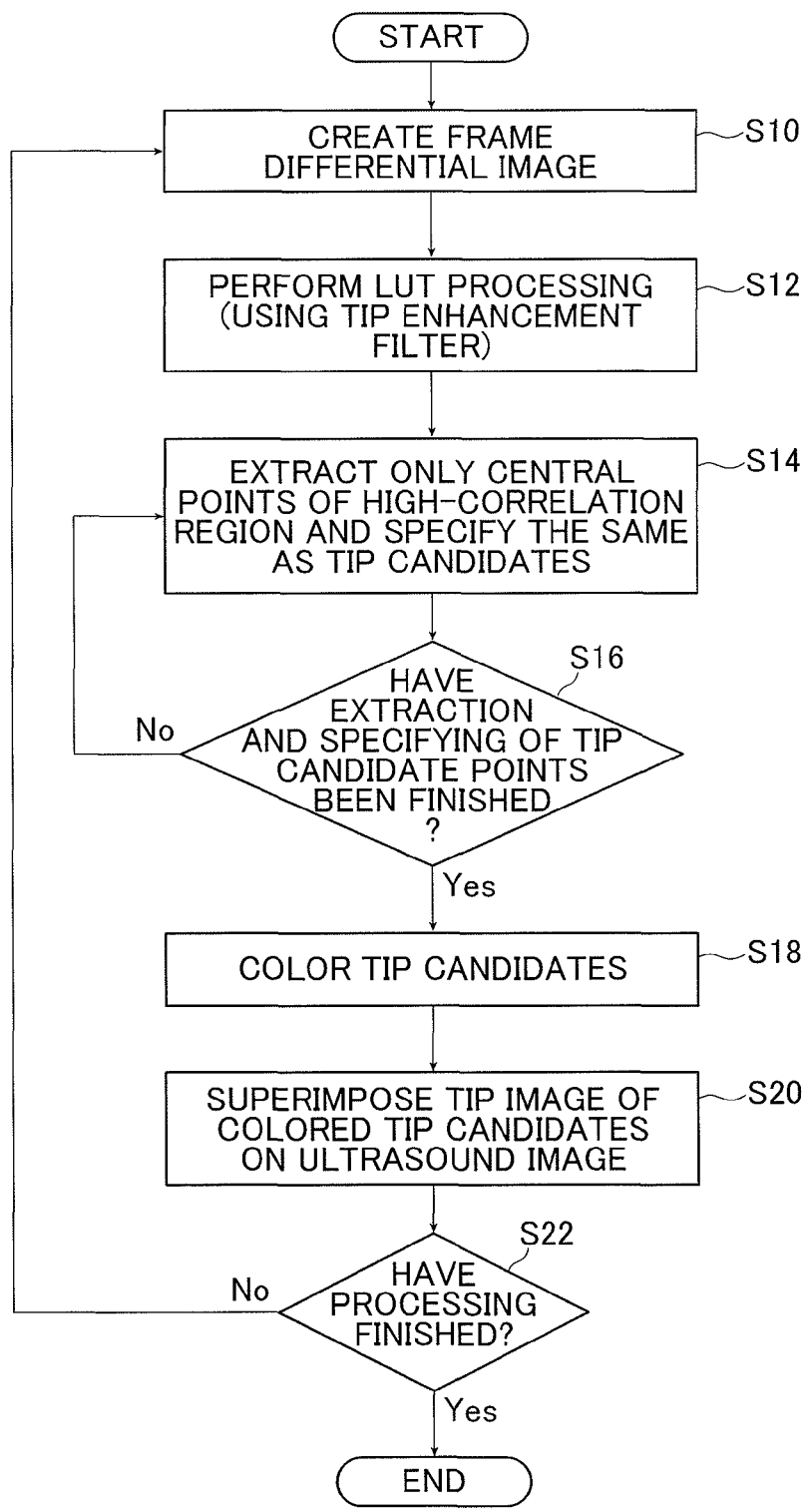
FIG. 13 is a flowchart showing an example of main parts of an ultrasound image generation method according to the first aspect of the invention.

FIG. 13 is a flowchart showing an example of main parts of the ultrasound image generation method according to the present aspect, in which the flowchart starts from a step of generating a differential image and ends with a step of generating a combined image in which a tip image including colored puncture needle tip candidates is superimposed on a B-mode image.

First, an operator brings the ultrasound wave transceiving surface of the ultrasound probe 12 into contact with the surface of a subject to be examined. In this state, ultrasound waves are transmitted from the plurality of transducers 34 in accordance with the driving signal supplied from the transmission driver 38 of the probe body 16, and the reception signals output from the respective transducers 34 having received the ultrasound echoes from the subject are supplied to the corresponding reception signal processors 36, whereby the sample data are generated. The sample data are transmitted to the diagnostic apparatus main body 14 through the communication cable 18 and stored in the data storage unit 46. Moreover, the sample data of each frame are read from the data storage unit 46, and B-mode image data of each frame are generated by the image generator 64 of the combined image generator 48, and B-mode image data of time-sequential frames are stored in the frame image storage unit 66.

Subsequently, in accordance with the flow of FIG. 13, a combined image in which the tip image in which puncture needle tip candidates are colored as the highlighting process is superimposed on the B-mode image is generated.

Figure 14C:
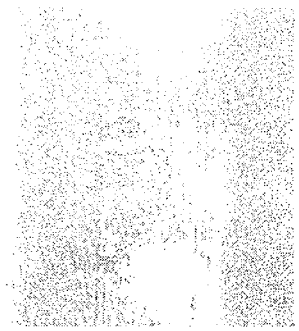
FIG. 14C shows a differential image of the ultrasound images shown in FIGS. 14A and 14B.
Figure 14B:
FIGS. 14A and 14B are examples of two time-sequential frames of ultrasound images.
Figure 14A:

As shown in FIG. 13, first, in step S10, the differential image generator 68 performs differential processing to generate a frame differential image shown in FIG. 14C from the B-mode image data of two time-sequential frames, a frame earlier than the present frame and the present frame shown in FIGS. 14A and 14B, read from the frame image storage unit 66.

Figure 14E:
FIG. 14E shows an example of a LUT processed image of the differential image shown in FIG. 14C.
Figure 14D:
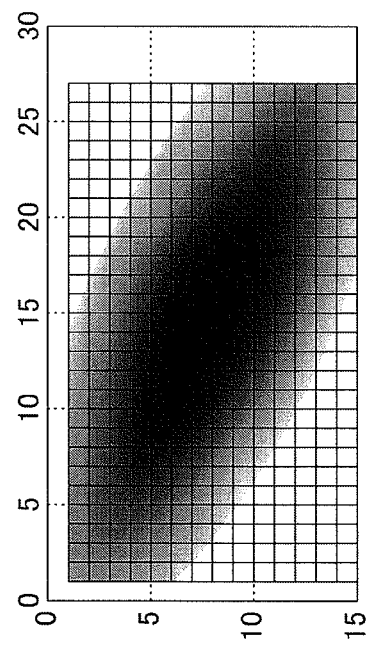
FIG. 14D shows an example of a tip enhancement filter for lookup table processing (LUT processing) to be applied to the differential image shown in FIG. 14C.
Figure 15:
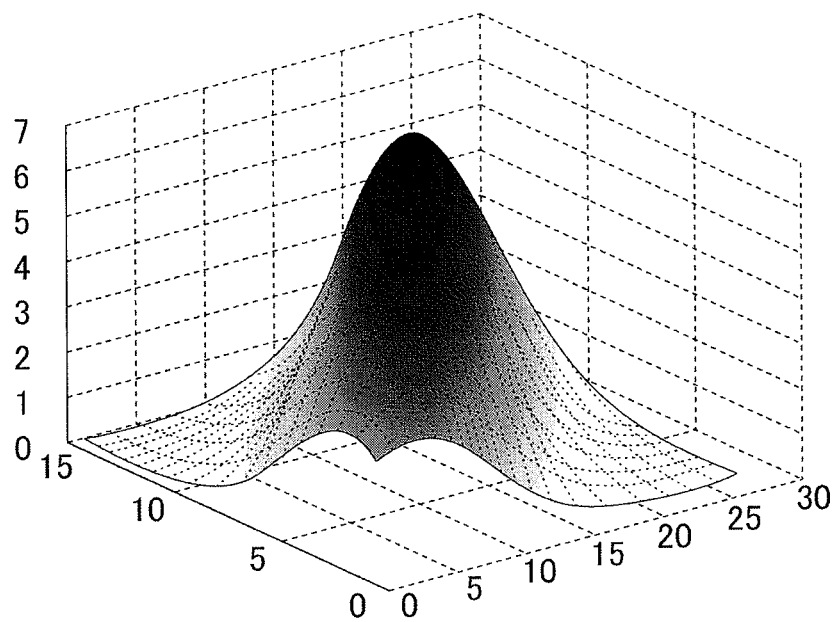
FIG. 15 is a view showing an example of a Gaussian filter used as the base that determines a filter coefficient of the tip enhancement filter shown in FIG. 14D.

Subsequently, in step S12, the candidate point extractor 82 of the tip candidate detector 74 of the tip detector 70 performs LUT processing using a tip enhancement filter shown in FIG. 14D to extract tip candidate points. The tip enhancement filter shown in FIG. 14D is a filter for causing defocusing in the insertion direction of the puncture needle which has a rectangular shape and a size of 15×27 pixels, and which has filter coefficients weighted along the insertion direction of the puncture needle by a Gaussian filter shown in FIG. 15. FIG. 14E shows a LUT-processed image obtained through the LUT processing using the tip enhancement filter.

Figure 16:
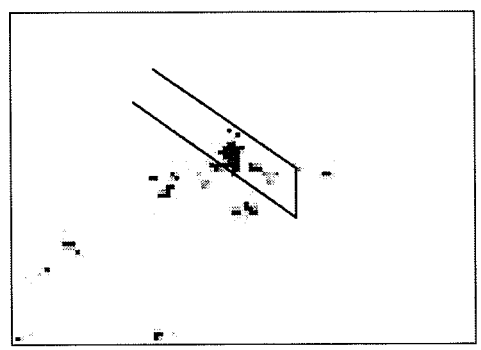
FIG. 16 is a view showing an example of the distribution of tip candidate points of a puncture needle after binarization of the differential image shown in FIG. 14C.

FIG. 16 shows the distribution of puncture needle tip candidate points in a rectangular region including a puncture needle tip in an image which is obtained by binarizing the frame differential image shown in FIG. 14C based on a luminance difference. As can be understood from FIG. 16, after the binarization, a plurality of puncture needle tip candidate points are present at positions other than the vicinity of the puncture needle tip.

Subsequently, in step S14, the tip candidate specifying processor 84 specifies only the central point of tip candidate points in a region having a high correlation with the puncture needle, in particular, the tip end thereof as the tip candidate.

In step S16, it is determined whether the tip candidate specifying processor 84 has finished the process of extracting and specifying the tip candidates within the differential image. If the process has not finished, the flow returns to step S14 and the process of extracting and specifying the tip candidates is continued. If the process has finished, the flow proceeds to step S18.

In step S18, the tip candidate processor 76 colors the tip candidates specified in step S14 to generate a tip image.

Subsequently, in step S20, the image combiner 72 combines the tip image generated in step S18 with the ultrasound image (B-mode image) of the present frame to thereby generate a combined image in which the tip candidates colored by the tip candidate processor 76 are superimposed on the ultrasound image of the present frame.

Subsequently, in step S22, it is determined whether the image combiner 72 has finished the process of generating the combined image. If the process has not finished, the flow returns to step S10, and the process which starts from the step of generating the differential image and ends at step S20 of generating the combined image is repeated. If the process has finished, the processes of FIG. 13 end.

After that, the combined image combined by the image combiner 72 is sent to the display controller 50 and converted into a combined image signal for display, and a combined image in which the colored tip candidates are superimposed on the ultrasound image of the present frame is displayed on the display unit 52.

The ultrasound image generation method of the first aspect of the invention is performed in the above-described manner.

The example shown in FIG. 13 shows an example in which a tip candidate is always detected from the differential image. However, since the tip candidate may not be detected, a process taking a case where no tip candidate is detected into consideration will be described.

Figure 17:
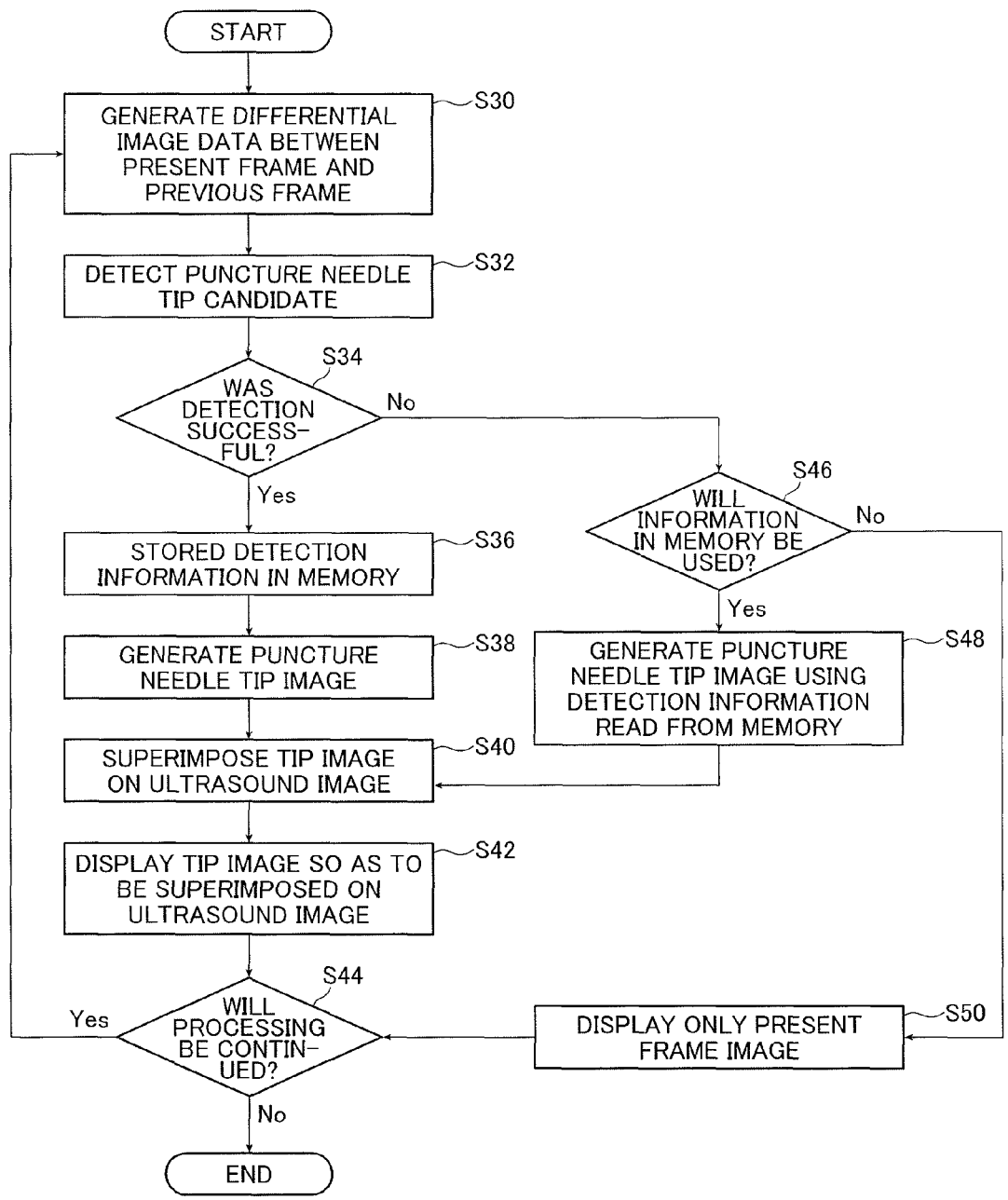
FIG. 17 is a flowchart showing another example of main parts of the ultrasound image generation method according to the first aspect of the invention.

FIG. 17 is a flowchart showing an example of the ultrasound image generation method according to the first aspect of the invention, taking a case where no tip candidate is detected into consideration.

First, in step S30, B-mode image data of the present frame is subtracted from B-mode image data of a frame earlier than the present frame to generate frame differential image data.

Subsequently, in step S32, the LUT processing or the tip candidate specifying process is performed on the differential image data to thereby detect puncture needle tip candidates.

In step S34, it is determined whether a puncture needle tip candidate is detected in step S32. If the puncture needle tip candidate is detected, the flow proceeds to step S36 by determining that the detection was successful. If the puncture needle tip candidate is not detected, the flow proceeds to step S46.

In step S36, detection information including the information on the puncture needle tip candidate detected in step S32 is stored in a memory (the tip candidate storage unit 78).

In step S38, the detected tip candidate is read from the memory, and the read tip candidate is colored, whereby a tip image of the puncture needle is generated.

In step S40, the tip image generated in step S38 is superimposed on the ultrasound image (B-mode image) of the present frame, whereby a combined image in which the colored tip candidate is superimposed on the ultrasound image of the present frame is generated.

In step S42, the combined image in which the colored tip candidate is superimposed on the ultrasound image of the present frame is displayed on the display unit 52.

Subsequently, in step S44, it is determined whether the process of detecting puncture needle tip candidates and displaying the combined image will be continued. If the process is to be continued, the flow returns to step S30, the process which starts from the step of generating the differential image data and ends at step S42 of displaying the combined image is repeated. If the process is to be finished, the processes of FIG. 17 end.

On the other hand, when it is determined in step S34 that the detection of the puncture needle tip candidate was not successful, it is determined in step S46 whether the detection information on the past puncture needle tip candidates in the memory will be used. If the information is to be used, the flow proceeds to step S48. If the information is not to be used, the flow proceeds to step S50.

In step S48, the past puncture needle tip candidates are colored using the detection information read from the memory to thereby generate a tip image of the puncture needle, and the flow proceeds to step S40. In step S40, the tip image of the puncture needle generated in step S48 is superimposed on the ultrasound image (B-mode image) of the present frame, whereby a combined image is generated.

In step S50, since there is no detection information and no tip candidate, the ultrasound image of the present frame is displayed on the display unit 52, and the flow proceeds to step S44. In step S44, as described above, it is determined whether the detection process will be continued, and the detection process is continued or finished in accordance with the determination result.

Figure 18:
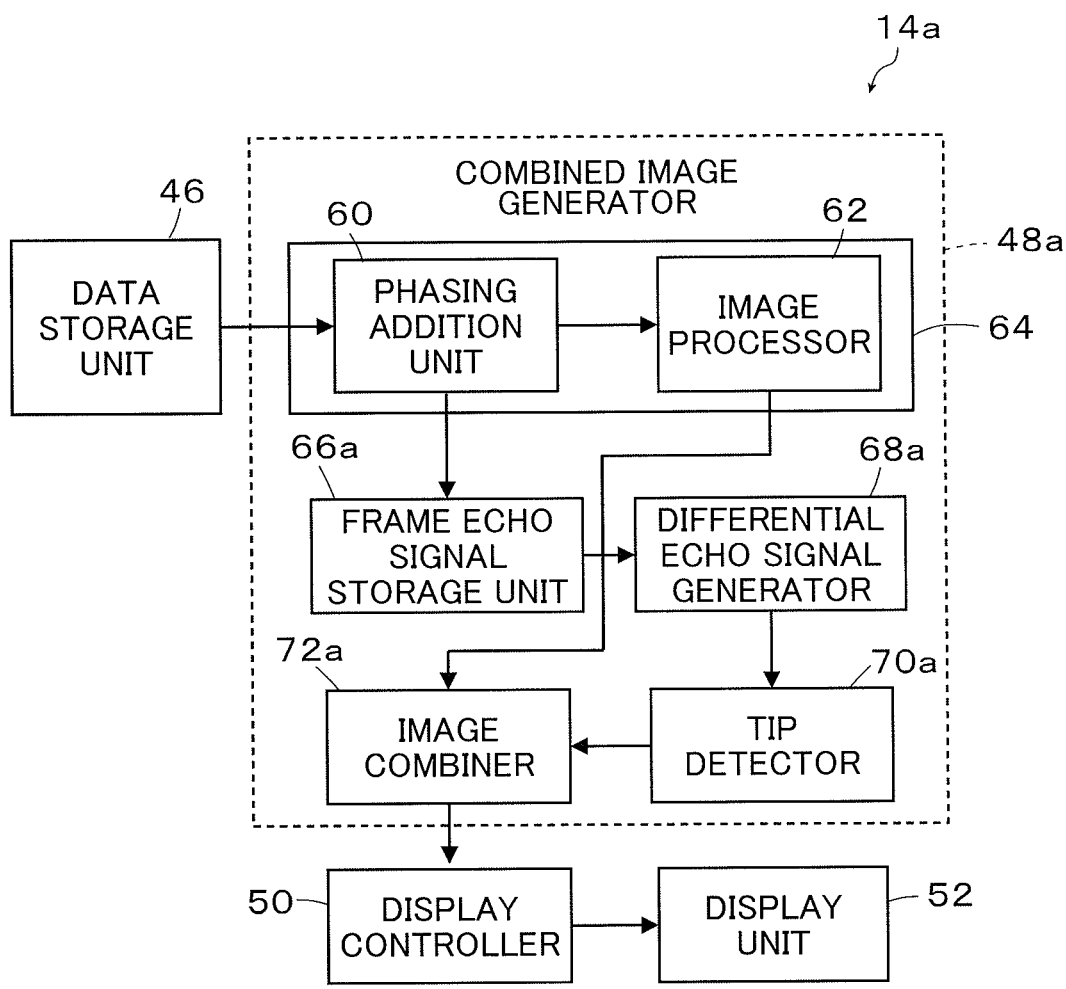
FIG. 18 is a block diagram schematically showing a configuration of another embodiment of a diagnostic apparatus main body of the ultrasound diagnostic apparatus according to the first aspect of the invention.

In the embodiment shown in FIG. 1, as described above, the processes of generating the differential image of two frames, detecting the tip candidates, generating the tip image, and superimposing the tip image on the ultrasound image (B-mode image) of the present frame are performed based on the B-mode image signals generated by the image processor 62 of the image generator 64. However, the invention is not limited to this, and instead of the B-mode image signals, as shown in FIG. 18, the processes of generating the differential image of two frames, detecting the tip candidates, generating the tip image, and superimposing the tip image on the ultrasound image of the present frame may be performed based on baseband signals (acoustic-ray signals) having been subjected to beam forming processing by the phasing addition unit 60 of the image generator 64, namely echo signals of each frame. Thus, in the invention, any one of the frame echo signals and the B-mode image signals may be used.

FIG. 18 is a block diagram schematically showing a configuration of another embodiment of the diagnostic apparatus main body of the ultrasound diagnostic apparatus according to the first aspect of the invention.

A diagnostic apparatus main body 14*a* shown in FIG. 18 includes the data storage unit 46, a combined image generator 48*a*, and the display unit 52, and although not shown, further includes the main body controller, the operation unit, and the storage unit similarly to FIG. 1. Moreover, the combined image generator 48*a* includes the image generator 64, a time-sequential frame echo signal storage unit (hereinafter also referred to as an echo signal storage unit) 66*a*, a time-sequential frame differential echo signal generator (hereinafter also referred to simply as a differential echo signal generator) 68*a*, a puncture needle tip detector (tip detector) 70*a*, and an image combiner 72*a*.

The echo signal storage unit 66*a*, the differential echo signal generator 68*a*, the tip detector 70*a*, and the image combiner 72*a* of the combined image generator 48*a* of the diagnostic apparatus main body 14*a* shown in FIG. 18 are the same as the image storage unit 66, the differential image generator 68, the tip detector 70, and the image combiner 72 of the combined image generator 48 of the diagnostic apparatus main body 14 shown in FIG. 1, except that the elements shown in FIG. 18 perform processes based on echo signals whereas the elements shown in FIG. 1 perform processes based on B-mode image signals. That is, the contents of the processes performed by the two groups of elements are approximately the same, except that the signals (data) to be processed are different. Thus, detailed description of the contents of the same processes performed by the respective elements will not be provided.

The echo signal storage unit 66*a* is a memory that time-sequentially stores echo signals representing images of a plurality of frames.

The differential echo signal generator 68*a* calculates a difference between echo signals of two time-sequential frames stored in the echo signal storage unit 66*a* to thereby generate a differential echo signal.

The tip detector 70*a* which is the most characteristic portion of the present embodiment performs a process of detecting a tip end from the differential echo signal generated by the differential echo signal generator 68*a*, detects at least one tip candidate including a puncture needle tip, highlights the detected tip candidates, and generates a highlighted tip image. The tip candidates detected from the differential echo signal are preferably subjected to the same conversion process as used by the image processor 62 to generate B-mode image signals, and the tip image is preferably expressed by B-mode image signals.

The image combiner 72*a* combines the tip image (needle tip enhanced image) generated by the tip detector 70*a* with an ultrasound image of the present frame, which is the B-mode image generated by the image processor 62, to thereby generate a combined ultrasound image.

When the tip image generated by the tip detector 70*a* is not expressed by B-mode image signals, the image combiner 72*a* performs the same conversion process as used by the image processor 62 on the tip image to generate B-mode image signals and then combines the tip image so as to be superimposed on the ultrasound image of the present frame, which is a B-mode image.

When the ultrasound image of the present frame, which is the B-mode image generated by the image processor 62 is expressed by a display image signal which is scan-converted by the DSC, it is necessary to perform scan conversion with the DSC so that the tip image converted into the B-mode image is also expressed by a display image signal.

The conversion from signals or data subjected to processing into B-mode image signals and the scan conversion may be performed in any step as long as the signals or data to be combined have the same format when they are combined by the image combiner 72a. The scan conversion may not be performed in the combined image generator 48a when it is performed by the display controller 50.

The ultrasound diagnostic apparatus and the ultrasound image generation method according to the first aspect of the invention have the above-described configuration.

Next, an ultrasound image generation apparatus and an ultrasound image generation method according to the second aspect of the invention will be described.

Figure 19:
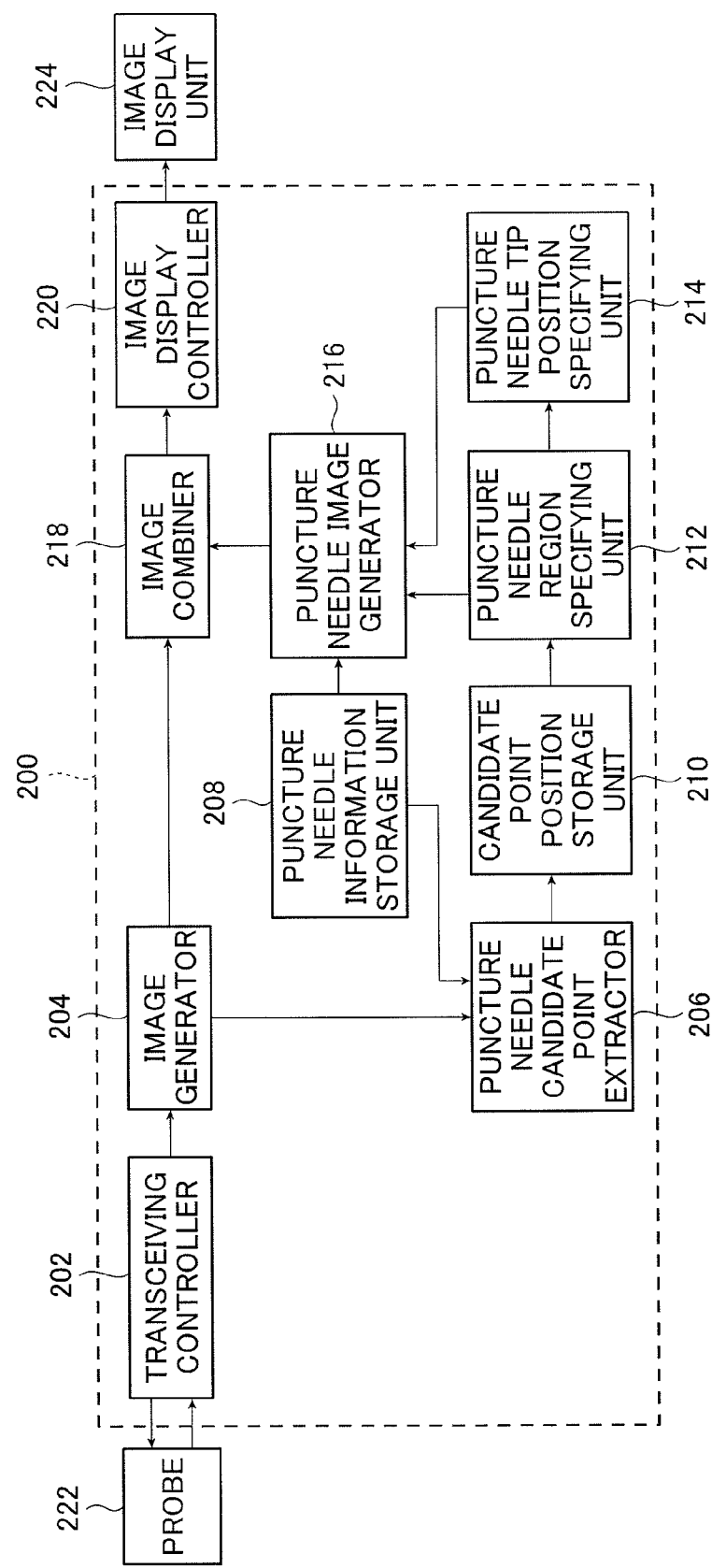
FIG. 19 is a functional block diagram schematically showing a configuration of an embodiment of an ultrasound image generation apparatus according to a second aspect of the invention.

FIG. 19 is a functional block diagram schematically showing a configuration of an embodiment of an ultrasound image generation apparatus according to the second aspect of the invention.

An ultrasound image generation apparatus (hereinafter referred to as a generation apparatus) 200 shown in FIG. 19 includes a transceiving controller 202, an image generator 204, a puncture needle candidate point extractor 206, a puncture needle information storage unit 208, a candidate point position storage unit 210, a puncture needle region specifying unit 212, a puncture needle tip position specifying unit 214, a puncture needle image generator 216, an image combiner 218, and an image display controller 220. The generation apparatus 200 is used by being electrically connected to a probe 222 and an image display unit 224. The generation apparatus 200, the probe 222, and the image display unit 224 form an ultrasound diagnostic apparatus 10a, and the generation apparatus 200 and the image display unit 224 form a diagnostic apparatus main body 14a. Some constituent elements of the generation apparatus 200 are the same as those of the ultrasound diagnostic apparatus 10 shown in FIGS. 1, 2, and 9, and detailed description thereof will not be provided.

Although not shown, the probe 222 includes a plurality of piezoelectric elements, transmits ultrasound waves from the plurality of piezoelectric elements toward a patient, and receives echoes reflected from the patient. The piezoelectric element generates an echo signal upon receiving the echoes. The probe 222 is connected to the generation apparatus 200 through a communication cable not shown and outputs the echo signal to the transceiving controller 202 through the communication cable.

The probe 222 of the present embodiment may be one which includes the plurality of transducers 34, the plurality of reception signal processors 36, and the transmission driver 38 of the probe body 16 of the ultrasound probe 12 shown in FIG. 1.

Although not shown, the transceiving controller 202 includes a pulser that generates a high-voltage electrical signal, an amplifier that amplifies the echo signal reflected from the patient and input from the probe 222, a low-pass filter that rejects high-frequency components of the echo signal, and an A/D converter that converts analog signals into digital signals. The high-voltage pulse signal generated by the pulser is applied to the piezoelectric elements (not shown) in the probe 222, whereby ultrasound waves are transmitted from the probe 222.

In the transceiving controller 202, the echo signal output from the probe 222 is amplified by the amplifier, high-frequency components of the echo signal are rejected by the low-pass filter, the resulting signal is A/D converted by an A/D converter, and the resulting signal is output to the image generator 204.

The transceiving controller 202 of the present embodiment may be one which includes the reception signal processors 36, the transmission driver 38, the transmission controller 42, the reception controller 42, and the probe controller 44 of the probe body 16 of the ultrasound probe 12 shown in FIG. 1.

In the present embodiment, although the probe 222 does not include the transceiving controller 202, the probe 222 may include the transceiving controller 202 similarly to the probe body 16 of the ultrasound probe 12 shown in FIG. 1. Moreover, the probe 222 may include a puncture adapter similarly to the ultrasound probe 12 shown in FIG. 1.

Although not shown, the image generator 204 includes a delay circuit, an addition circuit, and a STC circuit. The image generator 204 adds the echo signals output from the transceiving controller 202 by delaying in accordance with the position of the piezoelectric element to thereby form an acoustic-ray signal. In the image generator 204, the STC circuit corrects attenuation of the acoustic-ray signal based on a distance in accordance with the depth of the reflection position of the ultrasound wave. After that, the image generator 204 generates B-mode image data.

The image generator 204 may be configured by the image generator 64 of the diagnostic apparatus main body 14 shown in FIG. 1, which includes the phasing addition unit 60 and the image processor 62. Moreover, a storage unit (data storage unit) which temporarily stores the digital echo signal may be provided between the image generator 204 and the transceiving controller 202.

The puncture needle information storage unit (hereinafter also referred to as an information storage unit) 208 is a storage unit that stores information on the puncture needle which is a puncture tool. Here, the information storage unit 208 may have the same configuration and function as the information storage unit 80 shown in FIG. 2 in that it stores information on the puncture needle. The information storage unit 208 acquires and stores information on the puncture needle through the input or the like from the user.

The puncture needle candidate point extractor 206 extracts needle candidate points as the feature points of the puncture needle using the information on the puncture needle stored in the information storage unit 208 and the B-mode image data generated by the image generator 204. Specifically, an edge extraction filter is applied to the B-mode image data, which are then subjected to CFAR processing and threshold processing, whereby edge image data are created. Then, candidate points of the puncture needle are extracted from the edge image data as the feature points on the puncture needle. Here, the puncture needle candidate point extractor 206 may have a configuration different from the puncture needle candidate point extractor 100 shown in FIG. 9 in that it performs speckle noise removal processing, CFAR processing, MIP processing, or the like. However, the puncture needle candidate point extractor 206 may have the same configuration and function as the puncture needle candidate point extractor 100 shown in FIG. 9 with regard to extraction of needle candidate points. Thus, the same description as that of the puncture needle candidate point extractor 100 is applied with regard to the display of the puncture needle and extraction of feature points, and redundant description thereof will not be provided. The candidate points (feature points) of the puncture needle may be detected from one frame and may be detected from a plurality of frames. When detecting the candidate points from a plurality of frames, it is preferable to use about five frames while updating the frames and the candidate points.

The candidate point position storage unit 210 has the same configuration and function as the candidate point position storage unit 102 shown in FIG. 9. That is, the candidate point position storage unit 210 stores the positions of all needle candidate points extracted by the puncture needle candidate point extractor 206 and outputs the positions of the puncture needle candidate points to the puncture needle region specifying unit 212.

The puncture needle region specifying unit 212 has the same configuration and function as the puncture needle region specifying unit 104 shown in FIG. 9. That is, the puncture needle region specifying unit 212 generates a line (puncture needle candidate line) representing the puncture needle and the extension line of the puncture needle based on the distribution of a plurality of needle candidate points stored in the candidate point position storage unit 210. The puncture needle region specifying unit 212 specifies a region including the generated line as a region where the puncture needle is present.

The puncture needle tip position specifying unit 214 has the same configuration and function as the puncture needle tip position specifying unit 106 shown in FIG. 9. That is, the puncture needle tip position specifying unit 214 specifies the tip position of the puncture needle based on luminance information of a region, in which the puncture needle is highly likely to be present, specified by the puncture needle region specifying unit 212 and outputs the specified tip position to the puncture needle image generator 216.

The puncture needle image generator 216 has the same configuration and function as the puncture needle image generator 108 shown in FIG. 9. That is, the puncture needle image generator 216 generates an image representing the puncture needle based on the line representing the puncture needle and the extension line of the puncture needle, generated by the puncture needle region specifying unit 212 and the tip position of the puncture needle specified by the puncture needle tip position specifying unit 214 and outputs the image to the image combiner 218. Thus, the same description as that of the puncture needle image generator 108 is applied with regard to the form selection and generation of the image representing the puncture needle and setting of the color, luminance, and the like of the image representing the puncture needle, except that the puncture needle information is read from the information storage unit 208. Therefore, redundant description thereof will not be provided.

The puncture needle candidate point extractor 206, the information storage unit 208, the candidate point position storage unit 210, the puncture needle region specifying unit 212, the puncture needle tip position specifying unit 214, and the puncture needle image generator 216 described above form a puncture needle detection circuit.

The image combiner 218 generates combined B-mode image data in which the image representing the puncture needle generated by the puncture needle image generator 216 is displayed so as to be superimposed on the B-mode image data output from the image generator 204. The image combiner 218 outputs the combined B-mode image data to the image display controller 220.

The image display controller 220 has a DSC and has the same configuration and function as the display controller 50 of the diagnostic apparatus main body 14 shown in FIG. 1. In the image display controller 220, the DSC converts the combined B-mode image data combined by the image combiner 218 into display image data corresponding to a general television signal scanning format, performs necessary image processing such as gradation processing, and outputs the processed display image data to the image display unit 224. The generation apparatus 200 specifies the tip position of the puncture needle from the B-mode image to create an image representing the puncture needle, combines the image with the B-mode image, and causes the combined image to be displayed on the image display unit 224.

The transceiving controller 202, the image generator 204, the puncture needle candidate point extractor 206, the candidate point position storage unit 210, the puncture needle region specifying unit 212, the puncture needle tip position specifying unit 214, the puncture needle image generator 216, the image combiner 218, and the image display controller 220 may be realized by a combination of a central processing unit (CPU) and software (programs) for causing the CPU to execute various processes.

The puncture needle region specifying unit 212 and the puncture needle tip position specifying unit 214 shown in FIG. 19 have the same configuration and function as the puncture needle region specifying unit 104 and the puncture needle tip position specifying unit 106 shown in FIG. 10, respectively, and detailed description thereof will not be provided.

Although not shown, the puncture needle region specifying unit 212 has a puncture needle line generator and a puncture needle region generator similarly to the puncture needle region specifying unit 104 shown in FIG. 10. These constituent elements have the same configuration and function as the puncture needle line generator 112 and the puncture needle region generator 114 shown in FIG. 10, respectively, and detailed description thereof will not be provided.

Although not shown, the puncture needle tip position specifying unit 214 has an average luminance calculator, a maximum luminance specifying unit, a minimum luminance specifying unit, and a puncture needle tip position calculator similarly to the puncture needle tip position specifying unit 104 shown in FIG. 10. These constituent elements have the same configuration and function as the average luminance calculator 116, the maximum luminance specifying unit 118, the minimum luminance specifying unit 120, and the puncture needle tip position calculator 122 shown in FIG. 10, respectively, and detailed description thereof will not be provided.

Next, with reference to FIGS. 11A to 11D and FIGS. 12A and 12B used for description of the first aspect of the invention, a method in the ultrasound image generation apparatus 200 of the present embodiment, of calculating the tip position of the puncture needle from the B-mode image and a method of generating the image representing the puncture needle will be described in more detail. Moreover, the functions of the respective constituent elements of the puncture needle tip position specifying unit 214 of the present embodiment will be described. The description is the same as that of the method of detecting the tip position of the puncture needle and the method of generating the puncture needle image made with reference to FIGS. 11A to 11D and FIGS. 12A and 12B and the description of the functions of the respective constituent elements of the position specifying unit 106 shown in FIG. 9. Thus, detailed description thereof will not be provided.

When the B-mode image of the patient including the puncture needle is displayed as shown in FIG. 11A, since the puncture needle in the drawing is displayed in a discontinuous manner, it is difficult for the user to understand the accurate position of the puncture needle. Thus, first, the generation apparatus 200 specifies a region in which the puncture needle is highly likely to be present from the B-mode image as shown in FIG. 11A and specifies the tip position of the puncture needle from the intensity distribution on a line including the puncture needle within the region. Moreover, the generation apparatus 200 generates an image representing the puncture needle based on the tip position of the puncture needle and displays the image on the image display unit 224 together with the B-mode image. That is, the generation apparatus 200 displays the image of the puncture needle generated by specifying the position of the puncture needle together with the B-mode image in which the puncture needle is hardly visible to the user, so that the user can understand the accurate position of the puncture needle.

The puncture needle candidate point extractor 206 applies an edge extraction filter corresponding to an insertion angle of the puncture needle to the B-mode image shown in FIG. 11A to thereby make the image continuous in the direction of the insertion angle of the puncture needle. Moreover, the puncture needle candidate point extractor 206 performs a layer structure removal processing such as CFAR processing to thereby remove a bright line extending in the X-axis direction in the lower part of the drawing. Furthermore, the puncture needle candidate point extractor 206 performs threshold processing on the B-mode image to which the edge extraction filter has been applied to thereby create an edge image (see FIG. 11B) so that only the feature points (needle candidate points) having a luminance not lower than the threshold appear white. The puncture needle line generator calculates the position of a puncture needle candidate line from the distribution of the puncture needle candidate points within the edge image.

The puncture needle line generator performs Hough transform on the edge image including noise shown in FIG. 11B to thereby generate a puncture needle candidate line which passes the largest number of needle candidate points originating from the puncture needle. FIG. 11C shows an image in which the generated puncture needle candidate line 130 is displayed so as to be superimposed on the edge image data.

The puncture needle candidate line 130 which represents the puncture needle and the extension line of the puncture needle has an unclear boundary between the puncture needle and a non-puncture needle region. Thus, the tip position of the puncture needle, which is the boundary position on the puncture needle candidate line 130 between the puncture needle and the non-puncture needle region, is calculated.

The puncture needle region generator expands the puncture needle candidate line 130 to a predetermined width and specifies the region 132 shown in FIG. 11D as a puncture needle presence region. The generation apparatus 200 creates the region 132 in this way and narrows the region in which the puncture needle is highly likely to be present. Here, the predetermined width for expanding the puncture needle candidate line 130 may be the thickness of the puncture needle read from the information storage unit 208 and may be set by the user while seeing the B-mode image or the edge image.

Subsequently, the average luminance calculator of the puncture needle tip position specifying unit 214 rotates the edge image shown in FIG. 11D until the longitudinal direction of the region 132 becomes horizontal and defines an X'Y' orthogonal coordinate system so that the longitudinal direction of the region 132 corresponds to an X' axis, and the lateral direction of the region 132 corresponds to a Y' axis. The average luminance calculator averages the luminance values at the points (points having the same X' coordinate value) within the region 132 arranged in the Y'-axis direction. The maximum luminance specifying unit and the minimum luminance specifying unit calculate the maximum and minimum values of the average luminance based on the graph shown in FIG. 12A.

The puncture needle tip position calculator scans the average luminance values from the maximum side of the X' coordinate to the origin side in the graph of FIG. 12A showing the relationship between the X' coordinate and the average luminance within the region 132 to thereby specify the tip position of the puncture needle. Specifically, the puncture needle tip position calculator specifies a point 134 at which the average luminance which had a value near the minimum value due to the non-presence of the puncture needle increases greatly to reach a luminance corresponding to 80% of the difference between the maximum and minimum values for the first time as the tip position of the puncture needle.

Within the region 132, the average luminance values in a region where the puncture needle is not present are approximately 0. When the scanning advances into a region where the puncture needle is present, the average luminance values increase abruptly. The puncture needle tip position calculator specifies the point 134 which is the tip position of the puncture needle based on a change in the average luminance value due to the presence/absence of the puncture needle. After specifying the point 134 which is the tip position of the puncture needle, the puncture needle tip position calculator converts the X'Y' orthogonal coordinate system into the XY orthogonal coordinate system to calculate the X and Y coordinates of the point 134.

The puncture needle image generator 216 generates a line representing the puncture needle based on the puncture needle candidate line 130 and the tip position 134 of the puncture needle. Specifically, as shown in FIG. 12B, a segment 140 which is a line representing the puncture needle is generated using the puncture needle candidate line 130 as a segment which extends from the position of the X coordinate 0 to a point 136 on the puncture needle candidate line 130 having the same X coordinate as the X coordinate of the tip position 134 of the puncture needle. FIG. 12B is a schematic view showing the segment 140 generated by the puncture needle image generator 216.

The generation apparatus 200 performs the process of detecting the tip position of the puncture needle and generating an image representing the puncture needle at predetermined time intervals and displays the image representing the puncture needle generated latest on the image display unit 224. The generation apparatus 200 specifies the tip position of the puncture needle and displays the generated puncture needle image (the image representing the puncture needle) so as to be superimposed on the B-mode image, so that the position of the puncture needle can be displayed so as to be easily understood by the user.

As the process in the generation apparatus 200, of specifying the tip position of the puncture needle and superimposing the generated puncture needle image on the B-mode image to thereby generate a combined image, the puncture needle connection process applied to the ultrasound diagnostic apparatus and the ultrasound image generation method according to the first aspect of the invention can be applied, for example.

Next, the operation of the ultrasound image generation apparatus and the ultrasound image generation method according to the invention will be described with reference to FIG. 20.

Figure 20:
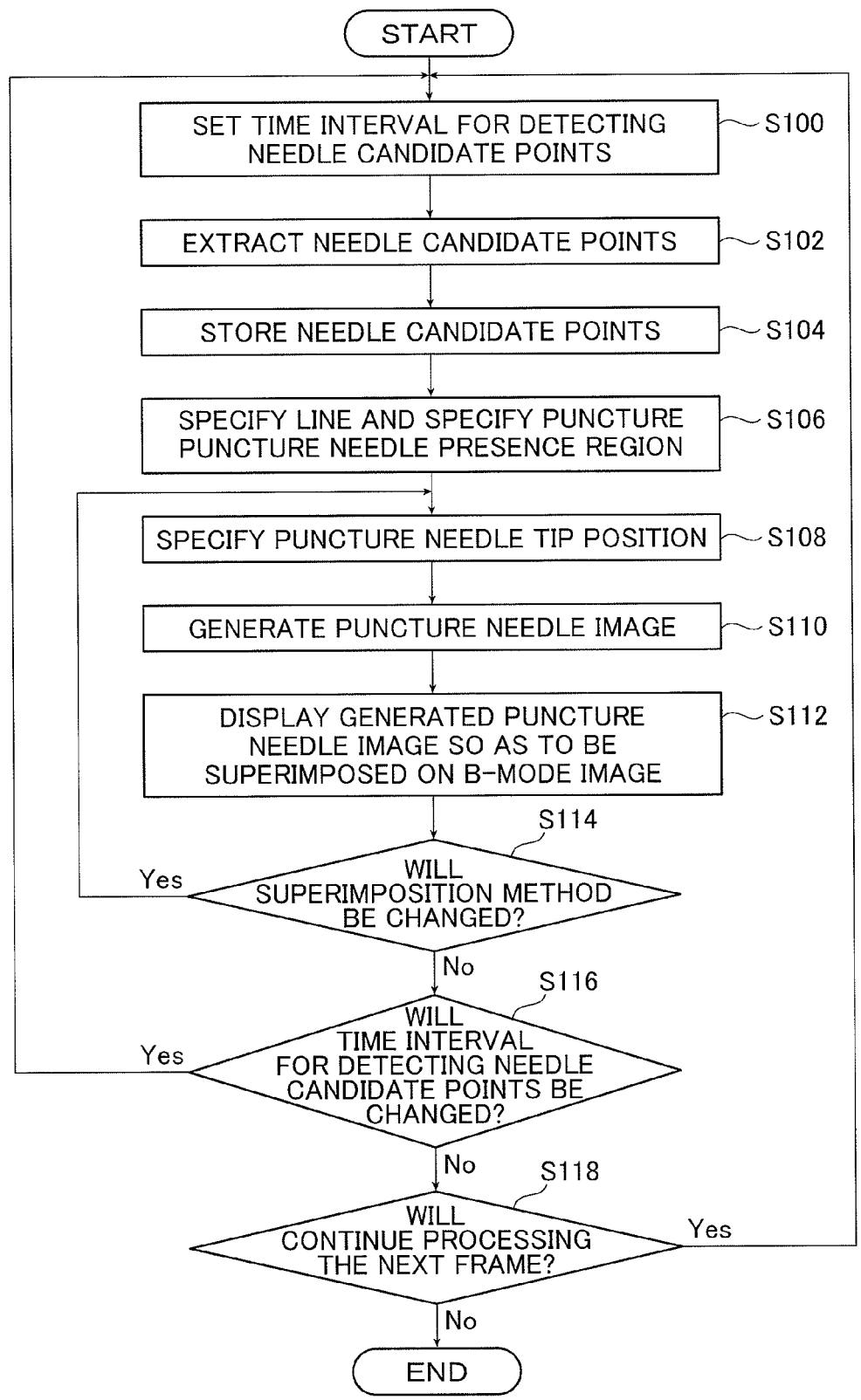
FIG. 20 is a flowchart showing an example of the flow of a series of processes related to an operation of displaying a puncture needle image so as to be superimposed on an ultrasound image in an ultrasound image generation method according to the second aspect of the invention.

FIG. 20 is a flowchart showing the flow of a series of processes related to the operation of displaying the puncture needle image in a superimposed manner in the ultrasound image generation apparatus 200 that performs the ultrasound image generation method of the invention. After ultrasound images are acquired, in step S100, the user sets the time interval for detecting needle candidate points. In step S102, the puncture needle candidate point extractor 206 extracts needle candidate points. In step S104, the coordinates of the puncture needle candidate points are stored in the candidate point position storage unit 210. In step S106, the puncture needle region specifying unit 212 specifies the puncture needle candidate line representing the puncture needle and the extension line of the puncture needle based on the distribution of the puncture needle candidate points. In step S108, the puncture needle tip position specifying unit 214 specifies the tip position of the puncture needle. In step S110, the puncture needle image generator 216 generates the image representing the puncture needle. In step S112, the image combiner 218 combines the B-mode image and the image representing the puncture needle, and the image display controller 220 causes the image display unit 224 to display the image representing the puncture needle so as to be superimposed on the B-mode image.

In step S114, the user selects whether or not to change a superimposition method. If the user selects to change the superimposition method, the flow returns to step S110, and an image representing the puncture needle of which the superimposition method is changed is displayed so as to be superimposed on the B-mode image. If the user selects not to change the superimposition method in step S114, the flow proceeds to step S116. In step S116, the user selects whether or not to change the time interval for extracting needle candidate points. If the user selects to change the time interval, the flow returns to step S100, a new extraction time interval is set, and the puncture needle candidate points are extracted again. If the user selects not to change the time interval for extracting needle candidate points in step S116, the flow proceeds to step S118. In step S118, the user selects whether or not to process the next frame. If the user selects to process the next frame, the flow returns to step S100. If the user selects not to process the next frame in step S118, the processes are terminated.

Figure 21:
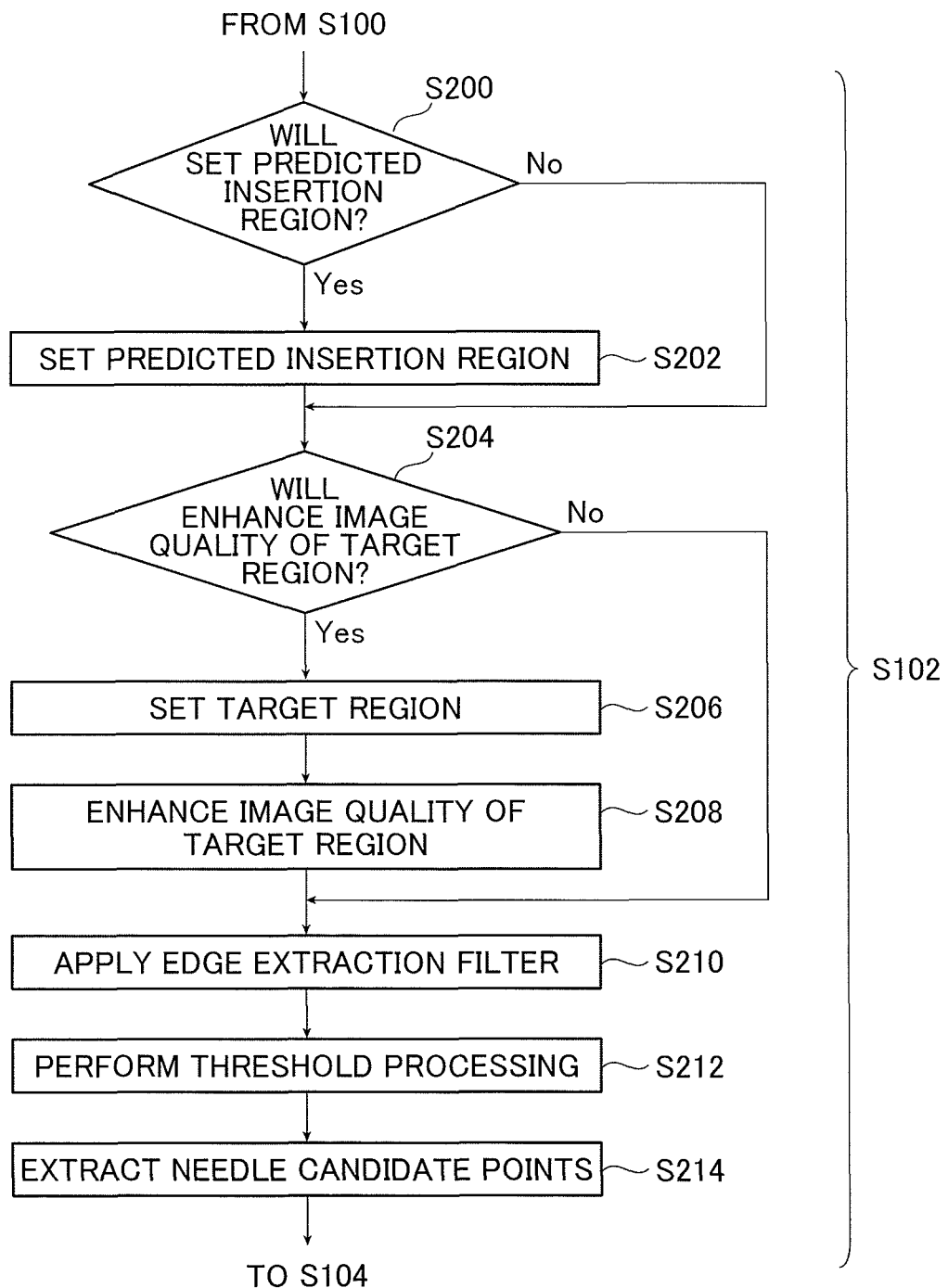
FIG. 21 is a flowchart showing an example of the flow of a process of extracting puncture needle candidate points in the ultrasound image generation method shown in FIG. 20.

FIG. 21 is a flowchart illustrating the operation of step S102 in more detail. In step S200, the user selects whether or not to set a predicted insertion region (a region in which the puncture needle is predicted to be inserted). If the user selects to set the predicted insertion region, the flow proceeds to step S202, the predicted insertion region is set, and then, the flow proceeds to step S204. If the user selects not to set the predicted insertion region in step S200, the flow proceeds to step S204. In step S204, the user selects whether or not to enhance the image quality of a region (hereinafter referred to as a target region) which the user wants to see in particular detail. If the user selects to do so, the flow proceeds to step S206, and the user sets a target region. In step S208, the image quality of the target region is enhanced, and then, the flow proceeds to step S210. If the user selects not to enhance the image quality of the target region in step S204, the flow proceeds to step S210. In step S210, an edge extraction filter is applied. In step S212, threshold processing is performed. In step S214, needle candidate points are extracted from the edge image which has been subjected to threshold processing, and the flow proceeds to step S104.

Figure 22:
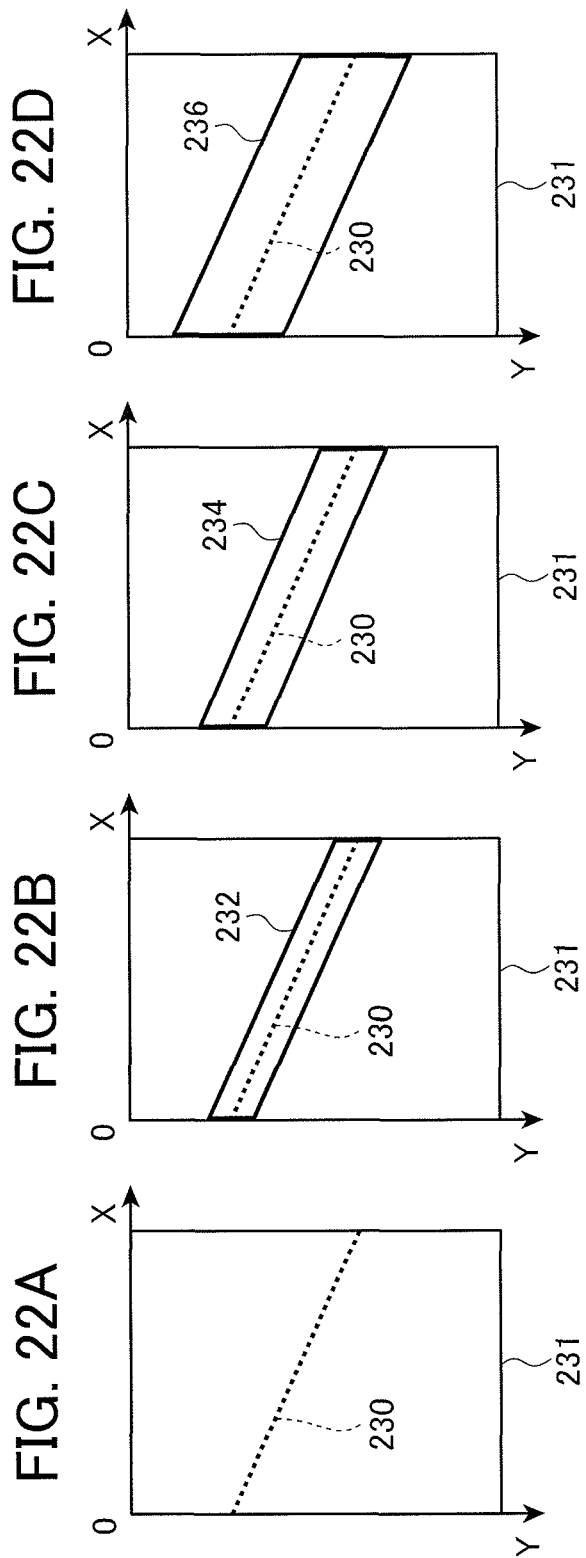
FIG. 22A is a schematic view showing an example of a puncture guide line within a B-mode image.
FIG. 22B is a schematic view showing an example of a predicted insertion region when a predicted insertion region is set to a narrow range.
FIG. 22C is a schematic view showing an example of a predicted insertion region when a predicted insertion region is set to an average range.
FIG. 22D is a schematic view showing an example of a predicted insertion region when a predicted insertion region is set to a wide range.

The operation of setting the predicted insertion region in step S202 will be described with reference to FIGS. 22A to 22D. In FIGS. 22A to 22D, a case where a B-mode image 231 is positioned in an XY orthogonal coordinate system in which the top left corner of the image is at the origin, a horizontal axis extending from the top left corner to the top right corner is an X axis, and a vertical axis extending from the top left corner to the bottom left corner is a Y axis will be considered. In FIG. 22A, a broken line 230 is a puncture guide line. The puncture needle candidate point extractor 206 sets a predicted insertion region based on the puncture guide line 230. When a probe is attached to a puncture adapter, since the insertion path of the puncture needle is determined by the puncture adapter to some extent, it is possible to display the puncture guide line.

In the present embodiment, the predicted insertion region can be set by the user selecting one of three regions having different widths. The predicted insertion region is assumed to have a shape that the puncture guide line is expanded to a predetermined width in the Y-axis direction. For example, when performing puncturing on a shallow portion such as a breast cancer, a narrow region (a region having approximately the same width as the puncture guide line), an average region (a region obtained by expanding the puncture guide line by +0.5 cm in both the positive and negative Y-axis directions), and a wide region (a region obtained by expanding the puncture guide line by +1 cm in both the positive and negative Y-axis directions) are used. The information on a plurality of lines displaced by a predetermined distance from the puncture guide line in both the positive and negative Y-axis directions of the puncture guide line is stored, and an image region interposed by the plurality of lines is generated as the predicted insertion region. Since the likelihood of the puncture needle being shifted from the puncture guide line increases as puncturing is performed on a deeper portion, and the amount of shift increases, the area of the predicted insertion region may be increased. For example, the wide region may be a region obtained by expanding the puncture guide line by 1.5 cm in both the positive and negative Y-axis directions.

FIG. 22B shows a case when the predicted insertion region is set to a narrow range. In FIG. 22B, a region 232 represents the predicted insertion region.

FIG. 22C shows a case when the predicted insertion region is set to an average range. In FIG. 22C, a region 234 represents the predicted insertion region. The region 234 is wider than the region 232.

FIG. 22D shows a case when the predicted insertion region is set to a wide range. In FIG. 22D, a region 236 represents the predicted insertion region. The region 236 is wider than the region 234.

When the predicted insertion region is set, the puncture needle candidate point extractor 206 performs threshold processing or the like on only the inside of the predicted insertion region to extract needle candidate points from the inside of the predicted insertion region. When the puncture needle candidate points are extracted from only the inside of the predicted insertion region, the number of needle candidate points originating from tissues or the like in the edge image generated from the predicted insertion region decreases. Thus, the proportion of needle candidate points originating from the puncture needle in relation to all needle candidate points increases. Therefore, it is possible to generate the puncture needle candidate line with higher precision.

Figure 23:
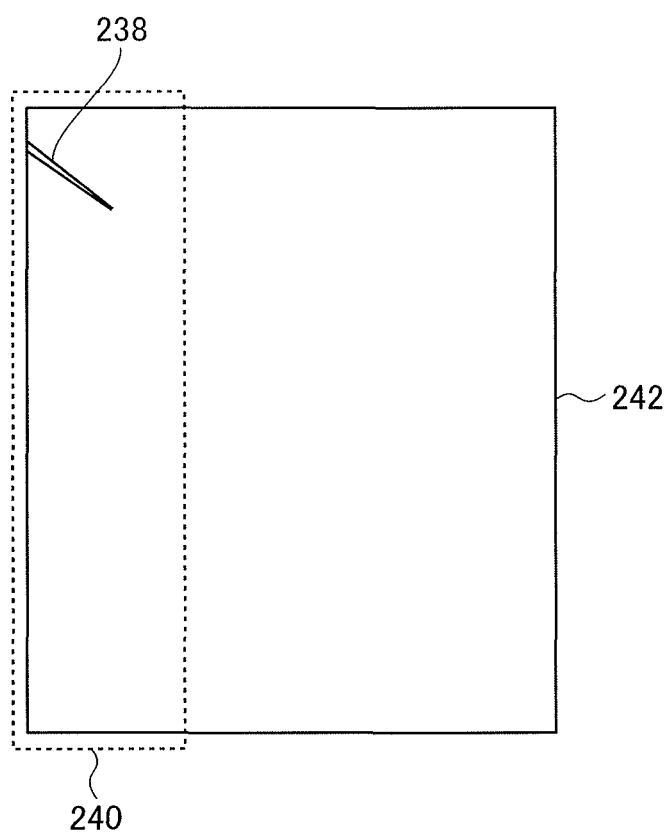
FIG. 23 is a schematic view showing an example of a region of interest within a B-mode image.

The operation of setting the target region which will be subjected to image quality enhancement, described in step S206 will be described with reference to FIG. 23.

The user sets the target region by checking the position of a puncture needle 238 on a B-mode image 242. Specifically, the user checks the position of the puncture needle 238 with naked eyes and sets a region in which the entire puncture needle 238 is included as a target region 240. In FIG. 23, for better understanding of the invention, the puncture needle 238 is depicted in a continuous manner. In this example, although the user sets the target region, the target region may not always be set by the user. For example, the ultrasound image generation apparatus 200 may automatically set a region in which the entire image representing the puncture needle, generated by the puncture needle image generator 216 is included as the target region.

The transceiving controller 202 performs an image quality enhancing process on the target region. Specifically, the transceiving controller 202 causes the probe 222 to perform an acoustic ray increasing process of increasing the number of acoustic rays in the target region to thereby perform the image quality enhancing process so that the target region has higher image quality than region other than the target region. The acoustic ray increasing process is a process of narrowing the distance from which ultrasound waves are irradiated to thereby obtain echo signals more finely. Thus, a high-precision image can be obtained from the region subjected to the acoustic ray increasing process. In this example, although the acoustic ray increasing process is performed on the target region, the image quality enhancing process on the target region is not limited to the acoustic ray increasing process. For example, a steer beam process (a process of irradiating ultrasound waves in a direction vertical to the longitudinal direction of the puncture needle to increase echoes reflected from the puncture needle) or a frequency compound process (a process of increasing the band of transmission and reception signals, dividing the band into several parts to form a plurality of images, averaging these images to thereby decrease speckle noise) may be performed.

When the target region is set in advance, and needle candidate points are extracted from the target region having been subjected to the image quality enhancing process, since Hough transform can be performed using needle candidate points in which noise is reduced, it is possible to improve the precision in specifying the position of the puncture needle. For example, since speckle noise can be reduced when the frequency compound process is performed, the proportion of the puncture needle candidate points originating from the puncture needle increases when threshold processing is performed. In FIG. 23, although the frame border of the target region 240 is depicted so as not to overlap the frame border of the B-mode image 242 for better understanding of the invention, the target region 240 naturally does not include a region on the outer side of the B-mode image 242.

A modified example of a method of displaying the puncture needle image so as to be superimposed on the B-mode image will be described with reference to FIGS. 24A to 24D. In FIGS. 24A to 24D, the puncture needles superimposed on the B-mode image are displayed in different manners. The user can select a desired display mode from the modes of displaying the image representing the puncture needle shown in FIGS. 24A to 24D. In the present modified example, the line, segment, dots representing the puncture needle superimposed on the B-mode image are displayed in a predetermined color, for example, green. However, in FIGS. 24A to 24D, the colored line, segment, dots representing the puncture needle superimposed on the B-mode image are depicted by a black line, a black segment, and black dots.

Figure 24A:
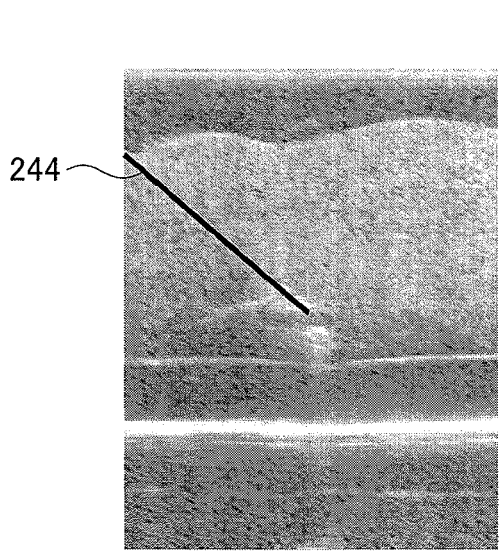
FIG. 24A is a view of a B-mode image on which a line representing a puncture needle is displayed in a superimposed manner.

In FIG. 24A, the puncture needle is displayed as a segment (in FIG. 24A, a deep black segment) 244 having saturation unlike the grayscale used for the B-mode image, and is superimposed on the B-mode image. By displaying in this way, it is possible to display a line representing the puncture needle in a manner clearly different from the B-mode image. Thus, the user can easily understand the position of the puncture needle.

Figure 24B:
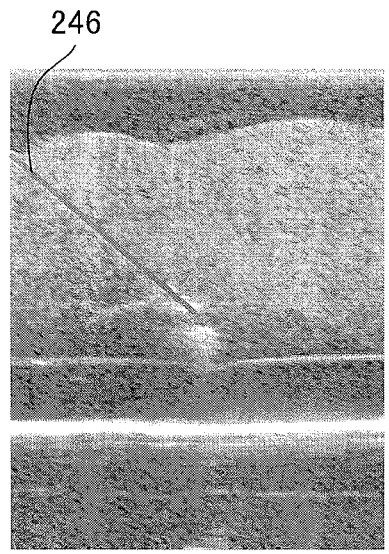
FIG. 24B is a view of a B-mode image on which a line representing a puncture needle is displayed semitransparently in a superimposed manner.

In FIG. 24B, a line 244 representing the puncture needle in FIG. 24A is made transparent to form a semitransparent line 246 (in FIG. 24B, a thin black line 246), the line 246 is superimposed on the B-mode image. The display transparency is 50%, for example. As above, when the puncture needle is displayed so as to be superimposed on the B-mode image as the semitransparent line 246, since the B-mode image is not concealed by the line 246 representing the puncture needle, the user can see both the puncture needle and the B-mode image.

Figure 24C:
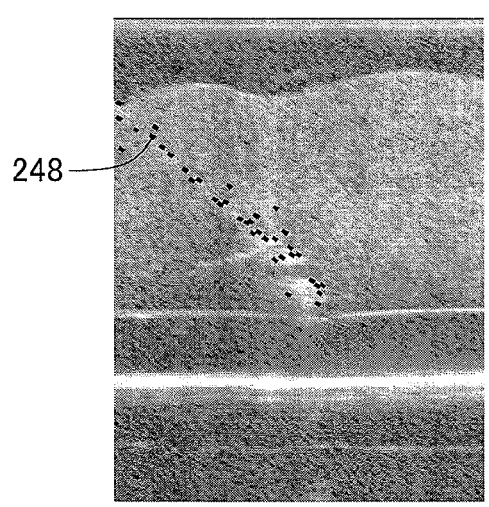
FIG. 24C is a view of a B-mode image on which needle candidate points are colored and displayed in a superimposed manner.

In FIG. 24C, the image representing the puncture needle is not in line form, but needle candidate points 248 (in FIG. 24C, thin black dots 248) are displayed in a color different from the B-mode image and superimposed on the B-mode image. The superimposed needle candidate points 248 are only the puncture needle candidate points of which the X coordinates are equal to or smaller than the X coordinate of the tip position point 136 on the line representing the puncture needle, among the puncture needle candidate points present in the puncture needle presence region. As above, when the puncture needle is not displayed as a line, but only the puncture needle candidate points 248 are colored and displayed so as to be superimposed on the B-mode image, there will be no line which impairs the visualization of the B-mode image.

Figure 24D:
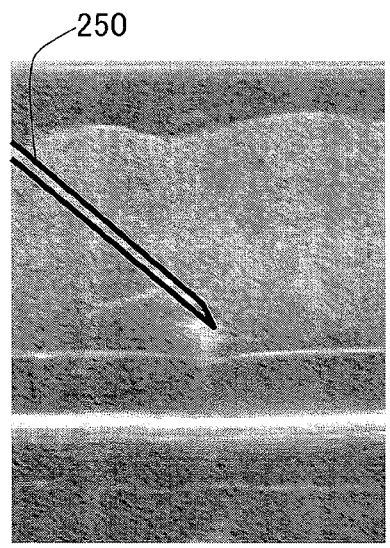
FIG. 24D is a view of a B-mode image on which the outline of a puncture needle is displayed in a superimposed manner.

In FIG. 24D, the outline representing the shape of the puncture needle is fitted to the line representing the puncture needle to form an image 250 (in FIG. 24D, a deep black segment 250) representing the puncture needle. When the outline representing the shape of the puncture needle is displayed so as to be superimposed on the B-mode image, the user can immediately understand the shape of a needle. If the thickness or shape of the puncture needle is known as the puncture needle information stored in the information storage unit 208, the outline of the puncture needle may be an outline having the thickness or shape. Alternatively, the outline may be set by the user.

As described above, according to the ultrasound image generation apparatus 200 of the present embodiment, by extracting the puncture needle candidate points from the B-mode image and performing Hough transform, it is possible to specify the puncture needle candidate line representing the puncture needle and the extension line of the puncture needle. Moreover, the generation apparatus 200 can specify the tip position of the puncture needle within the B-mode image by specifying the region including the specified puncture needle candidate line as the puncture needle presence region and specifying the tip position of the puncture needle based on the luminance information within the puncture needle presence region. Furthermore, the generation apparatus 200 can display the accurate position of the puncture needle so as to be easily understood by the user by displaying the image representing the puncture needle so as to be superimposed on the B-mode image based on the specified position of the puncture needle.

In the present embodiment, although when setting the predicted insertion region, the position of the puncture guide line is determined based on the puncture adapter, the puncture adapter may not always be used in the invention. For example, the puncture guide line may be created by the user, and the puncture guide line may be created by calculating the frame difference of the ultrasound image to calculate the angle or position at which the puncture needle is inserted into the patient. In this case, the predicted insertion region is determined along the newly created puncture guide line. Moreover, a storage unit that stores the past tip position of the puncture needle may be provided to store the past tip position of the puncture needle and the detection timing thereof, and the predicted insertion region may be set based on the past tip position and detection timing of the puncture needle. Moreover, the image representing the puncture needle may be stored in addition to the tip position of the puncture needle.

Figure 25A:
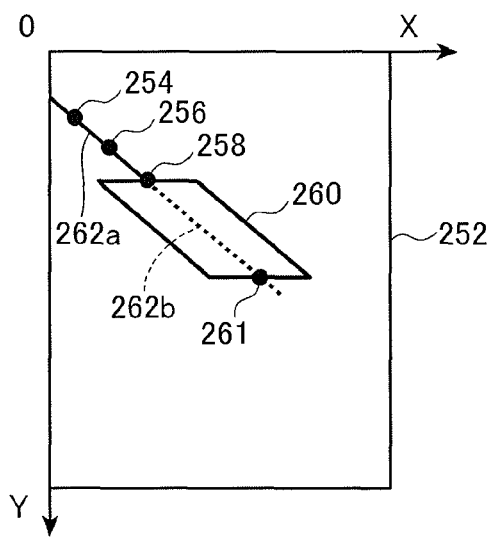
FIG. 25A is a view showing a case of determining a predicted insertion region based on past three tip positions of a puncture needle.
Figure 25B:
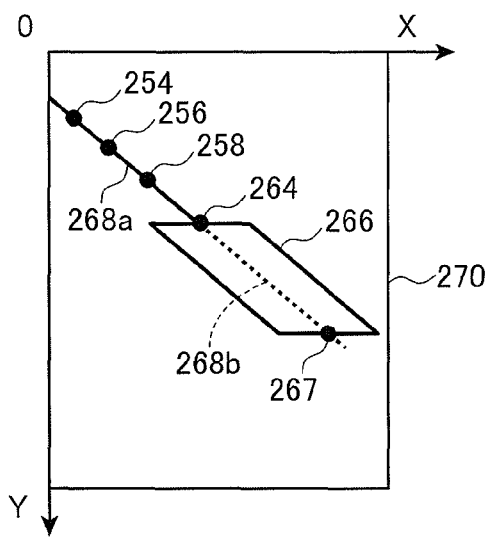
FIG. 25B is a view showing a case of determining a predicted insertion region based on past four tip positions of a puncture needle.

FIGS. 25A and 25B are views showing a method of determining the predicted insertion region using a plurality of past tip positions of the puncture needle. In FIGS. 25A and 25B, a case where an image is positioned in an XY orthogonal coordinate system in which the top left corner of the image is at the origin, a horizontal axis extending from the top left corner to the top right corner is an X axis, and a vertical axis extending from the top left corner to the bottom left corner is a Y axis will be considered. A direction from the top left corner of the image to the top right corner is defined as the positive direction of the X axis, and a direction from the top left corner of the image to the bottom left corner is defined as the positive direction of the Y axis.

In FIG. 25A, a case in which a plurality of points 254, 256, and 258 representing the past tip positions of the puncture needle are present in a B-mode image 252 will be considered. In this example, the point 254 is the tip position of the puncture needle specified earliest. The point 256 is the tip position of the puncture needle detected next to the point 254, and the point 258 is the latest tip position of the puncture needle. Since the three points 254, 256, and 258 are arranged in a line 262a, it can be expected that the next tip position of the puncture needle will be on a broken line 262b which is the extension line of the line passing the three points.

Thus, a region 260 which is disposed under the point 258 having the largest Y coordinate within FIG. 25A and includes the broken line 262b, and of which the size is set taking the bending width of the puncture needle into consideration is determined as a predicted insertion region. Here, the region 260 has a parallelogram shape obtained by expanding the broken line 262b in the X-axis direction. The distance (the difference in Y coordinate) between the points 258 and 261 at which the broken line 262b meets the upper and lower sides of the region 260 is set to be 2 to 3 times the distance between the past tip positions of the puncture needle (for example, the distance between the points 265 and 258). Here, the reason why the size of the region 260 is determined based on the distance (position) of the past tip positions of the puncture needle is to predict the advancing direction of the puncture needle after checking the speed and angle at which the puncture needle was inserted in the past. By checking the past insertion speed and angle of the puncture needle, it is possible to predict the advancing direction of the puncture needle since it can be predicted that at the next detection timing of the tip position, the puncture needle will be inserted at a speed and an angle which are not greatly different from the past insertion speed and angle (that is, the tip position will be displaced by an almost identical distance to the distance between the past tip positions). Although the distance is set with a small margin to be 2 to 3 times the distance between the past tip positions of the puncture needle, the distance may not always be 2 to 3 times larger.

The puncture needle candidate point extractor 206 extracts the puncture needle candidate points within the region 260. When the predicted insertion region is determined using a plurality of past tip positions of the puncture needle, it is possible to further decrease the size of the predicted insertion region. Thus, the proportion of needle candidate points originating from the puncture needle within the predicted insertion region can be increased further. Therefore, it is possible to generate the puncture needle candidate line with high precision. The shape of the region 260 is not limited to a parallelogram, but may be a trapezoidal shape that expands in the X-axis direction as the Y coordinate decreases, for example.

FIG. 25B is a view showing a method of determining the predicted insertion region when detecting the tip position of the puncture needle at the point in time occurring next to FIG. 25A. In FIG. 25B, a point 264 representing the latest tip position of the puncture needle in a B-mode image 270 is added in comparison with FIG. 25A. In this case, a region 266 including a broken line 268b which is an extension line of a line 268a that passes the points 254, 256, 258, and 264 is set as the predicted insertion region. A point 267 is a point at which the broken line 268b meets the lower side of the region 266. As above, even when the number of stored past tip positions of the puncture needle increases, it is possible to set the predicted insertion region based on these positions. Moreover, even when the puncture needle deviates from the original predicted insertion region during puncturing due to bending of the puncture needle caused by the presence of stiff tissues, shift of a probe, or the like, it is possible to detect the puncture needle candidate line with high precision.

In FIGS. 25A and 25B, although a case in which a plurality of past tip positions of the puncture needle are arranged on a line has been described as an example, the plurality of past tip positions of the puncture needle may not always be arranged on a line. For example, a plurality of past tip positions of the puncture needle may be connected like a line graph, and the next predicted insertion region may be set based on the slope of a line connecting the latest two points. Moreover, the predicted insertion region may be set by calculating the slope of a line by performing a least squares method or the like on the latest three points.

Moreover, the width of the predicted insertion region may be determined in accordance with a shift width of the puncture needle with respect to the puncture guide line, which is measured in advance. Alternatively, the width of the predicted insertion region may be adjusted within the range of widths prepared in advance. Moreover, the width of the predicted insertion region may be adjusted during acquisition of ultrasound images. In this case, it is preferable to allocate a function of adjusting the width of the predicted insertion region to a function key or the like of the main body.

Moreover, in the present embodiment, although the width of the predicted insertion region is set from three width steps, the number of width steps is not limited to three. By setting the width steps more finely, the user can set a desired range as finely as possible.

In the present embodiment, when the predicted insertion region is set, the threshold processing is performed on the inside of the predicted insertion region, although the threshold processing may be performed on the entire image, and the Hough transform may be performed using only the puncture needle candidate points within the predicted insertion region. In this case, it is easy to perform the Hough transform.

Moreover, in the present embodiment, the puncture needle candidate line generated by the puncture needle line generator of the puncture needle region specifying unit 212 is expanded to a predetermined width, and a region on the puncture needle candidate line is determined as the puncture needle presence region. However, the method of determining the puncture needle presence region is not limited to this method, and a region including the puncture needle candidate line may be manually determined by the user. For example, the puncture needle presence region may be determined as shown in FIGS. 26A to 26D.

FIG. 26A is a view showing a case in which a puncture needle candidate line 274 is present in a B-mode image 272, and a puncture needle presence region 276 is created by expanding the width of the puncture needle candidate line 274. In FIGS. 26A to 26D, a case where the B-mode image 272 is positioned in an XY orthogonal coordinate system in which the top left corner of the B-mode image 272 is at the origin, a horizontal axis extending from the top left corner to the top right corner is an X axis, and a vertical axis extending from the top left corner to the bottom left corner is a Y axis will be considered. A direction from the top left corner of the B-mode image 272 to the top right corner is defined as the positive direction of the X axis, and a direction from the top left corner of the B-mode image 272 to the bottom left corner is defined as the positive direction of the Y axis. FIG. 26B shows a case in which the user creates a puncture needle presence region 278 by moving the puncture needle presence region 276 shown in FIG. 26A in a direction of decreasing the Y coordinate. FIG. 26C shows a case in which the user creates a puncture needle presence region 280 by moving the puncture needle presence region 276 shown in FIG. 26A in a direction of increasing the Y coordinate. FIG. 26D shows a case in which the user creates a puncture needle presence region 282 having a slope different from the puncture needle candidate line 274. As above, the puncture needle presence region may be adjusted by the user. If the user can adjust the puncture needle presence region, the user can manually set a region in which a large number of needle candidate points which are considered to represent the puncture needle are included as the puncture needle presence region while seeing the edge image. By calculating the average luminance value in the puncture needle presence region set by the user and detecting the tip position of the puncture needle, it is possible to improve the precision in detecting the tip position of the puncture needle.

In the present embodiment, the direction of scanning the change in the average luminance value is determined based on the graph showing the relationship between the X' coordinate and the average luminance. However, since in many cases, puncturing is performed along the direction of a probe mark (a mark indicating a scanning direction) attached to the probe, the target region may be set in the direction of the probe mark.

In the present embodiment, although the target region is set by specifying the tip position of the puncture needle, it is not always necessary to set the target region by specifying the tip position of the puncture needle. For example, the user may check the position of the puncture needle within the B-mode image with naked eyes and set a region including the puncture needle as the target region.

In the present embodiment, although the line representing the puncture needle is generated using the puncture needle candidate line 130 and the point 136 on the puncture needle candidate line 130, having the same X coordinate as the point 134 specified as the tip position of the puncture needle, the line representing the puncture needle may not always be generated in this way. For example, the point 134 which is the tip position of the puncture needle may be used as the ending point, the user may determine the starting point, and a segment may be generated from the starting and ending points.

In the present embodiment, although four variations are illustrated as the display modes of displaying the image representing the puncture needle so as to be superimposed on the B-mode image, the display modes are not limited to these variations. For example, both the line representing the puncture needle and the puncture needle candidate points may be displayed at the same time, and the puncture needle candidate points may be made transparent. Moreover, it is not necessary to display the line representing the puncture needle in a uniform color. For example, the line may be displayed with a gradation or the like, and may be expressed with two colors.

Moreover, it is preferable to allow the user to select a desired thickness of the line representing the puncture needle. For example, the user may select a thickness from various thicknesses set in advance, for example, narrow, medium, bold, and the like, and the user may input the thickness. When the thickness of the puncture needle used is known, the line may be displayed with the same thickness as the thickness of the puncture needle used.

Moreover, it is preferable to allow the user to set the transparency of the line representing the puncture needle. For example, a function may be allocated to an input button prepared on a control panel or the like so that the user can freely set the transparency.

Moreover, the luminance of the line representing the puncture needle may be automatically calculated and set by the ultrasound image generation apparatus. For example, the luminance of the line is determined by normalizing it by a gradation value (for example, 100) using the maximum luminance in the B-mode image before the threshold processing and adding the normalized luminance to the luminance representing the B-mode image.

Moreover, the luminance of the image representing the puncture needle may be automatically set by the ultrasound image generation apparatus. For example, the luminance of the image representing the puncture needle can be set automatically using the average luminance value of several pixels of the B-mode image that are around the image representing the puncture needle which is superimposed on the B-mode image.

Moreover, it is preferable to allow the user to set the predetermined time interval of detecting the tip position of the puncture needle and generating the image representing the puncture needle. The time interval is selected from several time intervals, for example, narrow (1 second), medium (2 seconds), and coarse (3 seconds). These time intervals may be set in advance by system configuration, and a function may be allocated to a button prepared in a control panel or the like. Since the speed at which the puncture needle is inserted into a patient is different depending on the user, the user may set the time interval so that the detection of the tip position of the puncture needle and the generation of the image representing the puncture needle are performed at time intervals corresponding to the insertion speed of the puncture needle. By allowing the user to set a desired time interval so that the detection of the tip position of the puncture needle and the generation of the image representing the puncture needle are performed at time intervals corresponding to the insertion speed of the puncture needle, the process of detecting the tip position of the puncture needle is performed less frequently when the position of the puncture needle is not changed much. Thus, it is possible to decrease the processing load on the apparatus.

In the present embodiment, although the threshold processing or the like is performed on the B-mode image in which the echo signal is expressed by luminance information to thereby specify the tip position of the puncture needle, it is not always necessary to perform the threshold processing or the like on the B-mode image. For example, the threshold processing or the like may be performed on images of other modes or the echo signal itself to thereby specify the tip position of the puncture needle.

The ultrasound image generation apparatus and the ultrasound image generation method according to the second aspect of the invention have the configuration described hereinabove.

Next, an ultrasound image generation apparatus and an ultrasound image generation method according to the third aspect of the invention will be described.

First Embodiment

Figure 27:
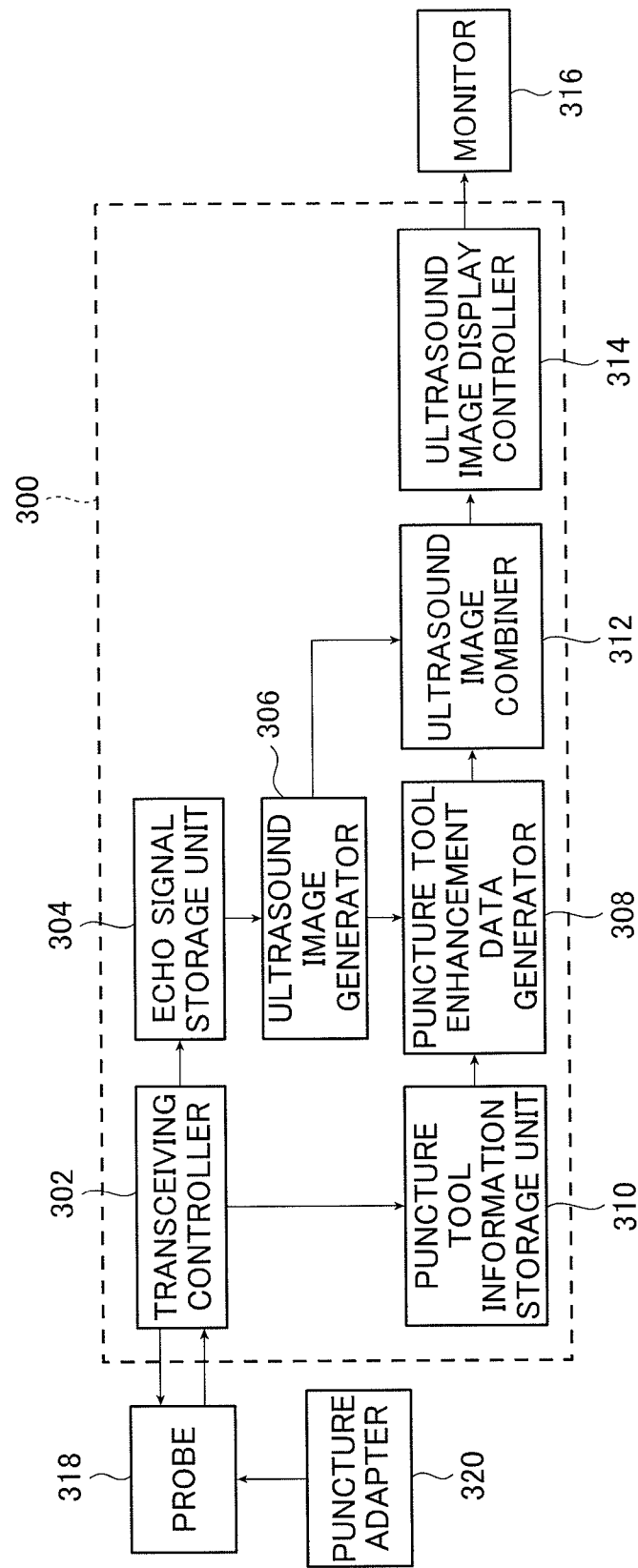
FIG. 27 is a functional block diagram of an embodiment of an ultrasound image generation apparatus according to a third aspect of the invention.

FIG. 27 is a functional block diagram showing a configuration of main parts of an example of an ultrasound image generation apparatus according to the first embodiment of the third aspect of the invention.

An ultrasound image generation apparatus 300 shown in FIG. 27 includes a transceiving controller 302, an echo signal storage unit 304, an ultrasound image generator 306, a puncture tool enhancement data generator 308, a puncture tool information storage unit 310, an ultrasound image combiner 312, and an ultrasound image display controller 314. The generation apparatus 300 is used by being electrically connected to a monitor 316 and a probe 318. Moreover, the probe 318 is used together with a puncture adapter 320. The generation apparatus 300, the monitor 316, the probe 318, and the puncture adapter 320 form an ultrasound diagnostic apparatus 10b, and the generation apparatus 300 and the monitor 316 form a diagnostic apparatus main body 14b. Some constituent elements of the generation apparatus 300 are the same as those of the ultrasound diagnostic apparatus 10 shown in FIGS. 1, 2, 6, and 7, and those of the generation apparatus 200 shown in FIG. 19. In this case, the constituent elements have the same configuration and function, and detailed description thereof will not be provided.

The probe 318 has the same configuration and function as the probe 222 of the generation apparatus 200 shown in FIG. 19. That is, the probe 318 transmits ultrasound waves toward a patient, receives an echo signal reflected from the patient, and outputs the echo signal to the transceiving controller 302. Moreover, the probe 318 outputs an insertion angle output from the puncture adapter 320 to the transceiving controller 302.

The puncture adapter 320 is used by being physically and electrically connected to the probe 318, and serves as a guide along which a puncture needle (not shown) is inserted into the patient. The puncture adapter 320 has the same configuration and function as the puncture adapter 20 of the ultrasound diagnostic apparatus 10 shown in FIG. 1 when the puncture adapter 20 is used by being physically and electrically connected to the probe body 16.

The puncture adapter 320 has a guide groove (not shown) whose angle with respect to the patient is variable, and which enables the user to change the insertion angle. The puncture adapter 320 stores information on the insertion angle. When the puncture adapter 320 is physically connected to the probe 318, since the puncture adapter 320 is also electrically connected to the probe 318, a signal indicating the insertion angle is output to the probe 318. Moreover, the puncture adapter 320 outputs a signal indicating the present insertion angle to the probe 318 whenever the angle of the groove with respect to the patient changes.

The transceiving controller 302 has the same configuration and function as the transceiving controller 202 shown in FIG. 19. That is, the transceiving controller 302 applies ultrasound transmission pulses to piezoelectric elements (not shown) in the probe 318 and causes ultrasound waves to be generated from the probe 318.

The transmission controller 302 amplifies the echo signal output from the probe 318, rejects high-frequency components of the echo signal, performs A/D conversion on the resulting echo signal, and then outputs the digital echo signal to the echo signal storage unit 304. Moreover, the transmission controller 302 outputs the insertion angle output from the puncture adapter 320 to the puncture tool information storage unit 310.

The echo signal storage unit 304 temporarily stores the digital echo signal. The echo signal storage unit 304 has the same configuration and function as the data storage unit 46 of the diagnostic apparatus main body 10a of the ultrasound diagnostic apparatus 10 shown in FIG. 1.

The ultrasound image generator 306 has the same configuration and function as the image generator 204 shown in FIG. 19. That is, the ultrasound image generator 306 generates an acoustic-ray signal from the echo signal stored in the echo signal storage unit 304, corrects the attenuation of the acoustic-ray signal in accordance with the depth of the reflection position of the ultrasound wave, and generates the B-mode image data.

The puncture tool information storage unit 310 has the same configuration and function as the information storage unit 208 shown in FIG. 19. That is, the puncture tool information storage unit 310 stores information on the puncture tool such as a puncture needle.

The puncture tool enhancement data generator 308 performs various noise removal processes on the B-mode image data generated by the ultrasound image generator 306. Moreover, the puncture tool enhancement data generator 308 performs a puncture tool enhancement processing using a filter (hereinafter referred to as a puncture tool enhancement filter) that enhances the puncture tool on the B-mode image data after noise removal based on the insertion angle stored in the puncture tool information storage unit 310. The puncture tool enhancement data generator 308 outputs image data enhanced by the puncture tool enhancement filter, namely puncture tool enhancement data to the ultrasound image combiner 312. Detailed configuration of the puncture tool enhancement data generator 308 will be described later.

The ultrasound image combiner 312 combines the B-mode image data stored in the ultrasound image generator 306 and the puncture tool enhancement data generated by the puncture tool enhancement data generator 308 to thereby generate combined B-mode image data. The ultrasound image combiner 312 outputs the combined B-mode image data to the ultrasound image display controller 314.

The ultrasound image display controller 314 has the same configuration and function as the image display controller 220 shown in FIG. 19. That is, the ultrasound image display controller 314 converts the combined B-mode image data combined by the ultrasound image combiner 312 into display image data and outputs the image data to the monitor 316. In this way, the combined B-mode image (combined ultrasound image) is displayed on the monitor 316.

Figure 28:
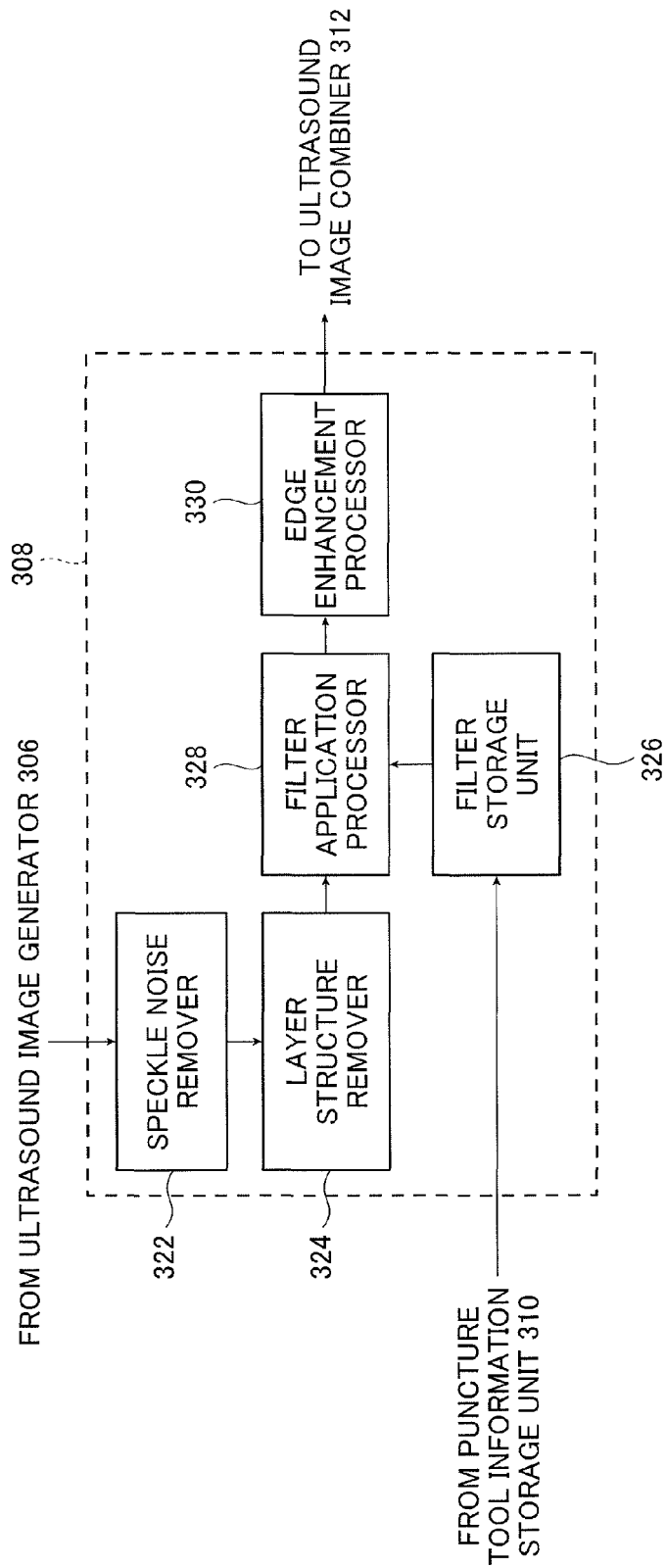
FIG. 28 is a functional block diagram showing a detailed configuration of a puncture tool enhancement data generator of the ultrasound image generation apparatus shown in FIG. 27.

FIG. 28 is a functional block diagram showing a more detailed configuration of the puncture tool enhancement data generator of the ultrasound image generation apparatus shown in FIG. 27. The puncture tool enhancement data generator 308 includes a speckle noise remover 322, a layer structure remover 324, a filter storage unit 326, a filter application processor 328, and an edge enhancement processor 330.

The speckle noise remover 322 has the same configuration and function as the speckle noise remover 90 shown in FIG. 6. That is, the speckle noise remover 322 removes speckle noise in the B-mode image data generated by the ultrasound image generator 306. For example, a median filter is applied.

The layer structure remover 324 has the same configuration and function as the layer structure remover 92 shown in FIG. 6. That is, the layer structure remover 324 performs a layer structure removal processing on the B-mode image data in which the speckle noise is removed by the speckle noise remover 322.

The filter storage unit 326 stores a plurality of puncture tool enhancement filters applied to the B-mode image data. The filter storage unit 326 stores six puncture tool enhancement filters with intervals of 10°, corresponding to insertion angles of 10° to 60°. The plurality of puncture tool enhancement filters are provided from the puncture tool information storage unit 310 to the filter storage unit 326. In the present aspect of the invention, the filter storage unit 326 may not be provided, and these puncture tool enhancement filters may be stored in the puncture tool information storage unit 310 so that a puncture tool enhancement filter applied is read directly from the puncture tool information storage unit 310.

The filter application processor 328 specifies a puncture tool enhancement filter to be used based on the insertion angle stored in the puncture tool information storage unit 310 and reads the specified puncture tool enhancement filter from the filter storage unit 326. For example, when the insertion angle is 10°, a puncture tool enhancement filter for the insertion angle of 10° is read. The filter application processor 328 applies the read puncture tool enhancement filter to the B-mode image data after layer structure removal. Since the puncture tool enhancement filter used therein is a filter corresponding to the insertion angle of the puncture needle, it is possible to defocus the image in the insertion direction of the puncture needle to make a discontinuous puncture needle image continuous. That is, the puncture tool enhancement filter is the defocus filter used in the first aspect of the invention. Thus, the filter application processor 328 has the same configuration and function as the filter application processor 96 shown in FIG. 7.

The edge enhancement processor 330 has the same configuration and function as the edge enhancement processor 98 shown in FIG. 7. That is, the edge enhancement processor 330 performs a process of enhancing the edges of the B-mode image with respect to the B-mode image data to which the puncture tool enhancement filter has been applied. For example, a 1D edge enhancement processing is performed in the vertical direction to the puncture needle to thereby enhance the edges of the puncture needle.

The ultrasound image combiner 312 combines the B-mode image (image data) which has been made continuous in the insertion direction of the puncture needle so as to be superimposed on the original B-mode image (image data) to thereby generate a combined B-mode image (image data). In this way, the whole image of the puncture needle within the tissue can be displayed on the monitor 316 in an easily visible manner.

FIG. 29 is a flowchart showing an example of the operation of the ultrasound image generation apparatus and the ultrasound image generation method according to the present aspect of the invention.

First, B-mode image (ultrasound image) data is generated in step S300, and puncture tool enhancement data is generated in step S302. In step S304, the puncture tool enhancement data is combined with the B-mode image data to thereby generate combined B-mode image. In step S306, the combined B-mode image data is subjected to scan conversion. In step S308, combined B-mode image is displayed on the monitor 316 using the scan-converted combined B-mode image data. In this way, the process ends.

FIG. 30 is a flowchart illustrating the operation of generating puncture tool enhancement data in the step (step S302) of generating puncture tool enhancement data in the ultrasound image generation method shown in FIG. 29 in more detail.

In step S400, speckle noise in the B-mode image (ultrasound image) data is removed. In step S402, a layer structure in the B-mode image data is removed. In step S404, the insertion angle of the puncture tool is specified. In step S406, a puncture tool enhancement filter is applied to the B-mode image data. In step S408, a puncture tool edge enhancement processing is performed to generate puncture tool enhancement data, and the flow proceeds to step S304.

Figure 31C:
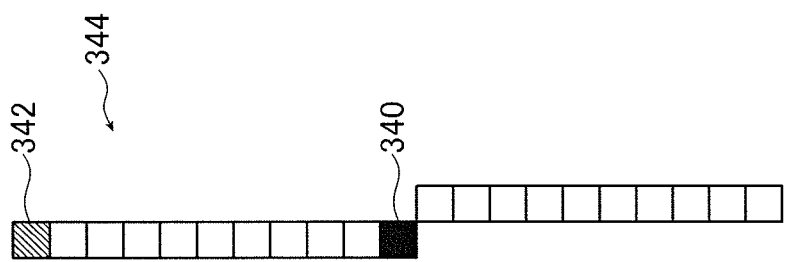
FIG. 31C shows an example of a puncture tool enhancement filter according to the first embodiment when an insertion angle is 30°.
Figure 31B:
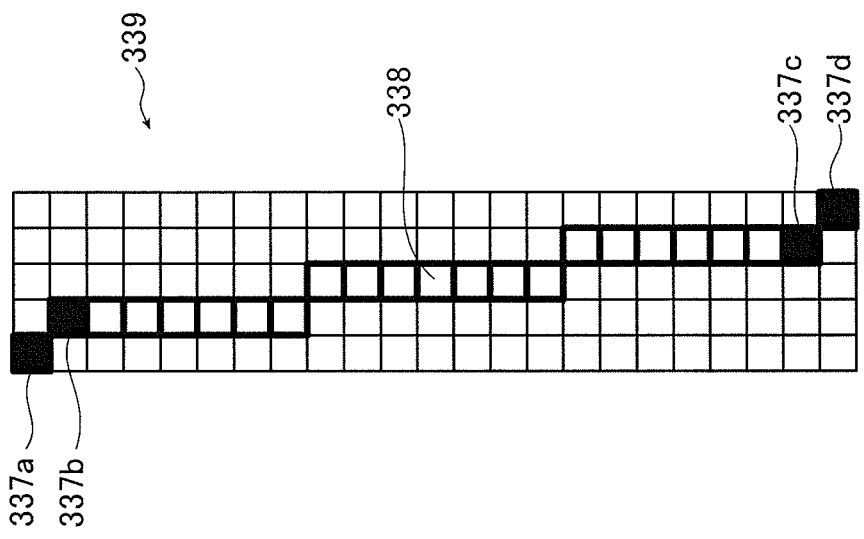
FIG. 31B is an enlarged view of a region in which a puncture needle is disconnected within a B-mode image.
Figure 31A:
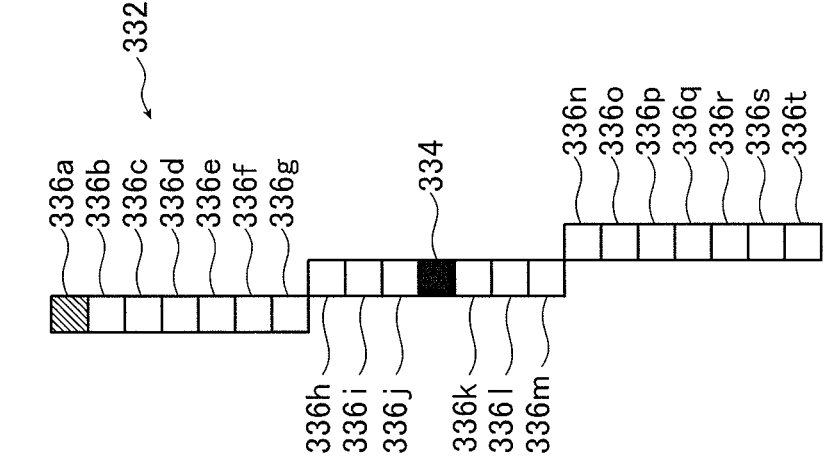
FIG. 31A shows an example of a puncture tool enhancement filter according to a first embodiment of the present aspect when an insertion angle is 10°.

FIGS. 31A and 31C are views each showing the shape of a puncture tool enhancement filter used for generating the puncture tool enhancement data. When the B-mode image is considered as a collection of pixels on a 2D coordinate system, the puncture tool enhancement filter is a filter that performs a weighted addition between the value (image data) of a pixel (hereinafter referred to as a target pixel) subjected to the puncture tool enhancement processing and the value (image data) of a specific pixel around the target pixel. The filter application processor 328 sequentially changes the position of the target pixel and performs the puncture needle enhancement processing on the image data of all pixels in the B-mode image using the puncture needle enhancement filter determined based on the insertion angle.

FIG. 31A shows the shape of a puncture tool enhancement filter 332 used when the insertion angle is 10°. Elements 336a to 336t of the puncture tool enhancement filter 332 represent pixels subjected to weighted addition, and the positions of the elements 336a to 336t represent the positions of the pixels subjected to weighted addition. The puncture tool enhancement filter 332 has a size of 21×3 pixels. The puncture tool enhancement filter 332 has a shape such that, as seen downwardly, a line of every seven pixels arranged in the vertical direction is shifted rightward by one pixel. When the shape of the puncture tool enhancement filter 332 is considered as a 2D matrix with 21 rows and 3 columns, the elements at the first column and 1st to 7th rows (elements 336a to 336g), the elements at the second column and 8th to 14th rows (elements 336h to 336m), and the elements at the third column and 15th to 21st rows (elements 336n to 336t) have their respective filter coefficients. That is, the puncture tool enhancement filter 332 has a shape such that elements at every specified number of rows starting from the first row are shifted from the first column sequentially to an adjacent right column.

An element 334 depicted in black and located at the center of the puncture tool enhancement filter 332 is a target pixel, the position of the element 334 is the position of the target pixel, and the target pixel is located at the center of the puncture tool enhancement filter 332. A hatched element 336a represents one pixel used for the weighted addition of the target pixel. Each of the elements 336b to 336t represents one pixel used for the weighted addition of the target pixel similarly to the element 336a although the elements 336b to 336t are not hatched, and the positions of the elements 336a to 336t represent the positions of the pixels used for the weighted addition. For example, an element 336j adjacent on the upper side of the element 334 represents that weighted addition is performed using the value of a pixel adjacent on the upper side of the target pixel. That is, the shape of the puncture tool enhancement filter represents the positions of neighboring pixels used when a puncture tool enhancement processing is performed on the target pixel. In the puncture tool enhancement filter 332, the target pixel is subjected to weighted addition using the values of two sets of three adjacent pixels (elements 336h to 336m) on the upper and lower sides of the target pixel, the values of pixels (elements 336a to

336g) 4 to 10 pixels above at the left adjacent column, the values of pixels (elements 336n to 336t) 4 to 10 pixels below at the right adjacent column, and the value of the target pixel itself. That is, the target pixel is subjected to weighted addition using the values of neighboring 20 pixels and the value of the target pixel itself.

The reason why the puncture tool enhancement filter 332 has a shape such that elements at every specified number of rows starting from the first row are shifted from the first column sequentially to an adjacent right column is to perform weighted addition between the target pixel and pixels located in the insertion direction of the puncture needle based on the insertion angle and to make the puncture needle image within the B-mode image continuous in the insertion direction of the puncture needle. In this example, although elements at every seven rows (every seven pixels) are shifted as a predetermined length rightward when the insertion angle is 10°, the predetermined length is different depending on the insertion angle. In the present embodiment, since the puncture needle is inserted from the top left corner of the drawing toward the bottom right corner, it is assumed that the puncture tool enhancement filter 332 has a shape such that elements at every specified number of rows starting from the first row are shifted from the first column sequentially to an adjacent right column.

Moreover, since the puncture needle is displayed in a linear shape on the B-mode image (ultrasound image), the puncture needle is highly likely to be present in the pixels located in the insertion direction of the puncture needle. Thus, by performing weighted addition using the pixels located at the positions based on the insertion angle, it is possible to perform weighted addition using not only pixels near the target pixel but also pixels which are located at positions away from the target pixel and at positions where the puncture needle is highly likely to be present.

Moreover, the puncture tool enhancement filter has a size based on the discontinuance interval of the puncture needle within the B-mode image. FIG. 31B is an enlarged view of a region 339 in which the puncture needle within the B-mode image is discontinuous in order to describe the size of the puncture tool enhancement filter. In this example, the puncture tool enhancement filter 332 is taken as an example, and, in a puncture tool region 339, the puncture needle is displayed with a discontinuance interval ideal for applying the puncture tool enhancement filter 332. Pixels 337a, 337b, 337c, and 337d depicted in black in FIG. 31B are pixels representing the puncture needle. In the drawing, a pixel 338 is a pixel located at the center of the region 339. The puncture needle in the region 339 is discontinuous in pixels (19×1 pixels) between the pixels 337b and 337c. The puncture tool enhancement filter 332 has a size such that the pixel region where the puncture needle is discontinuous is expanded by one pixel in upward and downward, as well as rightward and leftward directions. That is, the puncture tool enhancement filter 332 has a size of 21×3 pixels. As above, the puncture tool enhancement filter has a size greater than the interval with which the puncture needle is discontinuous within the B-mode image.

By setting the size of the puncture tool enhancement filter so as to be greater than the discontinuance interval of the puncture needle, even when the puncture tool enhancement filter is applied to the pixel at the center of the region where the puncture needle is discontinuous, pixels representing the puncture needle will be included at both ends of the puncture tool enhancement filter. That is, the puncture tool enhancement filter is a filter that performs weighted addition using at least one of the pixels representing the puncture needle when it is applied to a region where the puncture needle is discontinuous within the B-mode image. By doing so, even when the target pixel is located in a region where the puncture needle is discontinuous within the B-mode image, it is possible to perform weighted addition using pixels representing the puncture needle, located away from the target pixel. Thus, it is possible to make the target pixel have a luminance close to that of the puncture needle image surrounding the target pixel.

FIG. 31C shows the shape of a puncture tool enhancement filter 344 used when the insertion angle is 30°. The puncture tool enhancement filter 344 has a size of 21×2 pixels. When the shape of the puncture tool enhancement filter 344 is considered as a 2D matrix with 21 rows and 2 columns, the elements at the first column and 1st to 11th rows, and the elements at the second column and 12th to 21st rows have their respective filter coefficients. The puncture tool enhancement filter 344 also has a shape such that elements at every specified number of rows starting from the first row are shifted from the first column sequentially to an adjacent right column. Similarly to FIG. 31A, a hatched element 342 represents one pixel, and a pixel 340 depicted in black represents a target pixel. When the insertion angle is 30°, the target pixel is subjected to weighted addition using the values of 10 pixels on the upper side of the target pixel, the values of pixels 1 to 10 pixels below at the right adjacent column, and the value of the target pixel itself. As above, if the insertion angle is different, the shape of the puncture tool enhancement filter applied, namely the position of the pixel used for the weighted addition is also different. The filter storage unit 326 stores a plurality of puncture tool enhancement filters having a shape corresponding to the insertion angle.

Figure 32A:
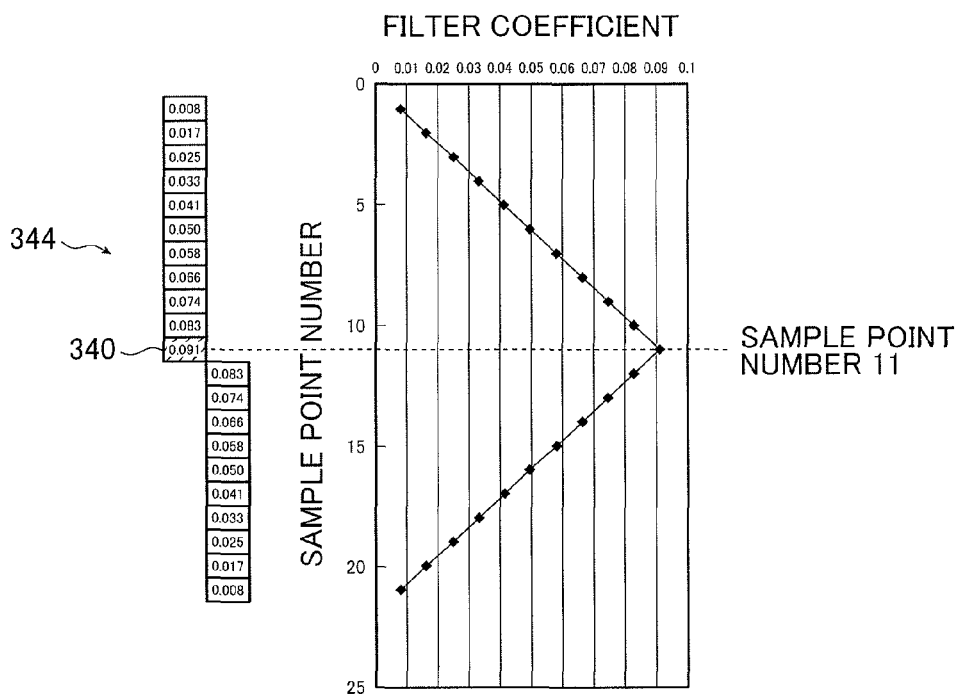
FIG. 32A shows filter coefficients which are uniformly allocated to respective elements.
Figure 32B:
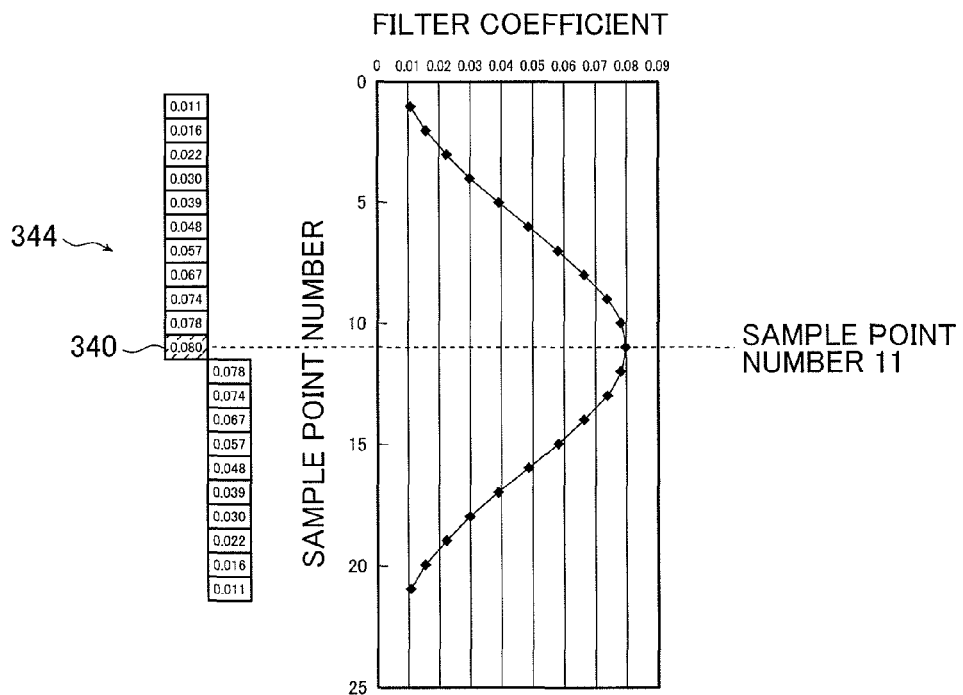
FIG. 32B shows filter coefficients of a Gaussian filter.

The puncture tool enhancement filter designates pixels used for weighted addition and performs addition by applying weights based on the filter coefficients to the respective designated pixels. FIGS. 32A and 32B are views showing the filter coefficients of the respective elements used for weighted addition in the puncture tool enhancement filter 344. The numbers within the respective elements of the puncture tool enhancement filter 344 represent filter coefficients. For example, in FIG. 32A, the element 340 has a filter coefficient of 0.091. The filter coefficients described within the respective elements of the puncture tool enhancement filter 344 are rounded off to the third decimal place.

FIG. 32A shows a case where filter coefficients are evenly allocated to elements on the upper and lower sides of the position of the element 340 which is located at the center of the puncture tool enhancement filter 344. That is, the element 340 (sample point number 11) at the center of the puncture tool enhancement filter 344 has the maximum filter coefficient, and the filter coefficient decreases in proportion to the distance in the vertical direction from the element 340. The sum of the filter coefficients of the respective elements is normalized to 1. In FIG. 32A, the graph shown to the right of the puncture tool enhancement filter 344 shows the numbers within the respective elements of the puncture tool enhancement filter 344, in which the vertical axis represents a sample point number, and the horizontal axis represents a filter coefficient. The sample point number on the vertical axis of the graph of FIG. 32A represents the row number of the element when the puncture tool enhancement filter 344 is considered as a 2D matrix. For example, sample point number 1 represents that the element is on the first row of the first column. The sample point number corresponding to the element 340 (on the 11th row of the 1st column) is 11.

Another method of determining the filter coefficients of the respective elements will be described. For example, the filter coefficients can be generated using a Gaussian filter expressed by Equation 2 which is applied in the first aspect of the invention.

In Equation 2, x represents the position of a pixel in the vertical direction of the drawing when the central element indicated by sample point number 11 is at 0 as shown in FIG. 32A. For example, x=−1 corresponds to the pixel at sample point number 10, and x=1 corresponds to the pixel at sample point number 12. FIG. 32B is a graph in which the vertical axis represents the sample point number and the horizontal axis represents a filter coefficient f(x) when the average $\mu=0$ and the variance $\sigma^2=1$ in Equation 2. In FIG. 32B, the numbers within the respective elements of the puncture tool enhancement filter 344 shown to the left of the graph are the values of the filter coefficients of the respective elements. For example, the element 340 (sample point number 11) has a filter coefficient of 0.080. By determining the filter coefficients of the respective pixels in this way, it is possible to perform weighted addition so that the filter coefficients of the pixels located closer to the target pixel are increased.

The puncture tool enhancement filter is a filter that designates pixels used for weighted addition by the shape (the position of an element) thereof, and performs weighted addition which involves multiplying the values of the designated pixels by the filter coefficients, to thereby obtain the value of the target pixel. The filter application processor 328 performs the puncture tool enhancement processing on all pixels using the puncture tool enhancement filter determined based on the insertion angle.

Figure 33A:
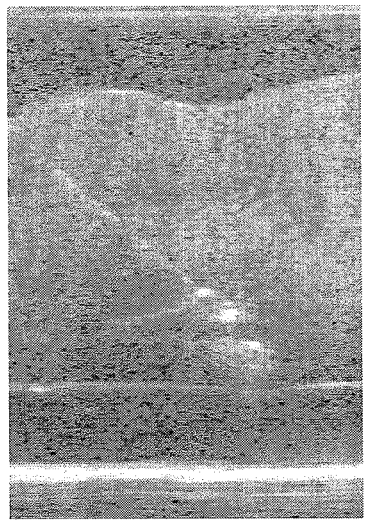
FIG. 33A shows an example of an ultrasound image before a puncture tool enhancement processing.
Figure 33B:
FIG. 33B shows a combined ultrasound image after a puncture tool enhancement processing.

FIG. 33A shows a B-mode image which has not been subjected to the puncture tool enhancement processing, and FIG. 33B shows a combined image of the B-mode image of FIG. 33A and a B-mode image after the puncture tool enhancement processing.

The combined image shown in FIG. 33B is obtained by causing defocusing of the B-mode image before the puncture tool enhancement processing shown in FIG. 33A in the direction of the insertion angle so that the puncture needle is displayed in a continuous manner. In FIGS. 33A and 33B, for better understanding of the effect of the puncture tool enhancement processing by the puncture tool enhancement filter, speckle noise removal processing, layer structure removal processing, and edge enhancement processing were not performed. The generation apparatus 300 applies the puncture tool enhancement filter to the image (image data) in which the speckle noise and the layer structure are removed, and combines a B-mode image after edge enhancement processing with the B-mode image before the puncture tool enhancement processing.

As described above, according to the ultrasound image generation apparatus 300 according to the first embodiment of the present aspect, the puncture tool enhancement filter used is determined based on the insertion angle of the puncture needle, and the puncture tool enhancement processing is performed using the puncture tool enhancement filter so that the B-mode image is made continuous in the insertion direction of the puncture needle. Thus, it is possible to generate an image in which the puncture needle displayed in a discontinuous manner is made continuous. Moreover, since the B-mode image after the puncture tool enhancement processing is combined with the B-mode image before the puncture tool enhancement processing, it is possible to generate an ultrasound image in which the puncture needle is displayed so as to be easily visible to the user.

Moreover, removal of the speckle noise may not always be performed. However, when the puncture tool enhancement filter is applied to the B-mode image in which the speckle noise is removed, it is possible to increase the effect of application of the puncture tool enhancement filter without increasing the size of the puncture tool enhancement filter more than necessary.

In the present embodiment, although six kinds of shapes of the puncture tool enhancement filters are stored in the filter storage unit 326, a larger number of shapes may be stored. Moreover, although puncture tool enhancement filters having shapes corresponding to the range of insertion angles between 10° and 60° are prepared, puncture tool enhancement filters having shapes corresponding to insertion angles, of 10° or less and 60° or more or a puncture tool enhancement filter having a shape corresponding to the insertion angle of 15° or 25° may be prepared.

Moreover, the thickness of the puncture needle may be stored as the puncture tool information, and the shape of the puncture tool enhancement filter may be changed in accordance with the thickness of the puncture needle used. For example, since a region where the puncture needle is likely to be present broadens when the puncture needle is thick, weighted addition may be performed using a wider range of pixels in accordance with the insertion angle.

In the present embodiment, although the puncture tool enhancement filter used is determined based on the insertion angle by the puncture adapter, it is not always necessary to determine the puncture tool enhancement filter based on the insertion angle by the puncture adapter. For example, the puncture tool enhancement filter may be determined based on the insertion angle acquired from an image. That is, high-luminance points corresponding to the tip end of a puncture needle may be extracted from a plurality of B-mode images, the insertion angle of the puncture needle may be acquired from the plurality of tip positions, and the puncture tool enhancement filter may be determined based on the insertion angle.

Second Embodiment

In the first embodiment described above, although a case where the pixels located in the insertion direction of the puncture needle are used for weighted addition using a puncture tool enhancement filter having a step shape has been described as an example, the invention is not particularly limited to this. In the second embodiment below, an aspect in which a puncture tool enhancement filter has a rectangular shape, and weighted addition is performed so that the pixels located in the insertion direction of the puncture needle have a large filter coefficient will be described. Since an ultrasound image generation apparatus according to the second embodiment of the present aspect has the same basic configuration as the generation apparatus 300 described in the first embodiment, the functional block diagram thereof will not be illustrated. Moreover, since the basic operation thereof is the same as that of the generation apparatus 300, illustration thereof will not be provided.

Figure 34:
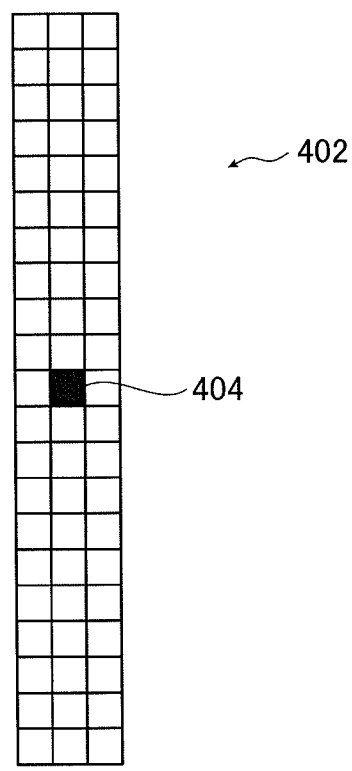
FIG. 34 shows an example of a puncture tool enhancement filter according to a second embodiment when an insertion angle is 10°.

FIG. 34 shows an example of a puncture tool enhancement filter 402 used in the ultrasound image generation apparatus (not shown) according to the second embodiment of the present aspect. The puncture tool enhancement filter 402 is a puncture tool enhancement filter used when the insertion angle is 10°. The puncture tool enhancement filter 402 has a size of 21×3 pixels and has a rectangular shape. In FIG. 34, a pixel 404 is a pixel located at the center of the puncture tool enhancement filter 402. The filter storage unit 326 stores a plurality of rectangular filters having an aspect ratio corresponding to the insertion angle. The plurality of puncture tool enhancement filters have different aspect ratios depending on the insertion angle of the puncture needle. Six puncture tool enhancement filters are stored with intervals of 10° between 10° and 60°. Moreover, the puncture tool enhancement filter has a size based on the interval with which the puncture needle is discontinuous within the B-mode image. In the first embodiment, the weighted addition has been performed using pixels located in the insertion direction of the puncture needle using a puncture tool enhancement filter having a step shape. However, in the present embodiment, neighboring pixels are used regardless of whether the pixels are located in the insertion direction of the puncture needle, whereupon the pixels located in the insertion direction of the puncture needle have a large filter coefficient.

The puncture tool enhancement filter according to the second embodiment is created in advance by the user and stored in the filter storage unit. The puncture tool enhancement filter according to the second embodiment is made up of an odd number of pixels by an odd number of pixels so that the target pixel is located at the center of the filter.

A method of determining the filter coefficients of the respective pixels of the puncture tool enhancement filter according to the second embodiment will be described.

In the second embodiment, for example, the puncture tool enhancement filter can be generated by applying a Gaussian function expressed by Equation 1 applied in the first aspect of the invention.

In Equation 1, as described in the first aspect of the invention, when $\mu x=\mu y=0$, $\sigma_x^2=\sigma_y^2=40$, and $\rho=0.9$, it is possible to create a filter having the size of 81×81 pixels schematically shown in FIG. 5B.

By linearly interpolating the filter shown in FIG. 5B so as to have the sizes of the respective puncture tool enhancement filters, the filter coefficients used for the respective puncture tool enhancement filters are generated. The filter having the size of 81×81 pixels shown in FIG. 5B can be linearly interpolated so as to become a puncture tool enhancement filter having a size of 15×27 pixels (see FIG. 14D), for example. A puncture tool enhancement filter having the size of 15×27 pixels obtained in this way is a puncture tool enhancement filter used when the insertion angle is 10°. The aspect ratio obtained by the linear interpolation is determined based on the insertion angle. In the puncture tool enhancement filter, the filter coefficient is the largest at the center, with the magnitude of the filter coefficient widely varying along the insertion direction of the puncture needle. A target pixel at the center is subjected to weighted addition using the neighboring 15×27 pixels around the target pixel. The value of the target pixel is obtained by performing weighted addition which involves a multiplication of the values of the respective pixels by the filter coefficient of the puncture tool enhancement filter. A puncture tool enhancement filter having an aspect ratio corresponding to the insertion angle created in this way is stored in the filter storage unit.

The ultrasound image generation apparatus according to the present embodiment can determine the puncture tool enhancement filter to be used based on the insertion angle, perform the puncture tool enhancement processing of performing weighted addition with neighboring pixels on all pixels using the determined puncture tool enhancement filter, and generate an image in which the puncture tool is enhanced.

Figure 35A:
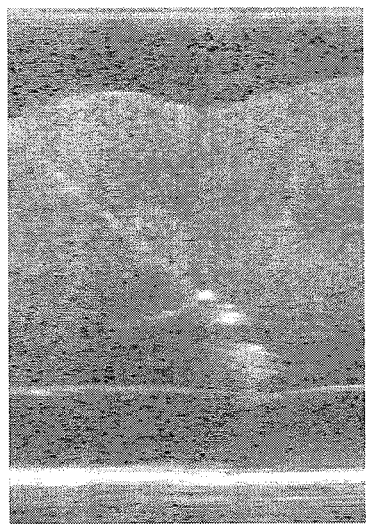
FIG. 35A shows an example of an ultrasound image before a puncture tool enhancement processing.
Figure 35B:
FIG. 35B shows a combined ultrasound image after a puncture tool enhancement processing.

FIG. 35A shows a B-mode image which has not been subjected to the puncture tool enhancement processing, and FIG. 35B shows a combined image in which a B-mode image after application of the puncture tool enhancement filter is combined with the B-mode image before the puncture tool enhancement processing. The combined image shown in FIG. 35B is obtained by causing defocusing of the B-mode image before the puncture tool enhancement processing in the direction of the insertion angle. In FIGS. 35A and 35B, for better understanding of the effect of the filter processing, speckle noise removal processing, layer structure removal processing, and edge enhancement processing were not performed. The ultrasound image generation apparatus according to the second embodiment of the invention performs the puncture tool enhancement processing on the image in which the speckle noise and the layer structure are removed, and combines a B-mode image after edge enhancement processing with the B-mode image before the puncture tool enhancement processing.

In this example, a case of converting into a size of 15×27 pixels has been described as an example, although, as described above, in puncture tool enhancement filters having different sizes, filter coefficients corresponding to the sizes of the respective puncture tool enhancement filters can be generated by linearly interpolating the base filter having the size of 81×81 pixels shown in FIG. 5B.

As described above, according to the ultrasound image generation apparatus according to the second embodiment of the present aspect, weighted addition is performed on all pixels using a rectangular puncture tool enhancement filter having an aspect ratio corresponding to the insertion angle so that pixels located in the insertion direction of the puncture needle have a large filter coefficient. Thus, it is possible to make the B-mode image continuous in the insertion direction of the puncture needle and to generate an image in which the puncture needle displayed in a discontinuous manner is made continuous. Moreover, since an image after application of the puncture tool enhancement filter is combined with the B-mode image before application of the puncture tool enhancement filter, it is possible to generate an ultrasound image in which the puncture needle is displayed so as to be easily understood by the user.

Moreover, since the puncture tool enhancement filter according to the second embodiment has a sufficiently large size, the puncture tool enhancement filter is not likely to be affected by speckle noise. Thus, the speckle noise removal processing may not be performed.

In the present embodiment, although six kinds of shapes of the puncture tool enhancement filters are used, a larger number of shapes may be used. Moreover, although puncture tool enhancement filters having shapes corresponding to the range of insertion angles between 10° and 60° are prepared, puncture tool enhancement filters having shapes corresponding to insertion angles of 10° or less and 60° or more may be prepared.

In the present embodiment, although the puncture tool enhancement filter to be used is determined based on the insertion angle, it is not always necessary to determine the puncture tool enhancement filter based on the insertion angle. For example, the puncture tool enhancement filter may be determined based on an insertion angle acquired from an image. That is, high-luminance points corresponding to the tip end of a puncture needle may be extracted from a plurality of B-mode images, the insertion angle of the puncture needle may be acquired from the plurality of tip positions, and the puncture tool enhancement filter may be determined based on the insertion angle.

Third Embodiment

In the first and second embodiments of the present aspect, the puncture tool enhancement processing was performed on the B-mode image using the puncture tool enhancement filter having a shape corresponding to the insertion angle of the puncture needle. However, in the third embodiment, the B-mode image is rotated in accordance with the insertion angle, and the puncture tool enhancement processing is performed using the same puncture tool enhancement filter.

Figure 36:
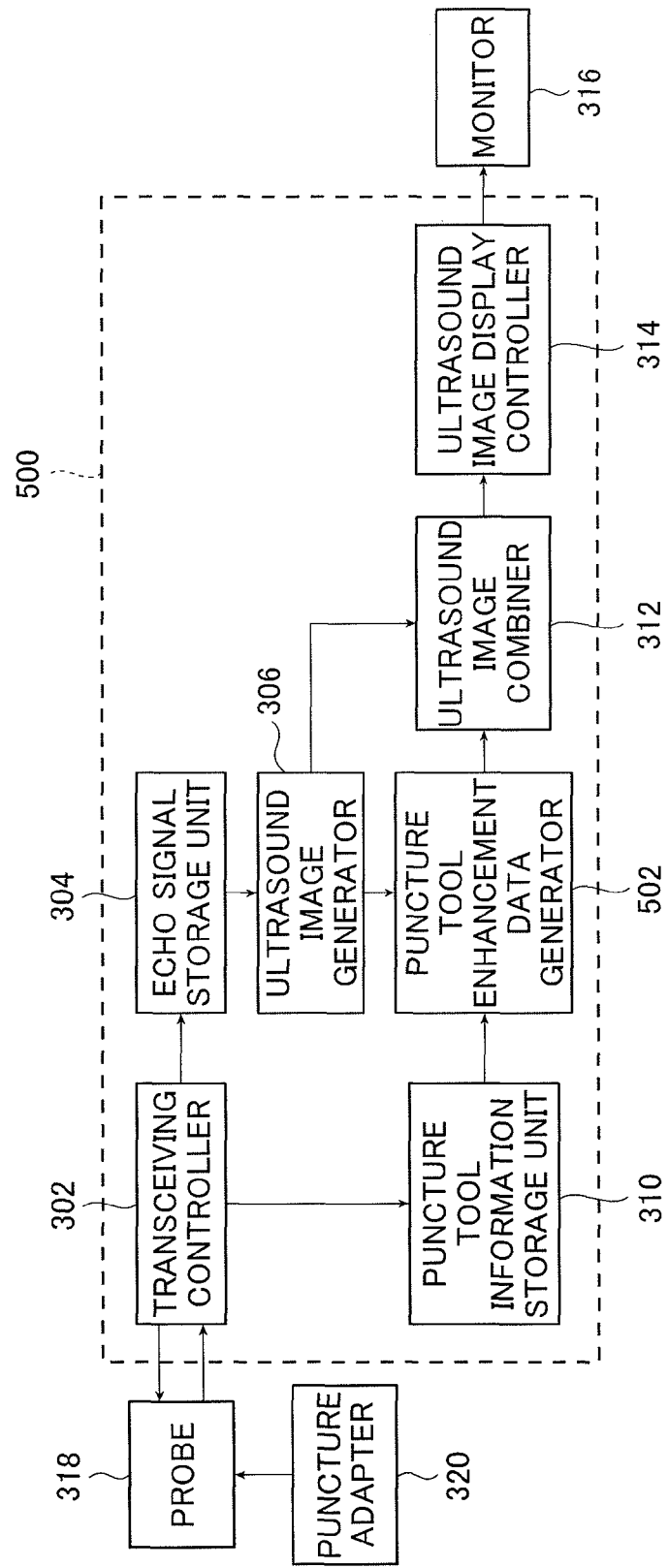
FIG. 36 is a functional block diagram of another embodiment of the ultrasound image generation apparatus according to the third aspect of the invention.

FIG. 36 is a block diagram showing a configuration of main parts of an ultrasound image generation apparatus 500 according to the third embodiment of the present aspect. The same constituent elements as the ultrasound image generation apparatus 300 described in the first embodiment will be denoted by the same reference numerals, and description thereof will not be provided.

The ultrasound image generation apparatus 500 shown in FIG. 36 is different from the ultrasound image generation apparatus 300 shown in FIG. 27, mainly in that a puncture tool enhancement data generator 502 has a different configuration.

Figure 37:
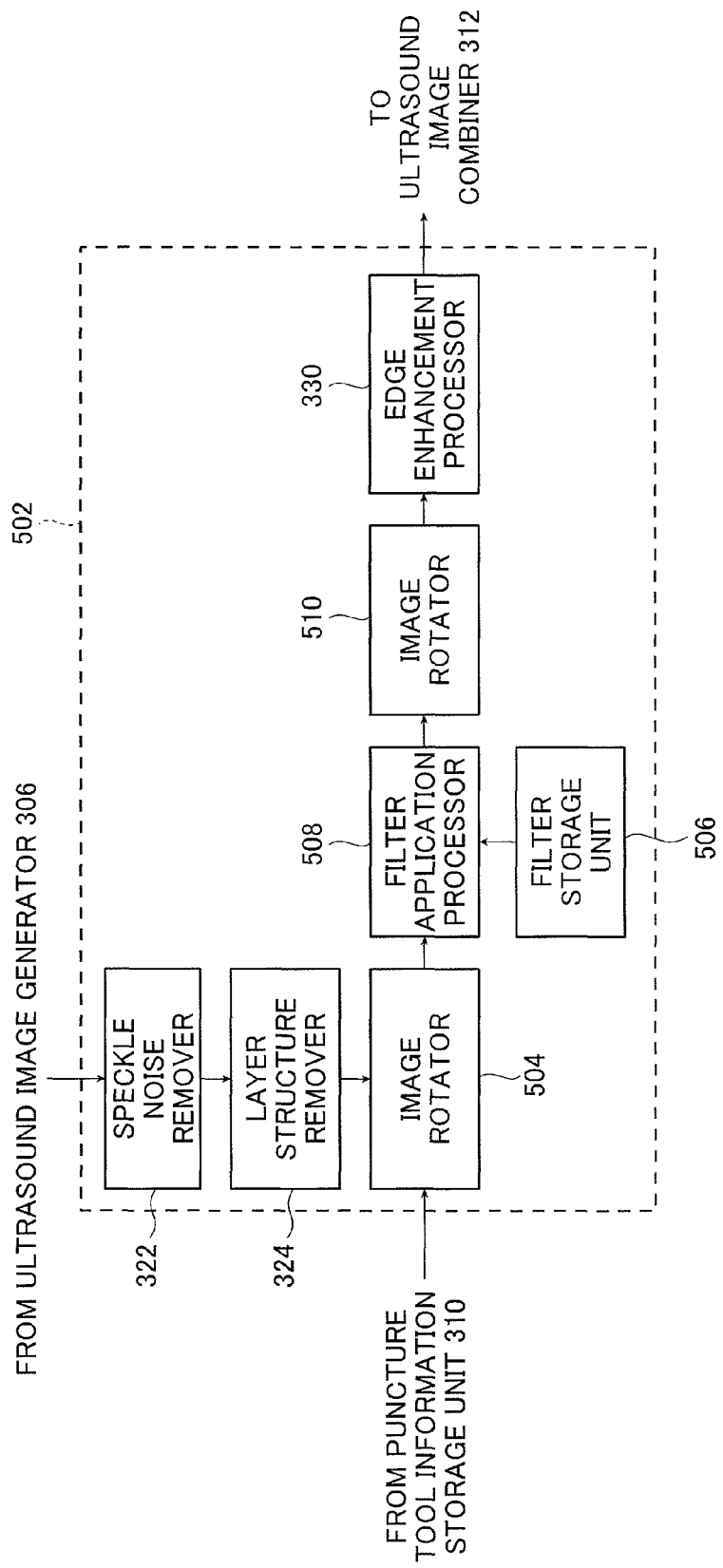
FIG. 37 is a functional block diagram showing a detailed configuration of a puncture tool enhancement data generator of the ultrasound image generation apparatus shown in FIG. 36.

FIG. 37 is a functional block diagram showing a more detailed configuration of a puncture tool enhancement data generator of the ultrasound image generation apparatus shown in FIG. 36.

The puncture tool enhancement data generator 502 shown in FIG. 37 includes the speckle noise remover 322, the layer structure remover 324, a first image rotator 504, a filter storage unit 506, a filter application processor 508, a second image rotator 510, and the edge enhancement processor 330.

The first image rotator 504 rotates a B-mode image (image data) in which a layer structure is removed by the layer structure remover 324 by an amount corresponding to the insertion angle stored in the puncture tool information storage unit 310. Specifically, the image rotator 504 performs an image rotation process on the B-mode image data so that the puncture needle is displayed horizontally.

The filter storage unit 506 stores a puncture tool enhancement filter ideal when the puncture needle is displayed horizontally. The puncture tool enhancement filter has a size based on the interval with which the puncture needle is discontinuous within the B-mode image. Specifically, the puncture tool enhancement filter has a size such that a horizontal width is slightly larger than the interval with which the puncture needle is discontinuous within the B-mode image. That is, when the puncture tool enhancement filter is applied to a region where the puncture needle is discontinuous within the B-mode image after rotation, a part of the puncture needle is always included. The discontinuance interval of the puncture tool is measured in advance by the user based on the B-mode image.

The filter application processor 508 performs the puncture tool enhancement processing on the B-mode image (image data) after rotation using the puncture tool enhancement filter stored in the filter storage unit 506.

The second image rotator 510 rotates the B-mode image data so that the B-mode image after the puncture tool enhancement processing is displayed with the angle before the B-mode image is rotated by the first image rotator 504.

Figure 38:
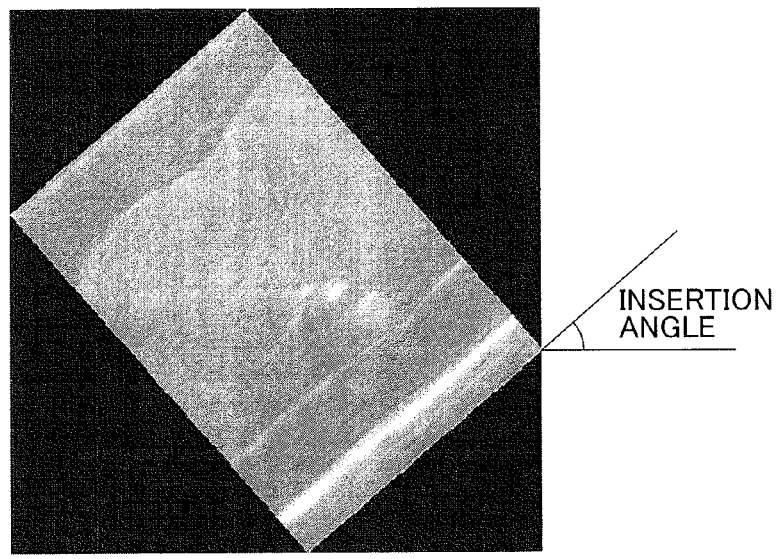
FIG. 38 shows an example of an ultrasound image rotated so that an image representing a puncture tool becomes horizontal.

FIG. 38 shows a B-mode image after rotation by the first image rotator 504. The B-mode image is rotated by an angle based on the insertion angle so that the puncture needle becomes horizontal as shown in FIG. 38. For example, when the puncture needle is inserted from the top left corner to the bottom right corner, and the insertion angle is 30°, the B-mode image is rotated counterclockwise by 30°.

The puncture tool enhancement filter according to the third embodiment is created in advance by the user and stored in the filter storage unit 506 similarly to the second embodiment. The puncture tool enhancement filter stored in the filter storage unit 506 is a filter ideal when the puncture needle is displayed horizontally.

Figure 39:
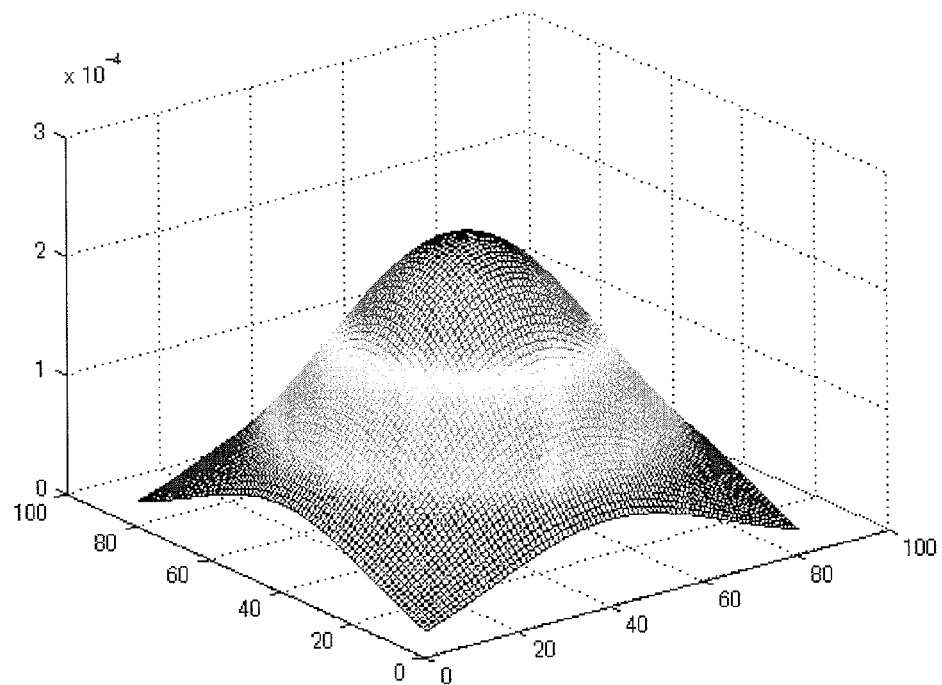
FIG. 39 is a view showing an example of a Gaussian filter serving as the base that determines a filter coefficient of the puncture tool enhancement filter according to a third embodiment of the present aspect.

FIG. 39 is an example of a Gaussian filter serving as the basis when allocating filter coefficients to the respective pixels in the puncture tool enhancement filter used in the third embodiment. The 2D coordinates on the lower side represent positions, and the vertical axis represents a filter coefficient. This Gaussian filter is a 2D Gaussian filter in which the average $\mu=0$, the variance $\sigma^2=25$, and the correlation value $\rho=0$. The filter coefficient of the Gaussian filter reaches its maximum at the center of the 2D coordinate system, and decreases as the distance from the center increases. Pixels on a concentric circle about the center of the 2D coordinate system have the same filter coefficient. By linearly interpolating the Gaussian filter, a puncture tool enhancement filter which has a size with a horizontal width slightly larger than the interval with which the puncture needle is discontinuous within the B-mode image, and which is ideal when the puncture needle is displayed horizontally.

The ultrasound image generation apparatus 500 applies the puncture tool enhancement filter ideal when the puncture needle is displayed horizontally to the B-mode image (image data) rotated so that the puncture needle is displayed horizontally. That is, the puncture tool enhancement filter used is a filter ideal when the puncture needle is displayed horizontally regardless of the insertion angle. The ultrasound image generation apparatus 500 rotates the B-mode image (image data) after the puncture tool enhancement processing so that the puncture needle has the original angle, and then performs edge enhancement processing. The ultrasound image generation apparatus 500 combines the B-mode image before the puncture tool enhancement processing with the B-mode image to which the puncture tool enhancement filter has been applied and which has been subjected to the edge enhancement processing and displays a combined image.

As described above, according to the ultrasound image generation apparatus 500 according to the third embodiment of the invention, the B-mode image is rotated in accordance with the insertion angle, and the puncture tool enhancement filter is applied to the B-mode image in which the puncture needle is displayed horizontally, whereby the B-mode image is made continuous in the insertion direction of the puncture needle. Thus, it is possible to generate an image in which the puncture needle displayed in a discontinuous manner is made continuous. Moreover, since the B-mode image is rotated in accordance with the insertion angle to generate an image in which the puncture needle is displayed horizontally, it is only necessary to prepare just a puncture tool enhancement filter ideal when the puncture needle is displayed horizontally. Thus, it is not necessary to prepare a plurality of puncture tool enhancement filters corresponding to the insertion angle. Moreover, since the B-mode image to which the puncture tool enhancement filter has been applied is combined with the original B-mode image, it is possible to generate an ultrasound image in which the puncture needle is displayed so as to be easily understood by the user.

The speckle noise removal processing may not always be performed. When the puncture tool enhancement filter is applied to a B-mode image in which the speckle noise is removed, it is possible to decrease the size of the puncture tool enhancement filter.

As described above, according to the third aspect of the invention, the puncture tool enhancement processing is performed on the B-mode image using the puncture tool enhancement filter corresponding to the insertion angle of the puncture needle, and the B-mode image after the puncture tool enhancement processing is combined with the B-mode image before the puncture tool enhancement processing.

Thus, it is possible to generate an image in which the puncture needle displayed in a discontinuous manner is made continuous.

In the respective embodiments, although the puncture tool enhancement processing and the image combination process have been performed on the B-mode image before scan conversion, the processes may be performed after scan conversion. That is, the scan conversion may be performed before the puncture tool enhancement data is generated. Thus, the scan conversion may be performed by the ultrasound image generator 306 and may be performed by the ultrasound image combiner 312. Moreover, in the respective embodiments, the B-mode image after the puncture tool enhancement processing has been superimposed on the B-mode image before the puncture tool enhancement processing to generate the combined B-mode image. However, the B-mode image after the puncture tool enhancement processing and the B-mode image before the puncture tool enhancement processing may be subjected to scan conversion and combined so as to be arranged in a parallel arrangement to generate a combined B-mode image of a parallel arrangement.

Moreover, in the respective embodiments, although the insertion angle was output from the puncture adapter, it is not always necessary to output the insertion angle from the puncture adapter. For example, the user may measure and input the insertion angle while seeing an ultrasound image, and may check the setting of the puncture adapter and store the insertion angle in advance in the puncture tool information storage unit 310.

Moreover, in the respective embodiments, although the puncture tool enhancement filter or filters have been stored in advance in the filter storage unit, the user may create a puncture tool enhancement filter ideal for a patient. For example, the user may create a new puncture tool enhancement filter by inputting the filter size, variance, average, correlation value, and the like as the setting items of the puncture tool enhancement filter. The newly created puncture tool enhancement filter is preferably stored in the filter storage unit so as to be used as necessary.

Moreover, in the respective embodiments, the layer structure removal processing may not always be performed. However, the layer structure removal processing has the following advantage. That is, when the puncture tool enhancement filter is applied to a B-mode image in which the layer structure is removed, it is possible to remove connected portions other than the puncture needle and to improve the effect of application of the puncture tool enhancement filter.

In the respective embodiments, the edge enhancement processing may not always be performed. However, the edge enhancement processing has the following advantage. That is, since it is possible to enhance the edges between the puncture needle and the other portions, the user can easily recognize the position of the puncture needle. Moreover, although a 1D edge enhancement processing in the vertical direction to the puncture needle is performed as the edge enhancement processing, the edge enhancement processing is not limited to the 1D edge enhancement processing but may be a 2D edge enhancement processing in the vertical direction to the puncture needle, for example.

In the respective embodiments, although a process using a median filter has been performed as the process of removing the speckle noise, the process of removing the speckle noise is not limited to the process using the median filter. For example, a spatial compounding method, a frequency compounding method, morphology processing, or the like may be performed.

Moreover, in the respective embodiments, a plurality of images after application of the puncture tool enhancement filter may be generated at different points in time, and the respective images may be averaged to generate a time-averaged B-mode image. Moreover, a 3D filter that appropriately changes the filter coefficient in accordance with time may be applied.

Moreover, in the respective embodiments, a puncture tool connection process may be performed on an image after application of the puncture tool enhancement filter so that the parts of the discontinuous puncture needle within the image are connected together. For example, the image after application of the puncture tool enhancement filter is binarized to extract high-luminance points, and the extracted high-luminance points are subjected to Hough transform, whereby a line that connects the parts of the discontinuous puncture needle is generated. When the generated line is displayed so as to be superimposed on the puncture needle, it appears to the user that the parts of the discontinuous puncture tool are connected together. The puncture tool connection process may not always be performed on the image after application of the puncture tool enhancement filter, but may be performed on an image after the edge enhancement processing, for example.

The ultrasound image generation apparatus and the ultrasound image generation method of the third aspect of the invention have the above-described configuration.

Although the respective configurations in the respective aspects of the invention are realized by a combination of a central processing unit (CPU) and software for causing the CPU to execute various processes, the configurations may be realized by digital circuits or analog circuits. The software is stored in an internal memory and is not shown.

Moreover, when an algorithm of the ultrasound image generation method according to the invention is described in a program language and compiled as necessary, and an ultrasound image generation program is stored in a memory (recording medium) and executed by an information processor of another apparatus, the same functions as the ultrasound diagnostic apparatus and the ultrasound image generation apparatus according to the respective aspects of the invention can be realized. That is, a program for causing a computer (CPU) to execute the ultrasound image generation method of the invention and a recording medium with the program recorded thereon are also included in the embodiment of the invention.

While the ultrasound diagnostic apparatus, the ultrasound image generation apparatus, and the ultrasound image generation method according to the invention have been described by way of various embodiments and examples, the invention is not limited to these embodiments and examples, and various improvements and changes can be made without departing from the scope of the invention.

The ultrasound diagnostic apparatus, the ultrasound image generation apparatus, and the ultrasound image generation method according to the invention can be used when acquiring tomographic images of a subject to be examined into which a puncture tool is inserted using ultrasound waves.

What is claimed is:
1. An ultrasound diagnostic apparatus comprising:
an ultrasound transceiving unit configured to transmit ultrasound waves toward a subject to be examined into which a puncture tool is inserted, receive reflected waves of an ultrasound waves reflected from the subject and the puncture tool, and generate echo signals of time-sequential frames based on the received reflected waves;

an ultrasound image generation unit configured to generate an ultrasound image of the subject based on the echo signals generated by the ultrasound transceiving unit;

an image display unit configured to display the ultrasound image generated by the ultrasound image generation unit;

a differential echo signal generation unit configured to generate a differential echo signal between time-sequential frames from the echo signals of the time-sequential frames that are acquired during inserting the puncture tool in the subject at a predetermined angle;

a tip candidate detection unit configured to perform a tip detection process based on the differential echo signal generated by the differential echo signal generation unit to thereby detect at least one tip candidate including a tip end of the puncture tool; and a tip candidate processing unit configured to highlight a tip candidate of the puncture tool detected by the tip candidate detection unit to thereby generate a tip image in which one or more tip candidates of the puncture tool are highlighted, wherein the image display unit displays the tip image of the puncture tool highlighted by the tip candidate processing unit so as to be superimposed on the ultrasound image generated by the ultrasound image generation unit, wherein the differential echo signal generation unit generates a differential image based on the generated differential echo signal, wherein the tip candidate detection unit performs the tip detection process on the differential mage generated by the differential echo signal generation unit to detect the tip candidate of the puncture tool, and wherein the differential echo signal generation unit adjusts a time difference between the time-sequential frames used for generating the differential image in accordance with an insertion speed of the puncture tool.

2. The ultrasound diagnostic apparatus according to claim 1,
wherein the tip candidate detection unit performs a process of detecting the tip candidate of the puncture tool based on a luminance difference of the differential echo signal generated by the differential echo signal generation unit as the tip detection process.

3. The ultrasound diagnostic apparatus according to claim 1,
wherein the tip candidate processing unit highlights the tip candidate of the puncture tool detected by the tip candidate detection unit in accordance with a positive/negative sign of a luminance difference of the differential echo signal.

4. The ultrasound diagnostic apparatus according to claim 1,
wherein as a highlighting process for highlighting the tip candidate, the tip candidate processing unit performs a process of coloring the tip candidate of the puncture tool detected by the tip candidate detection unit to generate a color tip image, or a process of increasing a luminance of the tip candidate to generate a high-luminance tip image, or a process of coloring the tip candidate and then increasing the luminance thereof to generate a high-luminance color tip image.

5. The ultrasound diagnostic apparatus according to claim 1,
wherein the tip candidate detection unit further determines a positive/negative sign of a luminance difference of the differential echo signal, and
wherein the tip candidate processing unit changes a color and luminance used for highlighting the tip candidate of the puncture tool detected by the tip candidate detection unit in accordance with the positive/negative sign of the luminance difference of the differential echo signal determined by the tip candidate detection unit.

6. The ultrasound diagnostic apparatus according to claim 1,
wherein the tip candidate detection unit performs a process of extracting a portion having a luminance difference on the differential image generated by the differential echo signal generation unit as the tip detection process to thereby detect the tip candidate of the puncture tool, the luminance different being equal to or larger or smaller than a predetermined value.

7. The ultrasound diagnostic apparatus according to claim 1,
wherein the tip candidate detection unit performs lookup table processing using a lookup table for performing gradation processing on the differential image in order to extract a portion having a luminance difference within the differential image generated by the differential echo signal generation unit as the tip detection process to thereby detect the tip candidate of the puncture tool.

8. The ultrasound diagnostic apparatus according to claim 7,
wherein the lookup table used for the lookup table processing by the tip candidate detection unit is adjusted in accordance with at least one of the ultrasound image and the differential image.

9. The ultrasound diagnostic apparatus according to claim 1,
wherein the tip candidate detection unit detects the tip candidate of the puncture tool based on a luminance difference of the differential image and a size and density of a region detected based on the luminance difference as the tip detection process.

10. The ultrasound diagnostic apparatus according to claim 1,
wherein the tip candidate detection unit performs tip enhancement filtering on the differential image as the tip detection process to thereby detect the tip candidate of the puncture tool.

11. The ultrasound diagnostic apparatus according to claim 1,
wherein the tip candidate detection unit performs a median filtering process or a filtering process which involves calculating a sum of luminance values of pixels near a predetermined point and enhancing only a portion having a large luminance sum on the differential image as the tip detection process to thereby detect the tip candidate of the puncture tool.

12. The ultrasound diagnostic apparatus according to claim 1,
wherein the tip candidate detection unit searches a region near the tip candidate of the puncture tool detected earlier than a frame displayed on the image display unit to thereby detect the tip candidate of the puncture tool from the differential image based on the displayed frame.

13. The ultrasound diagnostic apparatus according to claim 1,
wherein the tip candidate detection unit searches a region near a line that connects the tip candidates of the puncture tool detected at two points in time earlier than a frame displayed on the image display unit to thereby detect the tip candidate of the puncture tool from the differential image based on the displayed frame.

14. The ultrasound diagnostic apparatus according to claim 1,
wherein the differential echo signal generation unit uses a plurality of frames of two frames or more before as past frames used for creating the differential image.

15. The ultrasound diagnostic apparatus according to claim 1,
wherein the differential echo signal generation unit performs signal processing for reducing a speckle pattern and at least one of signal processing for causing defocusing in a direction of the puncture tool and signal processing for connecting the puncture tool on the time-sequential echo signal as preprocessing and then generates the differential echo signal.

16. The ultrasound diagnostic apparatus according to claim 1,
wherein the image display unit also displays the image of the tip candidate of the puncture tool detected in a point of a past time to thereby display an insertion trajectory of the puncture tool.

17. The ultrasound diagnostic apparatus according to claim 1, further comprising:
an image combination unit configured to combine the tip image in which the tip candidate of the puncture tool generated by the tip candidate processing unit is highlighted so as to be superimposed on the ultrasound image generated by the ultrasound image generation unit to thereby generate a combined image,
wherein the image display unit displays the combined image combined by the image combination unit.

18. An ultrasound image generation method comprising:
transmitting ultrasound waves to a subject to be examined into which a puncture tool is inserted;
receiving reflected waves of the ultrasound waves reflected from the subject and the puncture tool;
generating echo signals of time-sequential frames based on the received reflected waves;
generating an ultrasound image of the subject based on the generated echo signals;
generating a differential echo signal between time-sequential frames from the echo signals of the time-sequential frames that are acquired during inserting the puncture tool in the subject at a predetermined angle;
generating a differential image based on the generated differential echo signal;
adjusting a time difference between the time-sequential frames used for generating the differential image in accordance with an insertion speed of the puncture tool;
performing a tip detection process based on the generated differential image to thereby detect at least one tip candidate including a tip end of the puncture tool;
highlighting a tip candidate of the puncture tool detected; and
displaying the tip candidate of the puncture tool on a display unit so as to be superimposed on the generated ultrasound image.

19. An ultrasound diagnostic apparatus comprising:
a probe that transmits ultrasound waves toward a subject to be examined into which a puncture tool is inserted, receive reflected waves of an ultrasound waves reflected from the subject and the puncture tool, and generate echo signals of time-sequential frames based on the received reflected waves;
an image generator that generates an ultrasound image of the subject based on the echo signals;
a display unit that displays the ultrasound image generated;
a differential image generator that generates a differential echo signal between time-sequential frames from the echo signals of the time-sequential frames that are acquired during inserting the puncture tool in the subject at a predetermined angle;
a tip candidate detector that performs a tip detection process based on the differential echo signal generated by the differential echo signal generation unit to thereby detect at least one tip candidate including a tip end of the puncture tool; and
a tip candidate processor that highlights the tip candidate of the puncture tool detected by the tip candidate detector to thereby generate a tip image in which one or more tip candidates of the puncture tool are highlighted; and
an image combiner that combines the tip image in which the tip candidate of the puncture tool generated by the tip candidate processor is highlighted so as to be superimposed on the ultrasound image generated by the image generator to thereby generate a combined image,
wherein the display unit displays the combined image,
wherein the differential image generator generates a differential image based on the generated differential echo signal,
a tip candidate detector performs the tip detection process on the differential image generated by the differential image generator to detect the tip candidate of the puncture tool, and
the differential image generator adjusts a time difference between the time-sequential frames used for generating the differential image in accordance with an insertion speed of the puncture tool.

* * * * *